(12) United States Patent
Batross et al.

(10) Patent No.: US 9,326,788 B2
(45) Date of Patent: May 3, 2016

(54) LOCKOUT MECHANISM FOR USE WITH ROBOTIC ELECTROSURGICAL DEVICE

(75) Inventors: Jonathan T. Batross, Mason, OH (US);
Gregory A. Trees, Loveland, OH (US);
Foster B. Stulen, Mason, OH (US);
Randolph Stewart, Cincinnati, OH (US); Chad P. Boudreaux, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 663 days.

(21) Appl. No.: 13/539,110

(22) Filed: Jun. 29, 2012

(65) Prior Publication Data
US 2014/0005654 A1    Jan. 2, 2014

(51) Int. Cl.
*A61B 17/32* (2006.01)
*A61B 18/14* (2006.01)
*A61B 19/00* (2006.01)
*A61B 17/29* (2006.01)

(52) U.S. Cl.
CPC ......... *A61B 17/320092* (2013.01); *A61B 18/14* (2013.01); *A61B 19/2203* (2013.01); *A61B 19/30* (2013.01); *A61B 2017/2927* (2013.01); *A61B 2018/1455* (2013.01)

(58) Field of Classification Search
CPC ............... A61B 17/320092; A61B 2018/1455
USPC .......................................................... 606/27
See application file for complete search history.

(56) References Cited

U.S. PATENT DOCUMENTS

| 969,528 A | 9/1910 | Disbrow |
|---|---|---|
| 1,570,025 A | 1/1926 | Young |
| 1,813,902 A | 7/1931 | Bovie |
| 2,442,966 A | 6/1948 | Wallace |
| 2,704,333 A | 3/1955 | Calosi et al. |

(Continued)

FOREIGN PATENT DOCUMENTS

| AU | 2003241752 A1 | 9/2003 |
|---|---|---|
| CN | 1634601 A | 7/2005 |

(Continued)

OTHER PUBLICATIONS

International Search Report for PCT/US2013/045814, dated Oct. 24, 2013 (4 pages).

(Continued)

*Primary Examiner* — Joseph Dietrich

(57) ABSTRACT

A robotically controlled surgical tool including a lockout mechanism is provided. The surgical tool may comprise an instrument mounting portion. The instrument mounting portion includes a housing, a plate, a shaft assembly comprising an end effector, and a coupler to couple the shaft assembly to the instrument mounting portion. The end effector comprises a first jaw member and a second jaw member, the first and second jaw members defining a channel therebetween, and a blade slideably receivable within the channel to cut tissue located between the first and second jaw members. The surgical tool may include an actuation mechanism to actuate the end effector to provide reciprocating movement of the blade within the channel. A lockout mechanism is coupled to the actuation mechanism. The lockout mechanism may selectively enable reciprocating movement of the blade. An interface mechanically and electrically couples the instrument mounting portion to a robotic manipulator.

20 Claims, 48 Drawing Sheets

(56) References Cited

U.S. PATENT DOCUMENTS

| | | |
|---|---|---|
| 2,736,960 A | 3/1956 | Armstrong |
| 2,849,788 A | 9/1958 | Creek |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,053,124 A | 9/1962 | Balamuth et al. |
| 3,082,805 A | 3/1963 | Royce |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,526,219 A | 9/1970 | Balamuth |
| 3,554,198 A | 1/1971 | Tatoian et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,776,238 A | 12/1973 | Peyman et al. |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,012,647 A | 3/1977 | Balamuth et al. |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,444 A | 5/1980 | Bonnell et al. |
| 4,300,083 A | 11/1981 | Heiges |
| 4,302,728 A | 11/1981 | Nakamura |
| 4,306,570 A | 12/1981 | Matthews |
| 4,445,063 A | 4/1984 | Smith |
| 4,491,132 A | 1/1985 | Aikins |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,545,374 A | 10/1985 | Jacobson |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,808,154 A | 2/1989 | Freeman |
| 4,819,635 A | 4/1989 | Shapiro |
| 4,827,911 A | 5/1989 | Broadwin et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,850,354 A | 7/1989 | McGurk-Burleson et al. |
| 4,852,578 A | 8/1989 | Companion et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,881,550 A | 11/1989 | Kothe |
| 4,896,009 A | 1/1990 | Pawlowski |
| 4,903,696 A | 2/1990 | Stasz et al. |
| 4,915,643 A | 4/1990 | Samejima et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,013,956 A | 5/1991 | Kurozumi et al. |
| 5,015,227 A | 5/1991 | Broadwin et al. |
| 5,026,370 A | 6/1991 | Lottick |
| 5,026,387 A | 6/1991 | Thomas |
| 5,042,707 A | 8/1991 | Taheri |
| 5,084,052 A | 1/1992 | Jacobs |
| 5,105,117 A | 4/1992 | Yamaguchi |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,162,044 A | 11/1992 | Gahn et al. |
| 5,163,421 A | 11/1992 | Bernstein et al. |
| 5,163,537 A | 11/1992 | Radev |
| 5,167,725 A | 12/1992 | Clark et al. |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grezeszykowski |
| 5,188,102 A | 2/1993 | Idemoto et al. |
| D334,173 S | 3/1993 | Liu et al. |
| 5,209,719 A | 5/1993 | Baruch et al. |
| 5,213,569 A | 5/1993 | Davis |
| 5,214,339 A | 5/1993 | Naito |
| 5,218,529 A | 6/1993 | Meyer et al. |
| 5,221,282 A | 6/1993 | Wuchinich |
| 5,226,909 A | 7/1993 | Evans et al. |
| 5,226,910 A | 7/1993 | Kajiyama et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,312,023 A | 5/1994 | Green et al. |
| 5,312,425 A | 5/1994 | Evans et al. |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,387,215 A | 2/1995 | Fisher |
| 5,389,098 A | 2/1995 | Tsuruta et al. |

(56) References Cited

U.S. PATENT DOCUMENTS

| | | |
|---|---|---|
| 5,394,187 A | 2/1995 | Shipp |
| 5,396,266 A | 3/1995 | Brimhall |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,419,761 A | 5/1995 | Narayanan et al. |
| 5,421,829 A | 6/1995 | Olichney et al. |
| 5,423,844 A | 6/1995 | Miller |
| 5,438,997 A | 8/1995 | Sieben et al. |
| 5,445,639 A | 8/1995 | Kuslich et al. |
| 5,449,370 A | 9/1995 | Vaitekunas |
| 5,451,220 A | 9/1995 | Ciervo |
| 5,456,684 A | 10/1995 | Schmidt et al. |
| 5,471,988 A | 12/1995 | Fujio et al. |
| 5,472,443 A | 12/1995 | Cordis et al. |
| 5,478,003 A | 12/1995 | Green et al. |
| 5,483,501 A | 1/1996 | Park et al. |
| 5,486,162 A | 1/1996 | Brumbach |
| 5,490,860 A | 2/1996 | Middle et al. |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,540,693 A | 7/1996 | Fisher |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,573,424 A | 11/1996 | Poppe |
| 5,577,654 A | 11/1996 | Bishop |
| 5,591,187 A | 1/1997 | Dekel |
| 5,593,414 A | 1/1997 | Shipp et al. |
| 5,601,601 A | 2/1997 | Tal et al. |
| 5,603,773 A | 2/1997 | Campbell |
| 5,607,436 A | 3/1997 | Pratt et al. |
| 5,618,304 A | 4/1997 | Hart et al. |
| 5,618,492 A | 4/1997 | Auten et al. |
| 5,620,447 A | 4/1997 | Smith et al. |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,678,568 A | 10/1997 | Uchikubo et al. |
| 5,690,269 A | 11/1997 | Bolanos et al. |
| 5,694,936 A | 12/1997 | Fujimoto et al. |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,717,306 A | 2/1998 | Shipp |
| 5,728,130 A | 3/1998 | Ishikawa et al. |
| 5,730,752 A | 3/1998 | Alden et al. |
| 5,733,074 A | 3/1998 | Stöck et al. |
| 5,741,226 A | 4/1998 | Strukel et al. |
| 5,766,164 A | 6/1998 | Mueller et al. |
| 5,772,659 A | 6/1998 | Becker et al. |
| 5,792,135 A | 8/1998 | Madhani et al. |
| 5,792,138 A | 8/1998 | Shipp |
| 5,792,165 A | 8/1998 | Klieman et al. |
| 5,805,140 A | 9/1998 | Rosenberg et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,957 A | 11/1998 | Schulz et al. |
| 5,843,109 A | 12/1998 | Mehta et al. |
| 5,851,212 A | 12/1998 | Zirps et al. |
| 5,858,018 A | 1/1999 | Shipp et al. |
| 5,873,873 A | 2/1999 | Smith et al. |
| 5,873,882 A | 2/1999 | Straub et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,627 A | 5/1999 | Spaulding |
| 5,906,628 A | 5/1999 | Miyawaki et al. |
| 5,911,699 A | 6/1999 | Anis et al. |
| 5,916,229 A | 6/1999 | Evans |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,024,741 A | 2/2000 | Williamson, IV et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,048,224 A | 4/2000 | Kay |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,096,033 A | 8/2000 | Tu et al. |
| 6,099,542 A | 8/2000 | Cohn et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |

(56) References Cited

U.S. PATENT DOCUMENTS

| | | |
|---|---|---|
| 6,142,994 A | 11/2000 | Swanson et al. |
| 6,147,560 A | 11/2000 | Erhage et al. |
| 6,152,902 A | 11/2000 | Christian et al. |
| 6,154,198 A | 11/2000 | Rosenberg |
| 6,159,160 A | 12/2000 | Hsei et al. |
| 6,159,175 A | 12/2000 | Strukel et al. |
| 6,162,194 A | 12/2000 | Shipp |
| 6,165,150 A | 12/2000 | Banko |
| 6,174,310 B1 | 1/2001 | Kirwan, Jr. |
| 6,179,853 B1 | 1/2001 | Sachse et al. |
| 6,183,426 B1 | 2/2001 | Akisada et al. |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,500,312 B2 | 12/2002 | Wedekamp |
| 6,506,208 B2 | 1/2003 | Hunt et al. |
| 6,511,478 B1 | 1/2003 | Burnside et al. |
| 6,511,493 B1 | 1/2003 | Moutafis et al. |
| 6,514,267 B2 | 2/2003 | Jewett |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,558,376 B2 | 5/2003 | Bishop |
| 6,561,983 B2 | 5/2003 | Cronin et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| D477,408 S | 7/2003 | Bromley |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,607,540 B1 | 8/2003 | Shipp |
| 6,610,059 B1 | 8/2003 | West, Jr. |
| 6,616,450 B2 | 9/2003 | Mossle et al. |
| 6,619,529 B2 | 9/2003 | Green et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,644,532 B2 | 11/2003 | Green et al. |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,899 B2 | 1/2004 | Wiener et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,716,215 B1 | 4/2004 | David et al. |
| 6,719,692 B2 | 4/2004 | Kleffner et al. |
| 6,719,776 B2 | 4/2004 | Baxter |
| 6,723,091 B2 | 4/2004 | Goble et al. |
| D490,059 S | 5/2004 | Conway et al. |
| 6,731,047 B2 | 5/2004 | Kauf et al. |
| 6,733,506 B1 | 5/2004 | McDevitt et al. |
| 6,739,872 B1 | 5/2004 | Turri |
| 6,740,079 B1 | 5/2004 | Eggers et al. |

(56) References Cited

U.S. PATENT DOCUMENTS

| | | |
|---|---|---|
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,770,072 B1 | 8/2004 | Truckai et al. |
| 6,773,409 B2 | 8/2004 | Truckai et al. |
| 6,773,443 B2 | 8/2004 | Truwit et al. |
| 6,773,444 B2 | 8/2004 | Messerly |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,790,173 B2 | 9/2004 | Saadat et al. |
| 6,790,216 B1 | 9/2004 | Ishikawa |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,827,712 B2 | 12/2004 | Tovey et al. |
| 6,828,712 B2 | 12/2004 | Battaglin et al. |
| 6,835,082 B2 | 12/2004 | Gonnering |
| 6,849,073 B2 | 2/2005 | Hoey et al. |
| 6,860,878 B2 | 3/2005 | Brock |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,899,685 B2 | 5/2005 | Kermode et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,929,602 B2 | 8/2005 | Hirakui et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,994,708 B2 | 2/2006 | Manzo |
| 7,001,335 B2 | 2/2006 | Adachi et al. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,066,893 B2 | 6/2006 | Hibner et al. |
| 7,066,895 B2 | 6/2006 | Podany |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,204,820 B2 | 4/2007 | Akahoshi |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,235,071 B2 | 6/2007 | Gonnering |
| 7,244,262 B2 | 7/2007 | Wiener et al. |
| 7,258,688 B1 | 8/2007 | Shah et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupré |
| 7,300,431 B2 | 11/2007 | Dubrovsky |
| 7,300,435 B2 | 11/2007 | Wham et al. |
| 7,300,446 B2 | 11/2007 | Beaupre |
| 7,303,531 B2 | 12/2007 | Lee et al. |
| 7,303,557 B2 | 12/2007 | Wham et al. |
| 7,306,597 B2 | 12/2007 | Manzo |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,364,577 B2 | 4/2008 | Wham et al. |
| RE40,388 E | 6/2008 | Gines |
| 7,380,695 B2 | 6/2008 | Doll et al. |

(56) References Cited

U.S. PATENT DOCUMENTS

| | | |
|---|---|---|
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,462,181 B2 | 12/2008 | Kraft et al. |
| 7,464,846 B2 | 12/2008 | Sheltion, IV et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,494,468 B2 | 2/2009 | Rabiner et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,544,200 B2 | 6/2009 | Houser |
| 7,549,564 B2 | 6/2009 | Boudreaux |
| 7,559,450 B2 | 7/2009 | Wales et al. |
| 7,567,012 B2 | 7/2009 | Namikawa |
| 7,569,057 B2 | 8/2009 | Liu et al. |
| 7,572,266 B2 | 8/2009 | Young et al. |
| 7,578,820 B2 | 8/2009 | Moore et al. |
| 7,582,084 B2 | 9/2009 | Swanson et al. |
| 7,582,095 B2 | 9/2009 | Shipp et al. |
| 7,585,181 B2 | 9/2009 | Olsen |
| 7,588,176 B2 | 9/2009 | Timm et al. |
| 7,601,119 B2 | 10/2009 | Shahinian |
| 7,621,930 B2 | 11/2009 | Houser |
| 7,641,653 B2 | 1/2010 | Dalla Betta et al. |
| 7,654,431 B2 | 2/2010 | Hueil et al. |
| 7,659,833 B2 | 2/2010 | Warner et al. |
| 7,665,647 B2 | 2/2010 | Shelton, IV et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,846 B2 | 4/2010 | Ryan |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,751,115 B2 | 7/2010 | Song |
| D621,503 S | 8/2010 | Otten et al. |
| 7,766,210 B2 | 8/2010 | Shelton, IV et al. |
| 7,766,693 B2 | 8/2010 | Sartor et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,784,662 B2 | 8/2010 | Wales et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,819,819 B2 | 10/2010 | Quick et al. |
| D627,066 S | 11/2010 | Romero |
| 7,824,401 B2 | 11/2010 | Manzo et al. |
| 7,832,611 B2 | 11/2010 | Boyden et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,892,606 B2 | 2/2011 | Thies et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,824 B2 | 3/2011 | Masuda et al. |
| 7,922,061 B2 | 4/2011 | Shelton, IV et al. |
| 7,922,651 B2 | 4/2011 | Yamada et al. |
| D637,288 S | 5/2011 | Houghton |
| D638,540 S | 5/2011 | Ijiri et al. |
| 7,936,203 B2 | 5/2011 | Zimlich |
| 7,951,095 B2 | 5/2011 | Makin et al. |
| 7,951,165 B2 | 5/2011 | Golden et al. |
| 7,959,050 B2 | 6/2011 | Smith et al. |
| 7,959,626 B2 | 6/2011 | Hong et al. |
| 7,972,329 B2 | 7/2011 | Refior et al. |
| 7,976,544 B2 | 7/2011 | McClurken et al. |
| 7,981,050 B2 | 7/2011 | Ritchart et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,070,711 B2 | 12/2011 | Bassinger et al. |
| 8,070,762 B2 | 12/2011 | Escudero et al. |
| 8,075,558 B2 | 12/2011 | Truckai et al. |
| 8,089,197 B2 | 1/2012 | Rinner et al. |
| 8,097,012 B2 | 1/2012 | Kagarise |
| 8,105,323 B2 | 1/2012 | Buysse et al. |
| 8,142,461 B2 | 3/2012 | Houser et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,877 B2 | 5/2012 | Klimovitch et al. |
| D661,801 S | 6/2012 | Price et al. |
| D661,802 S | 6/2012 | Price et al. |
| D661,803 S | 6/2012 | Price et al. |

(56) References Cited

U.S. PATENT DOCUMENTS

| | | | |
|---|---|---|---|
| D661,804 S | 6/2012 | Price et al. |
| 8,197,472 B2 | 6/2012 | Lau et al. |
| 8,197,502 B2 | 6/2012 | Smith et al. |
| 8,210,411 B2 | 7/2012 | Yates et al. |
| 8,226,675 B2 | 7/2012 | Houser et al. |
| 8,235,917 B2 | 8/2012 | Joseph et al. |
| 8,236,019 B2 | 8/2012 | Houser |
| 8,236,020 B2 | 8/2012 | Smith et al. |
| 8,241,271 B2 | 8/2012 | Millman et al. |
| 8,246,575 B2 | 8/2012 | Viola |
| 8,246,615 B2 | 8/2012 | Behnke |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,273,087 B2 | 9/2012 | Kimura et al. |
| D669,992 S | 10/2012 | Schafer et al. |
| D669,993 S | 10/2012 | Merchant et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,888 B2 | 10/2012 | Whitman |
| 8,298,223 B2 | 10/2012 | Wham et al. |
| 8,298,225 B2 | 10/2012 | Gilbert |
| 8,303,576 B2 | 11/2012 | Brock |
| 8,303,580 B2 | 11/2012 | Wham et al. |
| 8,319,400 B2 | 11/2012 | Houser et al. |
| 8,323,302 B2 | 12/2012 | Robertson et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,967 B2 | 1/2013 | Stulen |
| 8,357,103 B2 | 1/2013 | Mark et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,545 B2 | 4/2013 | Smith et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,359 B2 | 8/2013 | Whitman et al. |
| 8,512,365 B2 | 8/2013 | Wiener et al. |
| 8,523,889 B2 | 9/2013 | Stulen et al. |
| 8,531,064 B2 | 9/2013 | Robertson et al. |
| 8,535,340 B2 | 9/2013 | Allen |
| 8,535,341 B2 | 9/2013 | Allen |
| 8,546,996 B2 | 10/2013 | Messerly et al. |
| 8,546,999 B2 | 10/2013 | Houser et al. |
| 8,568,400 B2 | 10/2013 | Gilbert |
| 8,573,461 B2 | 11/2013 | Shelton, IV et al. |
| 8,573,465 B2 | 11/2013 | Shelton, IV |
| 8,579,928 B2 | 11/2013 | Robertson et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,616,431 B2 | 12/2013 | Timm et al. |
| 8,623,027 B2 | 1/2014 | Price et al. |
| 8,650,728 B2 | 2/2014 | Wan et al. |
| 8,652,155 B2 | 2/2014 | Houser et al. |
| 8,659,208 B1 | 2/2014 | Rose et al. |
| 8,690,582 B2 | 4/2014 | Rohrbach et al. |
| 8,696,366 B2 | 4/2014 | Chen et al. |
| 8,704,425 B2 | 4/2014 | Giordano et al. |
| 8,709,031 B2 | 4/2014 | Stulen |
| 8,749,116 B2 | 6/2014 | Messerly et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,764,735 B2 | 7/2014 | Coe et al. |
| 8,773,001 B2 | 7/2014 | Wiener et al. |
| 8,779,648 B2 | 7/2014 | Giordano et al. |
| 8,808,319 B2 | 8/2014 | Houser et al. |
| 8,827,992 B2 | 9/2014 | Koss et al. |
| 8,845,537 B2 | 9/2014 | Tanaka et al. |
| 8,882,791 B2 | 11/2014 | Stulen |
| 8,888,776 B2 | 11/2014 | Dietz et al. |
| 8,888,809 B2 | 11/2014 | Davison et al. |
| 8,900,259 B2 | 12/2014 | Houser et al. |
| 8,911,460 B2 | 12/2014 | Neurohr et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,547 B2 | 2/2015 | Dietz et al. |
| 8,968,355 B2 | 3/2015 | Malkowski et al. |
| 8,974,477 B2 | 3/2015 | Yamada |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,903 B2 | 3/2015 | Weir et al. |
| 9,017,326 B2 | 4/2015 | DiNardo et al. |
| 9,039,695 B2 | 5/2015 | Giordano et al. |
| 9,044,261 B2 | 6/2015 | Houser |
| 9,050,093 B2 | 6/2015 | Aldridge et al. |
| 9,050,124 B2 | 6/2015 | Houser |
| 9,060,775 B2 | 6/2015 | Wiener et al. |
| 9,060,776 B2 | 6/2015 | Yates et al. |
| 9,066,747 B2 | 6/2015 | Robertson |
| 9,072,539 B2 | 7/2015 | Messerly et al. |
| 9,089,360 B2 | 7/2015 | Messerly et al. |
| 9,095,367 B2 | 8/2015 | Olson et al. |
| 9,107,689 B2 | 8/2015 | Robertson et al. |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0014087 A1 | 1/2003 | Fang et al. |
| 2003/0036705 A1 | 2/2003 | Hare et al. |

(56) References Cited

U.S. PATENT DOCUMENTS

| | | |
|---|---|---|
| 2003/0050572 A1 | 3/2003 | Brautigam et al. |
| 2003/0055443 A1 | 3/2003 | Spotnitz |
| 2003/0114851 A1 | 6/2003 | Truckai et al. |
| 2003/0144680 A1 | 7/2003 | Kellogg et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0132383 A1 | 7/2004 | Langford et al. |
| 2004/0147934 A1 | 7/2004 | Kiester |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0199193 A1 | 10/2004 | Hayashi et al. |
| 2004/0204728 A1 | 10/2004 | Haefner |
| 2004/0243147 A1 | 12/2004 | Lipow |
| 2004/0260300 A1 | 12/2004 | Gorensek et al. |
| 2005/0021018 A1 | 1/2005 | Anderson et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0099824 A1 | 5/2005 | Dowling et al. |
| 2005/0103819 A1 | 5/2005 | Racenet et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0209620 A1 | 9/2005 | Du et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0066181 A1 | 3/2006 | Bromfield et al. |
| 2006/0074442 A1 | 4/2006 | Noriega et al. |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0235306 A1 | 10/2006 | Cotter et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0271030 A1 | 11/2006 | Francis et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0074584 A1 | 4/2007 | Talarico et al. |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0185380 A1 | 8/2007 | Kucklick |
| 2007/0191712 A1 | 8/2007 | Messerly et al. |
| 2007/0219481 A1 | 9/2007 | Babaev |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0013809 A1 | 1/2008 | Zhu et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0114364 A1 | 5/2008 | Goldin et al. |
| 2008/0125768 A1 | 5/2008 | Tahara et al. |
| 2008/0140158 A1 | 6/2008 | Hamel et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287948 A1 | 11/2008 | Newton et al. |
| 2009/0023985 A1 | 1/2009 | Ewers |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0112229 A1 | 4/2009 | Omori et al. |
| 2009/0118751 A1 | 5/2009 | Wiener et al. |
| 2009/0118802 A1 | 5/2009 | Mioduski et al. |
| 2009/0138006 A1 | 5/2009 | Bales et al. |
| 2009/0143799 A1 | 6/2009 | Smith et al. |
| 2009/0143800 A1 | 6/2009 | Deville et al. |
| 2009/0143806 A1 | 6/2009 | Witt et al. |
| 2009/0149801 A1 | 6/2009 | Crandall et al. |
| 2009/0207923 A1 | 8/2009 | Dress |
| 2009/0216157 A1 | 8/2009 | Yamada |
| 2009/0223033 A1 | 9/2009 | Houser |
| 2009/0254077 A1 | 10/2009 | Craig |
| 2009/0254080 A1 | 10/2009 | Honda |

(56) References Cited

U.S. PATENT DOCUMENTS

| | | |
|---|---|---|
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270899 A1 | 10/2009 | Carusillo et al. |
| 2009/0275940 A1 | 11/2009 | Malackowski et al. |
| 2009/0318945 A1 | 12/2009 | Yoshimine et al. |
| 2009/0327715 A1 | 12/2009 | Smith et al. |
| 2010/0004508 A1 | 1/2010 | Naito et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0036370 A1 | 2/2010 | Mirel et al. |
| 2010/0042077 A1 | 2/2010 | Okada |
| 2010/0049180 A1 | 2/2010 | Wells et al. |
| 2010/0063525 A1 | 3/2010 | Beaupre et al. |
| 2010/0063528 A1 | 3/2010 | Beaupré |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0222714 A1 | 9/2010 | Muir et al. |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nield |
| 2010/0331742 A1 | 12/2010 | Masuda |
| 2011/0004233 A1 | 1/2011 | Muir et al. |
| 2011/0009850 A1 | 1/2011 | Main et al. |
| 2011/0015631 A1 | 1/2011 | Wiener et al. |
| 2011/0077648 A1 | 3/2011 | Lee et al. |
| 2011/0087218 A1 | 4/2011 | Boudreaux et al. |
| 2011/0112526 A1 | 5/2011 | Fritz et al. |
| 2011/0125151 A1 | 5/2011 | Strauss et al. |
| 2011/0125174 A1 | 5/2011 | Babaev |
| 2011/0144806 A1 | 6/2011 | Sandhu et al. |
| 2011/0196399 A1 | 8/2011 | Robertson et al. |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0290853 A1 | 12/2011 | Shelton, IV et al. |
| 2011/0290856 A1 | 12/2011 | Shelton, IV et al. |
| 2012/0004655 A1 | 1/2012 | Kim et al. |
| 2012/0022525 A1 | 1/2012 | Dietz et al. |
| 2012/0022530 A1 | 1/2012 | Woodruff et al. |
| 2012/0022583 A1 | 1/2012 | Sugalski et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0101495 A1 | 4/2012 | Young et al. |
| 2012/0109159 A1 | 5/2012 | Jordan et al. |
| 2012/0116379 A1 | 5/2012 | Yates et al. |
| 2012/0116391 A1 | 5/2012 | Houser et al. |
| 2012/0116394 A1 | 5/2012 | Timm et al. |
| 2012/0116395 A1 | 5/2012 | Madan et al. |
| 2012/0130256 A1 | 5/2012 | Buysse et al. |
| 2012/0130365 A1 | 5/2012 | McLawhorn |
| 2012/0136354 A1 | 5/2012 | Rupp |
| 2012/0138660 A1 | 6/2012 | Shelton, IV |
| 2012/0143211 A1 | 6/2012 | Kishi |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203143 A1 | 8/2012 | Sanai et al. |
| 2012/0203247 A1 | 8/2012 | Shelton, IV et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0215220 A1 | 8/2012 | Manzo et al. |
| 2012/0245582 A1 | 9/2012 | Kimball et al. |
| 2012/0253370 A1 | 10/2012 | Ross et al. |
| 2012/0265196 A1 | 10/2012 | Turner et al. |
| 2012/0269676 A1 | 10/2012 | Houser et al. |
| 2012/0330307 A1 | 12/2012 | Ladtkow et al. |
| 2013/0012957 A1 | 1/2013 | Shelton, IV et al. |
| 2013/0030433 A1 | 1/2013 | Heard |
| 2013/0035680 A1 | 2/2013 | Ben-Haim et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0165929 A1 | 6/2013 | Muir et al. |
| 2013/0211397 A1 | 8/2013 | Parihar et al. |
| 2013/0217967 A1 | 8/2013 | Mohr et al. |
| 2013/0226207 A1 | 8/2013 | Stulen et al. |
| 2013/0226208 A1 | 8/2013 | Wiener et al. |
| 2013/0245659 A1 | 9/2013 | Robertson et al. |
| 2013/0267975 A1 | 10/2013 | Timm et al. |
| 2013/0274734 A1 | 10/2013 | Maass et al. |
| 2013/0282003 A1 | 10/2013 | Messerly et al. |
| 2013/0282038 A1 | 10/2013 | Dannaher et al. |
| 2013/0282039 A1 | 10/2013 | Wiener et al. |
| 2013/0285758 A1 | 10/2013 | Aldridge et al. |
| 2013/0289591 A1 | 10/2013 | Boudreaux et al. |
| 2013/0296908 A1 | 11/2013 | Schulte et al. |
| 2013/0338661 A1 | 12/2013 | Behnke, II |
| 2013/0345689 A1 | 12/2013 | Ruddenklau et al. |
| 2014/0005640 A1 | 1/2014 | Shelton, IV et al. |
| 2014/0005653 A1 | 1/2014 | Shelton, IV et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005667 A1 | 1/2014 | Stulen et al. |
| 2014/0005668 A1 | 1/2014 | Rhee et al. |
| 2014/0005676 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005682 A1 | 1/2014 | Worrell et al. |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005704 A1 | 1/2014 | Vakharia et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0012299 A1 | 1/2014 | Stoddard et al. |
| 2014/0066962 A1 | 3/2014 | Robertson et al. |
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0135804 A1 | 5/2014 | Weisenburgh, II et al. |
| 2014/0155921 A1 | 6/2014 | Price et al. |
| 2014/0180280 A1 | 6/2014 | Sigmon, Jr. |
| 2014/0243864 A1 | 8/2014 | Voegele et al. |
| 2014/0276738 A1 | 9/2014 | Price et al. |
| 2014/0276970 A1 | 9/2014 | Messerly et al. |
| 2014/0336686 A1 | 11/2014 | Houser et al. |
| 2015/0045819 A1 | 2/2015 | Houser et al. |
| 2015/0066067 A1 | 3/2015 | Stulen |
| 2015/0073460 A1 | 3/2015 | Stulen |

(56) References Cited

U.S. PATENT DOCUMENTS

| | | |
|---|---|---|
| 2015/0112335 A1 | 4/2015 | Boudreaux et al. |
| 2015/0119914 A1 | 4/2015 | Neurohr et al. |
| 2015/0119915 A1 | 4/2015 | Neurohr et al. |
| 2015/0119916 A1 | 4/2015 | Dietz et al. |
| 2015/0123348 A1 | 5/2015 | Robertson et al. |
| 2015/0157355 A1 | 6/2015 | Price et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |
| 2015/0196318 A1 | 7/2015 | Messerly et al. |

FOREIGN PATENT DOCUMENTS

| | | |
|---|---|---|
| CN | 1640365 A | 7/2005 |
| CN | 1694649 A | 11/2005 |
| CN | 1922563 A | 2/2007 |
| CN | 1951333 A | 4/2007 |
| CN | 101040799 A | 9/2007 |
| CN | 101467917 A | 1/2009 |
| DE | 3904558 A1 | 8/1990 |
| DE | 9210327 U1 | 11/1992 |
| DE | 4323585 A1 | 1/1995 |
| DE | 19608716 C1 | 4/1997 |
| DE | 20021619 U1 | 3/2001 |
| DE | 10042606 A1 | 8/2001 |
| EP | 0136855 B1 | 9/1984 |
| EP | 0171967 A2 | 2/1986 |
| EP | 1839599 A1 | 10/1987 |
| EP | 0336742 A2 | 4/1989 |
| EP | 0342448 A1 | 11/1989 |
| EP | 0424685 B1 | 5/1991 |
| EP | 0443256 A1 | 8/1991 |
| EP | 0456470 A1 | 11/1991 |
| EP | 0598976 A2 | 1/1994 |
| EP | 0677275 A2 | 3/1995 |
| EP | 0482195 B1 | 1/1996 |
| EP | 0695535 A1 | 2/1996 |
| EP | 0741996 A2 | 11/1996 |
| EP | 0612570 B1 | 6/1997 |
| EP | 1108394 A2 | 6/2001 |
| EP | 0908148 B1 | 1/2002 |
| EP | 1229515 A2 | 8/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1433425 B1 | 6/2006 |
| EP | 1256323 B1 | 9/2006 |
| EP | 1698289 A2 | 9/2006 |
| EP | 1704824 A1 | 9/2006 |
| EP | 1749479 A1 | 2/2007 |
| EP | 1815950 A1 | 8/2007 |
| EP | 1844720 A1 | 10/2007 |
| EP | 1862133 A1 | 12/2007 |
| EP | 1875875 A1 | 1/2008 |
| EP | 1199045 B1 | 6/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1997438 A2 | 12/2008 |
| EP | 1477104 B1 | 1/2009 |
| EP | 2014218 A2 | 1/2009 |
| EP | 2042112 A2 | 4/2009 |
| EP | 1832259 B1 | 6/2009 |
| EP | 2074959 A1 | 7/2009 |
| EP | 2106758 A1 | 10/2009 |
| EP | 2111813 A1 | 10/2009 |
| EP | 2200145 A1 | 6/2010 |
| EP | 1214913 B1 | 7/2010 |
| EP | 2238938 A1 | 10/2010 |
| EP | 2298154 A2 | 3/2011 |
| EP | 1510178 B1 | 6/2011 |
| EP | 2305144 A1 | 6/2011 |
| EP | 2335630 A1 | 6/2011 |
| EP | 1502551 B1 | 7/2011 |
| EP | 2361562 A1 | 8/2011 |
| EP | 2365608 A2 | 9/2011 |
| EP | 2422721 A2 | 2/2012 |
| EP | 1927321 B1 | 4/2012 |
| EP | 2510891 A1 | 10/2012 |
| EP | 2316359 B1 | 3/2013 |
| EP | 1586275 B1 | 5/2013 |
| EP | 1616529 B1 | 9/2013 |
| EP | 2583633 B1 | 10/2014 |
| GB | 1482943 A | 8/1977 |
| GB | 2032221 A | 4/1980 |
| GB | 2379878 B | 11/2004 |
| GB | 2447767 B | 8/2011 |
| JP | S 50-100891 | 12/1973 |
| JP | S 59-68513 | 10/1982 |
| JP | S 59141938 A | 8/1984 |
| JP | 62-221343 A | 9/1987 |
| JP | S 62-227343 | 10/1987 |
| JP | 62-292153 A | 12/1987 |
| JP | S 62-292154 A | 12/1987 |
| JP | 63-109386 A | 5/1988 |
| JP | 63-315049 A | 12/1988 |
| JP | H 01-151452 | 6/1989 |
| JP | H 01-198540 A | 8/1989 |
| JP | 02-71510 U | 5/1990 |
| JP | 2-286149 A | 11/1990 |
| JP | H 02-292193 A | 12/1990 |
| JP | H 03-37061 A | 2/1991 |
| JP | 04-25707 U | 2/1992 |
| JP | H 04-64351 A | 2/1992 |
| JP | 4-30508 U | 3/1992 |
| JP | H 04-150847 A | 5/1992 |
| JP | H 04-152942 A | 5/1992 |
| JP | 05-095955 A | 4/1993 |
| JP | H 05-115490 A | 5/1993 |
| JP | H 06-070938 A | 3/1994 |
| JP | 6-104503 A | 4/1994 |
| JP | 6-507081 A | 8/1994 |
| JP | H 06-217988 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 08-299351 A | 11/1996 |
| JP | H 08-336545 A | 12/1996 |
| JP | H 09-503146 A | 3/1997 |
| JP | H 09-135553 A | 5/1997 |
| JP | H 09-140722 A | 6/1997 |
| JP | H 10-005237 A | 1/1998 |
| JP | 10-295700 A | 11/1998 |
| JP | H 11-501543 A | 2/1999 |
| JP | H 11-128238 A | 5/1999 |
| JP | H 11-192235 A | 7/1999 |
| JP | 11-253451 A | 9/1999 |
| JP | H 11-318918 A | 11/1999 |
| JP | 2000-041991 | 2/2000 |
| JP | 2000-070279 A | 3/2000 |
| JP | 2000-210299 A | 8/2000 |
| JP | 2000-287987 A | 10/2000 |
| JP | 2001-029353 A | 2/2001 |
| JP | 2001-502216 A | 2/2001 |
| JP | 2003612 A | 6/2001 |

(56) References Cited

FOREIGN PATENT DOCUMENTS

| | | |
|---|---|---|
| JP | 2001-309925 A | 11/2001 |
| JP | 2002-186901 A | 7/2002 |
| JP | 2002-204808 A | 7/2002 |
| JP | 2002-263579 A | 9/2002 |
| JP | 2002-301086 A | 10/2002 |
| JP | 2002-330977 A | 11/2002 |
| JP | 2002-542690 A | 12/2002 |
| JP | 2003-000612 A | 1/2003 |
| JP | 2003-010201 | 1/2003 |
| JP | 2003-510158 A | 3/2003 |
| JP | 2003-116870 A | 4/2003 |
| JP | 2003-126110 A | 5/2003 |
| JP | 2003-310627 A | 5/2003 |
| JP | 2003-530921 A | 10/2003 |
| JP | 2003-339730 A | 12/2003 |
| JP | 2004-147701 A | 5/2004 |
| JP | 2005027026 A | 1/2005 |
| JP | 2005-040222 A | 2/2005 |
| JP | 2005-066316 A | 3/2005 |
| JP | 2005-074088 A | 3/2005 |
| JP | 2005-534451 A | 11/2005 |
| JP | 2006-6410 A | 1/2006 |
| JP | 2006-512149 A | 4/2006 |
| JP | 2006-116194 A | 5/2006 |
| JP | 2006-158525 A | 6/2006 |
| JP | 2006-218296 A | 8/2006 |
| JP | 2006217716 A | 8/2006 |
| JP | 2006-288431 A | 10/2006 |
| JP | 2007-050181 A | 3/2007 |
| JP | 2003-126104 A | 5/2007 |
| JP | 2007-229454 A | 9/2007 |
| JP | 2007-527747 A | 10/2007 |
| JP | 2008-508065 A | 3/2008 |
| JP | 2008-119250 A | 5/2008 |
| JP | 2008-521503 A | 6/2008 |
| JP | 2008-212679 A | 9/2008 |
| JP | 2008-536562 A | 9/2008 |
| JP | 2008-284374 | 11/2008 |
| JP | 2009-511206 A | 3/2009 |
| JP | 2009-517181 A | 4/2009 |
| JP | 4262923 B2 | 5/2009 |
| JP | 2009-523567 A | 6/2009 |
| JP | 2009-236177 | 10/2009 |
| JP | 2009-254819 A | 11/2009 |
| JP | 2010-000336 A | 1/2010 |
| JP | 2010-514923 A | 5/2010 |
| JP | 2010-534522 A | 11/2010 |
| JP | 2010-540186 A | 12/2010 |
| JP | 2011-505198 A | 2/2011 |
| JP | 2012-235658 A | 11/2012 |
| JP | 5208761 B2 | 6/2013 |
| WO | WO 92/22259 A2 | 12/1992 |
| WO | WO 93/08757 A1 | 5/1993 |
| WO | WO 93/14708 A1 | 8/1993 |
| WO | WO 93/16646 A1 | 9/1993 |
| WO | WO 93/20877 A1 | 10/1993 |
| WO | WO 94/21183 A1 | 9/1994 |
| WO | WO 94/24949 A1 | 11/1994 |
| WO | WO 95/09572 A1 | 4/1995 |
| WO | WO 96/30885 A1 | 10/1996 |
| WO | WO 96/39086 A1 | 12/1996 |
| WO | WO 98/16156 A1 | 4/1998 |
| WO | WO 98/26739 A1 | 6/1998 |
| WO | WO 98/35621 A1 | 8/1998 |
| WO | WO 98/37815 A1 | 9/1998 |
| WO | WO 99/20213 A1 | 4/1999 |
| WO | WO 99/52489 A1 | 10/1999 |
| WO | WO 00/64358 A2 | 11/2000 |
| WO | WO 00/74585 A2 | 12/2000 |
| WO | WO 01/54590 A1 | 8/2001 |
| WO | WO 01/67970 A1 | 9/2001 |
| WO | WO 01/95810 A2 | 12/2001 |
| WO | WO 02/24080 A2 | 3/2002 |
| WO | WO 02/38057 A1 | 5/2002 |
| WO | WO 02/062241 A1 | 8/2002 |
| WO | WO 03/082133 A1 | 10/2003 |
| WO | WO 2004/012615 A1 | 2/2004 |
| WO | WO 2004/026104 A2 | 4/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/098426 A1 | 11/2004 |
| WO | WO 2004/112618 A2 | 12/2004 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/119139 A2 | 11/2006 |
| WO | WO 2006/119376 A2 | 11/2006 |
| WO | WO 2006/129465 A1 | 12/2006 |
| WO | WO 2007/008703 A2 | 1/2007 |
| WO | WO 2007/008710 A2 | 1/2007 |
| WO | WO 2007/040818 A1 | 4/2007 |
| WO | WO 2007/047380 A2 | 4/2007 |
| WO | WO 2007/047531 A2 | 4/2007 |
| WO | WO 2007/056590 A1 | 5/2007 |
| WO | WO 2007/087272 A2 | 8/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/051764 A2 | 5/2008 |
| WO | WO 2008/089174 A2 | 7/2008 |
| WO | WO 2008/118709 A1 | 10/2008 |
| WO | WO 2008/130793 A1 | 10/2008 |
| WO | WO 2009/018067 A1 | 2/2009 |
| WO | WO 2009/018406 A2 | 2/2009 |
| WO | WO 2009/027065 A1 | 3/2009 |
| WO | WO 2009/046234 A2 | 4/2009 |
| WO | WO 2009/073402 A2 | 6/2009 |
| WO | WO 2009/120992 A2 | 10/2009 |
| WO | WO 2010/068783 A1 | 6/2010 |
| WO | WO 2011/008672 A2 | 1/2011 |
| WO | WO 2011/052939 A2 | 5/2011 |
| WO | WO 2011/100321 A2 | 8/2011 |
| WO | WO 2011/144911 A1 | 11/2011 |
| WO | WO 2012/061722 A2 | 5/2012 |
| WO | WO 2012/128362 A1 | 9/2012 |
| WO | WO 2012/135705 A1 | 10/2012 |
| WO | WO 2012/135721 A1 | 10/2012 |
| WO | WO 2013/018934 A1 | 2/2013 |
| WO | WO 2013/062978 A2 | 5/2013 |

OTHER PUBLICATIONS

Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., "Fundamentals of Heat and Mass Transfer", Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

(56) References Cited

OTHER PUBLICATIONS

Campbell et al, "Thermal Imaging in Surgery," p. 19-3, in *Medical Infrared Imaging*, N. A. Diakides and J. D. Bronzino, Eds. (2008).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
http://www.apicalinstr.com/generators.htm.
http://www.dotmed.com/listing/electrosurical-unit/ethicon/ultracision-g110-/1466724.
http://www.ethicon.com/gb-en/healthcare-professionals/products/energy-devices/capital//ge . . . .
http://www.4-traders.com/JOHNSON-JOHNSON-4832/news/Johnson-Johnson-Ethicon-E . . . .
http://www.medicalexpo.com/medical-manufacturer/electrosurgical-generator-6951.html.
http://www.megadyne.com/es_generator.php.
http://www.valleylab.com/product/es/generators/index.html.
Covidien 501(k) Summary Sonicision, dated Feb. 24, 2011 (7 pages).
Gerhard, Glen C., "Surgical Electrotechnology: Quo Vadis?," Biomedical Engineering, IEEE Transactions on , vol. BME-31, No. 12, pp. 787, 792, Dec. 1984.
Fowler, K.R., "A programmable, arbitrary waveform electrosurgical device," Engineering in Medicine and Biology Society, 1988. Proceedings of the Annual International Conference of the IEEE, vol., No., pp. 1324, 1325 vol. 3, Nov. 4-7, 1988.
LaCourse, J.R.; Vogt, M.C.; Miller, W.T., III; Selikowitz, S.M., "Spectral analysis interpretation of electro-surgical generator nerve and muscle stimulation," Biomedical Engineering, IEEE Transactions on , vol. 35, No. 7, pp. 505, 509, Jul. 1988.
U.S. Appl. No. 13/751,680, filed Jan. 28, 2013.

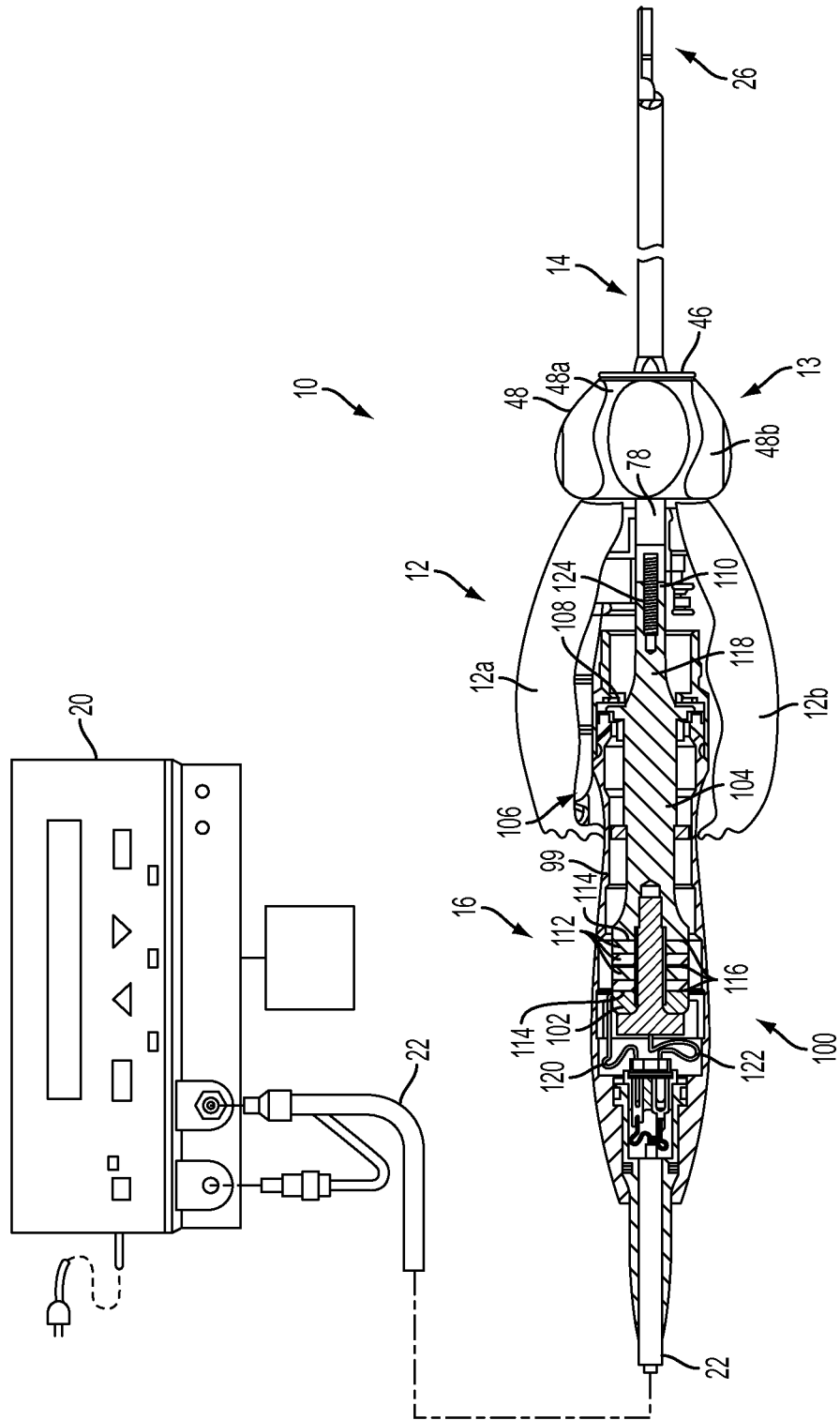

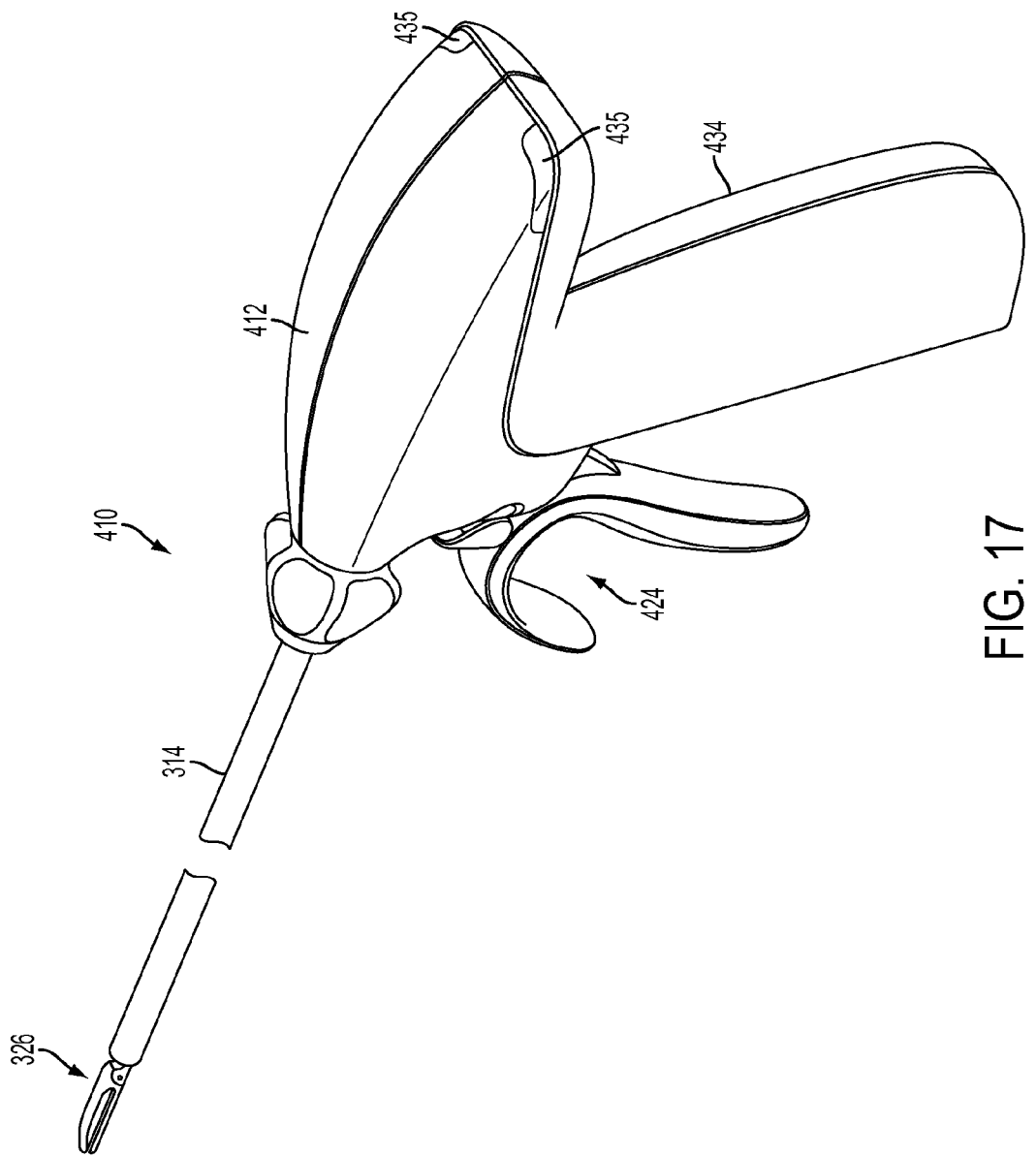

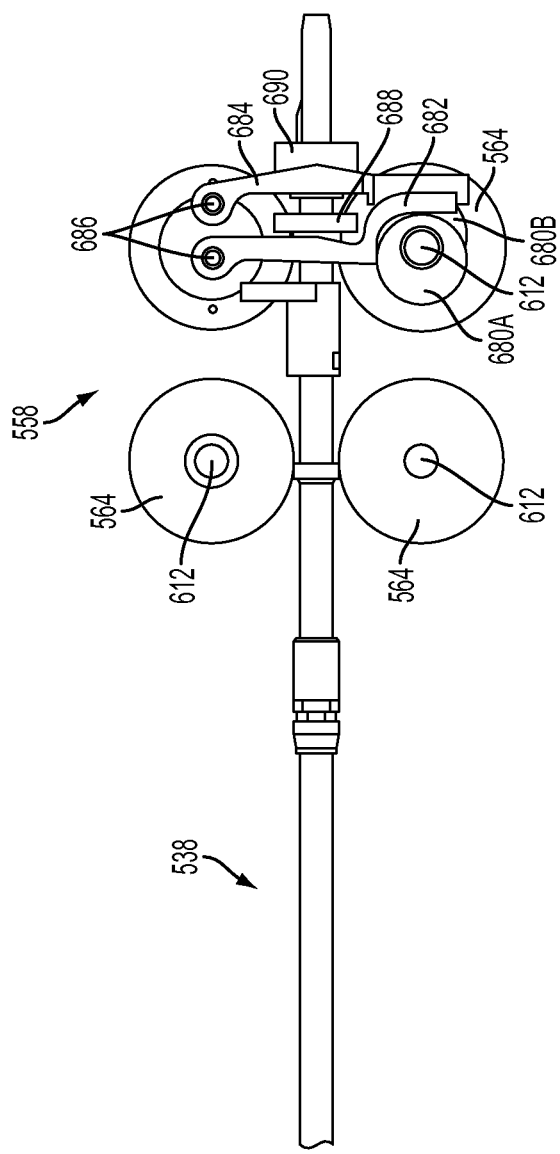

_US 9,326,788 B2_

LOCKOUT MECHANISM FOR USE WITH ROBOTIC ELECTROSURGICAL DEVICE

CROSS-REFERENCE TO RELATED APPLICATIONS

The present application is related to the following, concurrently-filed U.S. patent applications, which are incorporated herein by reference in their entirety:

U.S. application Ser. No. 13/539,096, entitled "Haptic Feedback Devices for Surgical Robot,";

U.S. application Ser. No. 13/539,117, entitled "Closed Feedback Control for Electrosurgical Device,";

U.S. application Ser. No. 13/538,588, entitled "Surgical Instruments with Articulating Shafts,";

U.S. application Ser. No. 13/538,601, entitled "Ultrasonic Surgical Instruments with Distally Positioned Transducers,";

U.S. application Ser. No. 13/538,700, entitled "Surgical Instruments with Articulating Shafts,";

U.S. application Ser. No. 13/538,711, entitled "Ultrasonic Surgical Instruments with Distally Positioned Jaw Assemblies,";

U.S. application Ser. No. 13/538,720, entitled "Surgical Instruments with Articulating Shafts,";

U.S. application Ser. No. 13/538,733, entitled "Ultrasonic Surgical Instruments with Control Mechanisms,"; and U.S. application Ser. No. 13/539,122,entitled "Surgical Instruments with Fluid Management System,".

BACKGROUND

The present disclosure relates generally to the field of robotic surgery. In particular, the present disclosure relates to, although not exclusively, robotically controlled surgical instruments. More particularly, the present disclosure relates to, although not exclusively, lockout mechanism for use with electrosurgical and ultrasonic robotic surgical instruments.

Ultrasonic surgical devices, such as ultrasonic scalpels, are used in many applications in surgical procedures by virtue of their unique performance characteristics. Depending upon specific device configurations and operational parameters, ultrasonic surgical devices can provide substantially simultaneous transection of tissue and homeostasis by coagulation, desirably minimizing patient trauma. An ultrasonic surgical device comprises a proximally-positioned ultrasonic transducer and an instrument coupled to the ultrasonic transducer having a distally-mounted end effector comprising an ultrasonic blade to cut and seal tissue. The end effector is typically coupled either to a handle and/or a robotic surgical implement via a shaft. The blade is acoustically coupled to the transducer via a waveguide extending through the shaft. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures. Vibrating at high frequencies (e.g., 55,500 times per second), the ultrasonic blade denatures protein in the tissue to form a sticky coagulum. Pressure exerted on tissue by the blade surface collapses blood vessels and allows the coagulum to form a haemostatic seal. A surgeon can control the cutting speed and coagulation by the force applied to the tissue by the end effector, the time over which the force is applied and the selected excursion level of the end effector.

Also used in many surgical applications are electrosurgical devices. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrical energy applied by an electrosurgical device can be transmitted to the instrument by a generator. The electrical energy may be in the form of radio frequency ("RF") energy. RF energy is a form of electrical energy that may be in the frequency range of 300 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

In many cases, it is desirable to prevent a cutting member from moving prior to the application of electrosurgical or ultrasonic energy to the blade element. In a robotic surgical system, a surgeon is typically not in the room with the patient and is unable to visually verify that energy has been applied to surgical instrument prior to activating the cutting member. It would be desirable to provide a mechanism for robotic surgical systems to prevent actuation of a cutting member prior to the application of electrosurgical or ultrasonic energy.

SUMMARY

In one embodiment, a robotically controlled surgical tool comprising including a lockout mechanism is provided. The surgical tool may comprise an instrument mounting portion. The instrument mounting portion includes a housing, a plate, a shaft assembly comprising an end effector, and a coupler to couple the shaft assembly to the instrument mounting portion. The end effector comprises a first jaw member and a second jaw member, the first and second jaw members defining a channel therebetween, and a blade slideably receivable within the channel to cut tissue located between the first and second jaw members. The surgical tool may include an actuation mechanism to actuate the end effector to provide reciprocating movement of the blade within the channel. A lockout mechanism is coupled to the actuation mechanism. The lockout mechanism may selectively enable reciprocating movement of the blade. An interface mechanically and electrically couples the instrument mounting portion to a robotic manipulator.

BRIEF DESCRIPTION OF THE FIGURES

The features of the various embodiments are set forth with particularity in the appended claims. The various embodiments, however, both as to organization and methods of operation, together with advantages thereof, may best be understood by reference to the following description, taken in conjunction with the accompanying drawings as follows:

FIG. 8 illustrates a top view of one embodiment of a surgical system including a surgical instrument and an ultrasonic generator.

FIG. 17 illustrates a section a perspective view of one embodiment of a cordless electrical energy surgical instrument.

FIGS. 43-46A illustrate an alternate embodiment of the instrument mounting portion showing an alternate example mechanism for differential translation of members along the axis of the shaft (e.g., for articulation).

DESCRIPTION

Various example embodiments are directed to a control system for a robotic surgical system.

Various embodiments of surgical instruments and robotic surgical systems are described herein. It will be understood by those skilled in the art that the various embodiments of the surgical tool lockout mechanism may be used with the described surgical instruments and robotic surgical systems. The descriptions are provided for example only, and those skilled in the art will understand that the disclosed surgical tool lockout mechanism is not limited to only the devices disclosed herein, but may be used with any compatible surgical instrument or robotic surgical system.

Reference will now be made in detail to several embodiments, including embodiments showing example implementations of robotic surgical instruments with end effectors comprising ultrasonic and/or electrosurgical elements. Wherever practicable similar or like reference numbers may be used in the figures and may indicate similar or like functionality. The figures depict example embodiments of the methods of use for purposes of illustration only. One skilled in the art will readily recognize from the following description that alternative example embodiments of the structures and methods illustrated herein may be employed without departing from the principles described herein.

Figure 1:
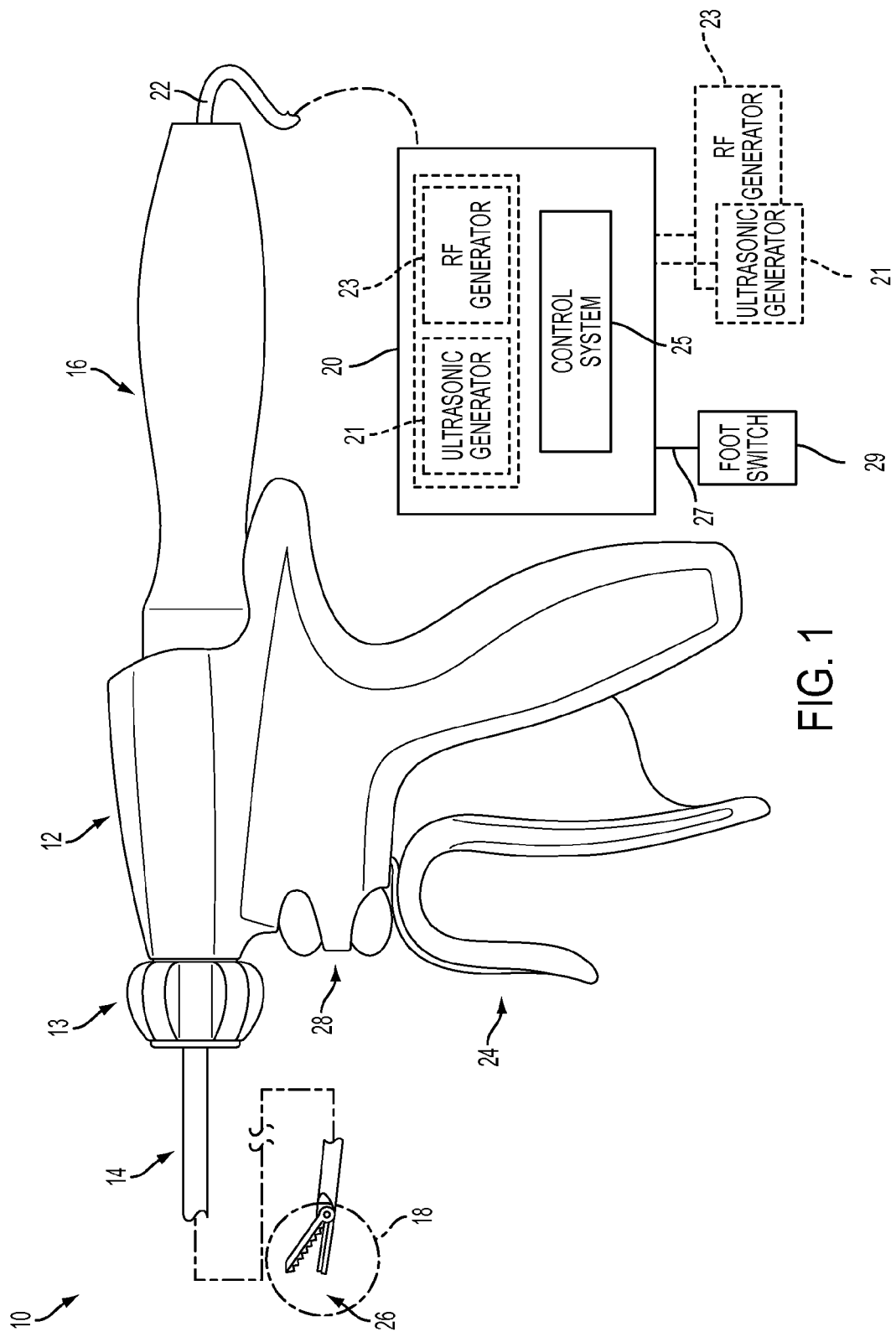
FIG. 1 illustrates one embodiment of a surgical system including a surgical instrument and an ultrasonic generator.

FIG. 1 is a right side view of one embodiment of an ultrasonic surgical instrument 10. In the illustrated embodiment, the ultrasonic surgical instrument 10 may be employed in various surgical procedures including endoscopic or traditional open surgical procedures. In one example embodiment, the ultrasonic surgical instrument 10 comprises a handle assembly 12, an elongated shaft assembly 14, and an ultrasonic transducer 16. The handle assembly 12 comprises a trigger assembly 24, a distal rotation assembly 13, and a switch assembly 28. The elongated shaft assembly 14 comprises an end effector assembly 26, which comprises elements to dissect tissue or mutually grasp, cut, and coagulate vessels and/or tissue, and actuating elements to actuate the end effector assembly 26. The handle assembly 12 is adapted to receive the ultrasonic transducer 16 at the proximal end. The ultrasonic transducer 16 is mechanically engaged to the elongated shaft assembly 14 and portions of the end effector assembly 26. The ultrasonic transducer 16 is electrically coupled to a generator 20 via a cable 22. Although the majority of the drawings depict a multiple end effector assembly 26 for use in connection with laparoscopic surgical procedures, the ultrasonic surgical instrument 10 may be employed in more traditional open surgical procedures and in other embodiments, and may be configured for use in endoscopic procedures. For the purposes herein, the ultrasonic surgical instrument 10 is described in terms of an endoscopic instrument; however, it is contemplated that an open and/or laparoscopic version of the ultrasonic surgical instrument 10 also may include the same or similar operating components and features as described herein.

Figure 18A:
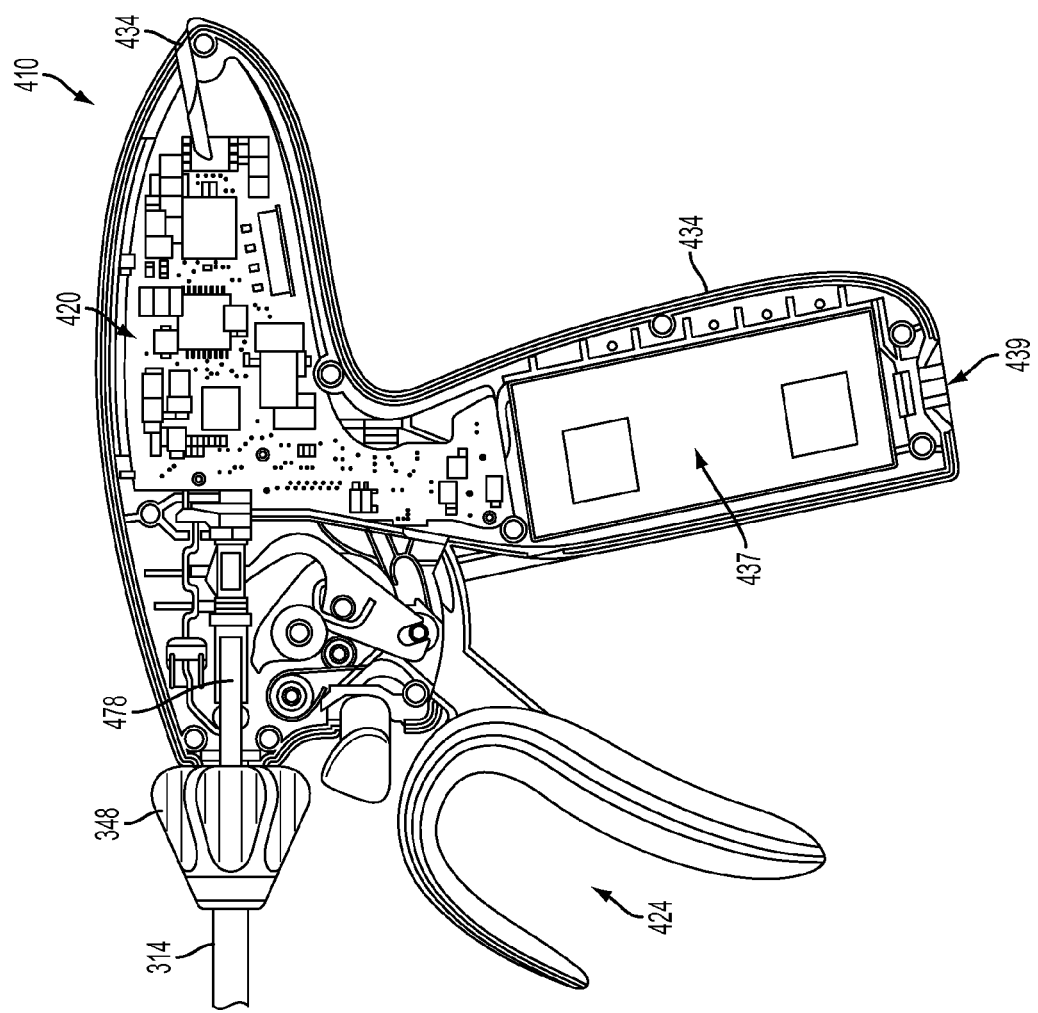
FIG. 18A illustrates a side view of a handle of one embodiment of the surgical instrument of FIG. 17 with a half handle body removed to illustrate various components therein.

In various embodiments, the generator 20 comprises several functional elements, such as modules and/or blocks. Different functional elements or modules may be configured for driving different kinds of surgical devices. For example, an ultrasonic generator module 21 may drive an ultrasonic device, such as the ultrasonic surgical instrument 10. In some example embodiments, the generator 20 also comprises an electrosurgery/RF generator module 23 for driving an electrosurgical device (or an electrosurgical embodiment of the ultrasonic surgical instrument 10). In various embodiments, the generator 20 may be formed integrally within the handle assembly 12. In such implementations, a battery would be co-located within the handle assembly 12 to act as the energy source. FIG. 18A and accompanying disclosures provide one example of such implementations.

In some embodiments, the electrosurgery/RF generator module 23 may be configured to generate a therapeutic and/or a sub-therapeutic energy level. In the example embodiment illustrated in FIG. 1, the generator 20 includes a control system 25 integral with the generator 20 and a foot switch 29 connected to the generator via a cable 27. The generator 20 may also comprise a triggering mechanism for activating a surgical instrument, such as the instrument 10. The triggering mechanism may include a power switch (not shown) as well as a foot switch 29. When activated by the foot switch 29, the generator 20 may provide energy to drive the acoustic assembly of the surgical instrument 10 and to drive the end effector 18 at a predetermined excursion level. The generator 20 drives or excites the acoustic assembly at any suitable resonant frequency of the acoustic assembly and/or derives the therapeutic/sub-therapeutic electromagnetic/RF energy.

In one embodiment, the electrosurgical/RF generator module 23 may be implemented as an electrosurgery unit (ESU) capable of supplying power sufficient to perform bipolar electrosurgery using radio frequency (RF) energy. In one embodiment, the ESU can be a bipolar ERBE ICC 350 sold by ERBE USA, Inc. of Marietta, Ga. In bipolar electrosurgery applications, as previously discussed, a surgical instrument having an active electrode and a return electrode can be utilized, wherein the active electrode and the return electrode can be positioned against, or adjacent to, the tissue to be treated such that current can flow from the active electrode to the return electrode through the tissue. Accordingly, the electrosurgical/RF module 23 generator may be configured for therapeutic purposes by applying electrical energy to the tissue T sufficient for treating the tissue (e.g., cauterization).

In one embodiment, the electrosurgical/RF generator module 23 may be configured to deliver a sub-therapeutic RF signal to implement a tissue impedance measurement module. In one embodiment, the electrosurgical/RF generator module 23 comprises a bipolar radio frequency generator as described in more detail below. In one embodiment, the electrosurgical/RF generator module 12 may be configured to monitor electrical impedance Z, of tissue T and to control the characteristics of time and power level based on the tissue T by way of a return electrode on provided on a clamp member of the end effector assembly 26. Accordingly, the electrosurgical/RF generator module 23 may be configured for sub-therapeutic purposes for measuring the impedance or other electrical characteristics of the tissue T. Techniques and circuit configurations for measuring the impedance or other electrical characteristics of tissue T are discussed in more detail in commonly assigned U.S. Patent Publication No. 2011/0015631, titled "Electrosurgical Generator for Ultrasonic Surgical Instruments," the disclosure of which is herein incorporated by reference in its entirety.

A suitable ultrasonic generator module 21 may be configured to functionally operate in a manner similar to the GEN300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,899 (Method for Detecting Transverse Vibrations in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

It will be appreciated that in various embodiments, the generator 20 may be configured to operate in several modes. In one mode, the generator 20 may be configured such that the ultrasonic generator module 21 and the electrosurgical/RF generator module 23 may be operated independently. One example of the independent operations of the ultrasonic generator module 21 and the electrosurgical/RF generator module 23 from the generator 20 is shown if FIG. 1, with the modules 21 and 23 optionally placed outside of and coupled to the generator 20.

For example, the ultrasonic generator module 21 may be activated to apply ultrasonic energy to the end effector assembly 26 and subsequently, either therapeutic sub-therapeutic RF energy may be applied to the end effector assembly 26 by the electrosurgical/RF generator module 23. As previously discussed, the sub-therapeutic electrosurgical/RF energy may be applied to tissue clamped between claim elements of the end effector assembly 26 to measure tissue impedance to control the activation, or modify the activation, of the ultrasonic generator module 21. Tissue impedance feedback from the application of the sub-therapeutic energy also may be employed to activate a therapeutic level of the electrosurgical/RF generator module 23 to seal the tissue (e.g., vessel) clamped between claim elements of the end effector assembly 26.

In another embodiment, the ultrasonic generator module 21 and the electrosurgical/RF generator module 23 may be activated simultaneously. In one example, the ultrasonic generator module 21 is simultaneously activated with a sub-therapeutic RF energy level to measure tissue impedance simultaneously while the ultrasonic blade of the end effector assembly 26 cuts and coagulates the tissue (or vessel) clamped between the clamp elements of the end effector assembly 26. Such feedback may be employed, for example, to modify the drive output of the ultrasonic generator module 21. In another example, the ultrasonic generator module 21 may be driven simultaneously with electrosurgical/RF generator module 23 such that the ultrasonic blade portion of the end effector assembly 26 is employed for cutting the damaged tissue while the electrosurgical/RF energy is applied to electrode portions of the end effector clamp assembly 26 for sealing the tissue (or vessel).

When the generator 20 is activated via the triggering mechanism, electrical energy is continuously applied by the generator 20 to a transducer stack or assembly of the acoustic assembly. A phase-locked loop in the control system of the generator 20 may monitor feedback from the acoustic assembly. In another embodiment, electrical energy is intermittently applied (e.g., pulsed) by the generator 20. The phase lock loop adjusts the frequency of the electrical energy sent by the generator 20 to match the resonant frequency of the selected longitudinal mode of vibration of the acoustic assembly. In addition, a second feedback loop in the control system 25 maintains the electrical current supplied to the acoustic assembly at a pre-selected constant level in order to achieve substantially constant excursion at the end effector 18 of the acoustic assembly. In yet another embodiment, a third feedback loop in the control system 25 monitors impedance between electrodes located in the end effector assembly 26. Although FIGS. 1-9 show a manually operated ultrasonic surgical instrument, it will be appreciated that ultrasonic surgical instruments may also be used in robotic applications, for example, as described herein, as well as combinations of manual robotic applications.

In ultrasonic operation mode, the electrical signal supplied to the acoustic assembly may cause the distal end of the end effector 18, to vibrate longitudinally in the range of, for example, approximately 20 kHz to 250 kHz. According to various embodiments, the blade 22 may vibrate in the range of about 54 kHz to 56 kHz, for example, at about 55.5 kHz. In other embodiments, the blade 22 may vibrate at other frequencies including, for example, about 31 kHz or about 80 kHz. The excursion of the vibrations at the blade can be controlled by, for example, controlling the amplitude of the electrical signal applied to the transducer assembly of the acoustic assembly by the generator 20. As noted above, the triggering mechanism of the generator 20 allows a user to activate the generator 20 so that electrical energy may be continuously or intermittently supplied to the acoustic assembly. The generator 20 also has a power line for insertion in an electro-surgical unit or conventional electrical outlet. It is contemplated that the generator 20 can also be powered by a direct current (DC) source, such as a battery. The generator 20 can comprise any suitable generator, such as Model No. GEN04, and/or Model No. GEN11 available from Ethicon Endo-Surgery, Inc.

Figure 2:
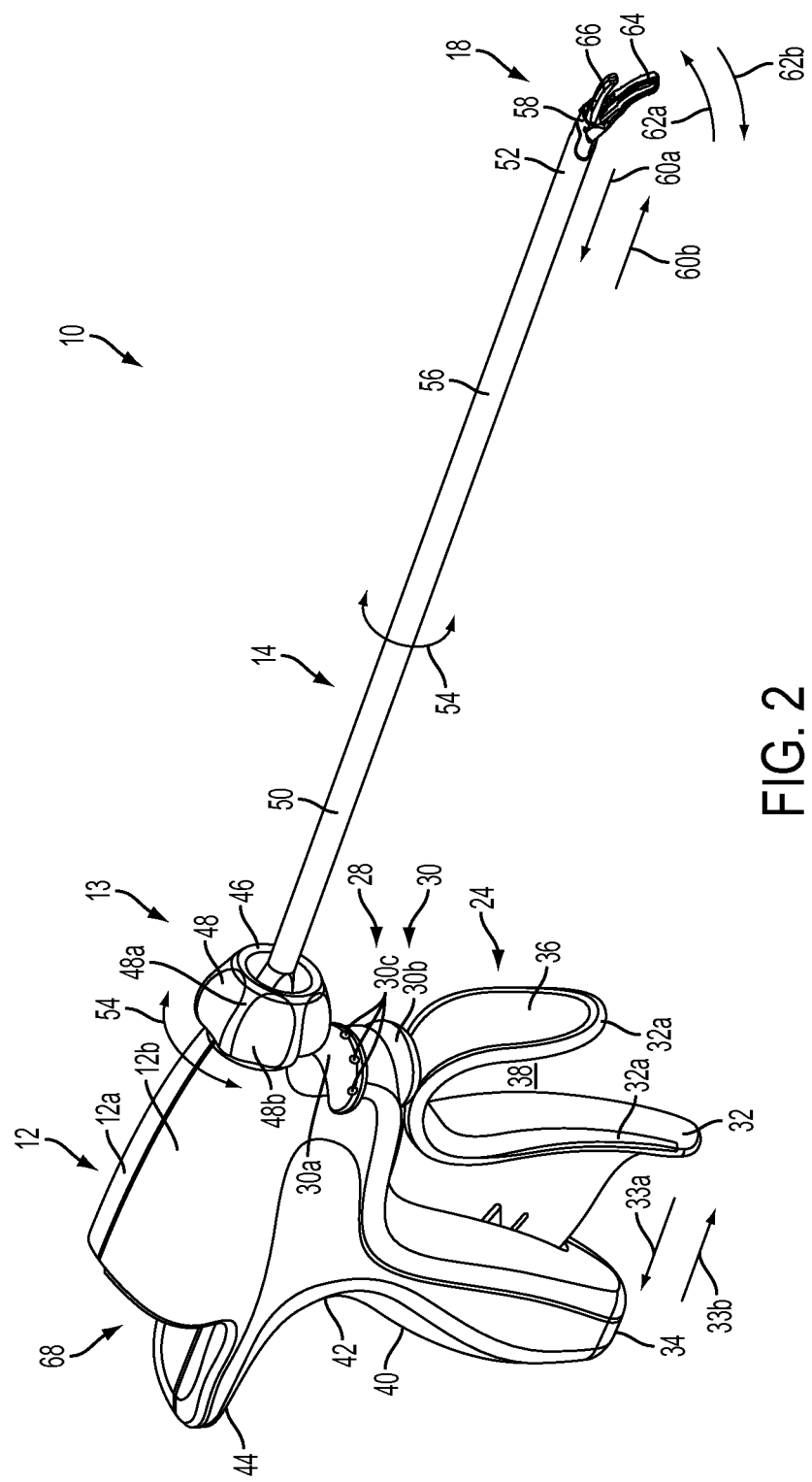
FIG. 2 illustrates one embodiment of the surgical instrument shown in FIG. 1.

FIG. 2 is a left perspective view of one example embodiment of the ultrasonic surgical instrument 10 showing the handle assembly 12, the distal rotation assembly 13, the elongated shaft assembly 14, and the end effector assembly 26. In the illustrated embodiment the elongated shaft assembly 14 comprises a distal end 52 dimensioned to mechanically engage the end effector assembly 26 and a proximal end 50 that mechanically engages the handle assembly 12 and the distal rotation assembly 13. The proximal end 50 of the elongated shaft assembly 14 is received within the handle assembly 12 and the distal rotation assembly 13. More details relating to the connections between the elongated endoscopic shaft assembly 14, the handle assembly 12, and the distal rotation assembly 13 are provided in the description of FIGS. 5 and 7.

In the illustrated embodiment, the trigger assembly 24 comprises a trigger 32 that operates in conjunction with a fixed handle 34. The fixed handle 34 and the trigger 32 are ergonomically formed and adapted to interface comfortably with the user. The fixed handle 34 is integrally associated with the handle assembly 12. The trigger 32 is pivotally movable relative to the fixed handle 34 as explained in more detail below with respect to the operation of the ultrasonic surgical instrument 10. The trigger 32 is pivotally movable in direction 33A toward the fixed handle 34 when the user applies a squeezing force against the trigger 32. A spring element 98 (FIG. 5) causes the trigger 32 to pivotally move in direction 33B when the user releases the squeezing force against the trigger 32.

In one example embodiment, the trigger 32 comprises an elongated trigger hook 36, which defines an aperture 38 between the elongated trigger hook 36 and the trigger 32. The aperture 38 is suitably sized to receive one or multiple fingers of the user therethrough. The trigger 32 also may comprise a resilient portion 32a molded over the trigger 32 substrate. The overmolded resilient portion 32a is formed to provide a more comfortable contact surface for control of the trigger 32 in outward direction 33B. In one example embodiment, the overmolded resilient portion 32a may be provided over a portion of the elongated trigger hook 36. The proximal surface of the elongated trigger hook 32 remains uncoated or coated with a non-resilient substrate to enable the user to easily slide their fingers in and out of the aperture 38. In another embodiment, the geometry of the trigger forms a fully closed loop which defines an aperture suitably sized to receive one or multiple fingers of the user therethrough. The fully closed loop trigger also may comprise a resilient portion molded over the trigger substrate.

In one example embodiment, the fixed handle 34 comprises a proximal contact surface 40 and a grip anchor or saddle surface 42. The saddle surface 42 rests on the web where the thumb and the index finger are joined on the hand. The proximal contact surface 40 has a pistol grip contour that receives the palm of the hand in a normal pistol grip with no rings or apertures. The profile curve of the proximal contact surface 40 may be contoured to accommodate or receive the palm of the hand. A stabilization tail 44 is located towards a more proximal portion of the handle assembly 12. The stabilization tail 44 may be in contact with the uppermost web portion of the hand located between the thumb and the index finger to stabilize the handle assembly 12 and make the handle assembly 12 more controllable.

In one example embodiment, the switch assembly 28 may comprise a toggle switch 30. The toggle switch 30 may be implemented as a single component with a central pivot 304 located within inside the handle assembly 12 to eliminate the possibility of simultaneous activation. In one example embodiment, the toggle switch 30 comprises a first projecting knob 30a and a second projecting knob 30b to set the power setting of the ultrasonic transducer 16 between a minimum power level (e.g., MIN) and a maximum power level (e.g., MAX). In another embodiment, the rocker switch may pivot between a standard setting and a special setting. The special setting may allow one or more special programs to be implemented by the device. The toggle switch 30 rotates about the central pivot as the first projecting knob 30a and the second projecting knob 30b are actuated. The one or more projecting knobs 30a, 30b are coupled to one or more arms that move through a small arc and cause electrical contacts to close or open an electric circuit to electrically energize or de-energize the ultrasonic transducer 16 in accordance with the activation of the first or second projecting knobs 30a, 30b. The toggle switch 30 is coupled to the generator 20 to control the activation of the ultrasonic transducer 16. The toggle switch 30 comprises one or more electrical power setting switches to activate the ultrasonic transducer 16 to set one or more power settings for the ultrasonic transducer 16. The forces required to activate the toggle switch 30 are directed substantially toward the saddle point 42, thus avoiding any tendency of the instrument to rotate in the hand when the toggle switch 30 is activated.

In one example embodiment, the first and second projecting knobs 30a, 30b are located on the distal end of the handle assembly 12 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 30. The projecting knobs 30a, 30b may be configured to wrap around the side of the handle assembly 12 to some extent to be more easily accessible by variable finger lengths and to allow greater freedom of access to activation in awkward positions or for shorter fingers.

In the illustrated embodiment, the first projecting knob 30a comprises a plurality of tactile elements 30c, e.g., textured projections or "bumps" in the illustrated embodiment, to allow the user to differentiate the first projecting knob 30a (MAX) from the second projecting knob 30b (MIN). It will be appreciated by those skilled in the art that several ergonomic features may be incorporated into the handle assembly 12. Such ergonomic features are described in U.S. Pat. App. Pub. No. 2009/0105750 entitled "Ergonomic Surgical Instruments" which is incorporated by reference herein in its entirety.

In one example embodiment, the toggle switch 30 may be operated by the hand of the user. The user may easily access the first and second projecting knobs 30a, 30b at any point while also avoiding inadvertent or unintentional activation at any time. The toggle switch 30 may readily operated with a finger to control the power to the ultrasonic assembly 16 and/or to the ultrasonic assembly 16. For example, the index finger may be employed to activate the first contact portion 30a to turn on the ultrasonic assembly 16 to a maximum (MAX) power level. The index finger may be employed to activate the second contact portion 30b to turn on the ultrasonic assembly 16 to a minimum (MIN) power level. In another embodiment, the rocker switch may pivot the instrument 10 between a standard setting and a special setting. The special setting may allow one or more special programs to be implemented by the instrument 10. The toggle switch 30 may be operated without the user having to look at the first or second projecting knob 30a, 30b. For example, the first projecting knob 30a or the second projecting knob 30b may comprise a texture or projections to tactilely differentiate between the first and second projecting knobs 30a, 30b without looking.

In other embodiments, the trigger 32 and/or the toggle switch 30 may be employed to actuate the electrosurgical/RF module 23 individually or in combination with activation of the ultrasonic generator module 21.

In one example embodiment, the distal rotation assembly 13 is rotatable without limitation in either direction about a longitudinal axis "T." The distal rotation assembly 13 is mechanically engaged to the elongated shaft assembly 14. The distal rotation assembly 13 is located on a distal end of the handle assembly 12. The distal rotation assembly 13 comprises a cylindrical hub 46 and a rotation knob 48 formed over the hub 46. The hub 46 mechanically engages the elongated shaft assembly 14. The rotation knob 48 may comprise fluted polymeric features and may be engaged by a finger (e.g., an index finger) to rotate the elongated shaft assembly 14. The hub 46 may comprise a material molded over the primary structure to form the rotation knob 48. The rotation knob 48 may be overmolded over the hub 46. The hub 46 comprises an end cap portion 46a that is exposed at the distal end. The end cap portion 46a of the hub 46 may contact the surface of a trocar during laparoscopic procedures. The hub 46 may be formed of a hard durable plastic such as polycarbonate to alleviate any friction that may occur between the end cap portion 46a and the trocar. The rotation knob 48 may comprise "scallops" or flutes formed of raised ribs 48a and concave portions 48b located between the ribs 48a to provide a more precise rotational grip. In one example embodiment, the rotation knob 48 may comprise a plurality of flutes (e.g., three or more flutes). In other embodiments, any suitable number of flutes may be employed. The rotation knob 48 may be formed of a softer polymeric material overmolded onto the hard plastic material. For example, the rotation knob 48 may be formed of pliable, resilient, flexible polymeric materials including Versaflex® TPE alloys made by GLS Corporation, for example. This softer overmolded material may provide a greater grip and more precise control of the movement of the rotation knob 48. It will be appreciated that any materials that provide adequate resistance to sterilization, are biocompatible, and provide adequate frictional resistance to surgical gloves may be employed to form the rotation knob 48.

In one example embodiment, the handle assembly 12 is formed from two (2) housing portions or shrouds comprising a first portion 12a and a second portion 12b. From the perspective of a user viewing the handle assembly 12 from the distal end towards the proximal end, the first portion 12a is considered the right portion and the second portion 12b is considered the left portion. Each of the first and second portions 12a, 12b includes a plurality of interfaces 69 (FIG. 7) dimensioned to mechanically align and engage each another to form the handle assembly 12 and enclosing the internal working components thereof. The fixed handle 34, which is integrally associated with the handle assembly 12, takes shape upon the assembly of the first and second portions 12a and 12b of the handle assembly 12. A plurality of additional interfaces (not shown) may be disposed at various points around the periphery of the first and second portions 12a and 12b of the handle assembly 12 for ultrasonic welding purposes, e.g., energy direction/deflection points. The first and second portions 12a and 12b (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

In one example embodiment, the elongated shaft assembly 14 comprises a proximal end 50 adapted to mechanically engage the handle assembly 12 and the distal rotation assembly 13; and a distal end 52 adapted to mechanically engage the end effector assembly 26. The elongated shaft assembly 14 comprises an outer tubular sheath 56 and a reciprocating tubular actuating member 58 located within the outer tubular sheath 56. The proximal end of the tubular reciprocating tubular actuating member 58 is mechanically engaged to the trigger 32 of the handle assembly 12 to move in either direction 60A or 60B in response to the actuation and/or release of the trigger 32. The pivotably moveable trigger 32 may generate reciprocating motion along the longitudinal axis "T." Such motion may be used, for example, to actuate the jaws or clamping mechanism of the end effector assembly 26. A series of linkages translate the pivotal rotation of the trigger 32 to axial movement of a yoke coupled to an actuation mechanism, which controls the opening and closing of the jaws of the clamping mechanism of the end effector assembly 26. The distal end of the tubular reciprocating tubular actuating member 58 is mechanically engaged to the end effector assembly 26. In the illustrated embodiment, the distal end of the tubular reciprocating tubular actuating member 58 is mechanically engaged to a clamp arm assembly 64, which is pivotable about a pivot point 70, to open and close the clamp arm assembly 64 in response to the actuation and/or release of the trigger 32. For example, in the illustrated embodiment, the clamp arm assembly 64 is movable in direction 62A from an open position to a closed position about a pivot point 70 when the trigger 32 is squeezed in direction 33A. The clamp arm assembly 64 is movable in direction 62B from a closed position to an open position about the pivot point 70 when the trigger 32 is released or outwardly contacted in direction 33B.

In one example embodiment, the end effector assembly 26 is attached at the distal end 52 of the elongated shaft assembly 14 and includes a clamp arm assembly 64 and a blade 66. The jaws of the clamping mechanism of the end effector assembly 26 are formed by clamp arm assembly 64 and the blade 66. The blade 66 is ultrasonically actuatable and is acoustically coupled to the ultrasonic transducer 16. The trigger 32 on the handle assembly 12 is ultimately connected to a drive assembly, which together, mechanically cooperate to effect movement of the clamp arm assembly 64. Squeezing the trigger 32 in direction 33A moves the clamp arm assembly 64 in direction 62A from an open position, wherein the clamp arm assembly 64 and the blade 66 are disposed in a spaced relation relative to one another, to a clamped or closed position, wherein the clamp arm assembly 64 and the blade 66 cooperate to grasp tissue therebetween. The clamp arm assembly 64 may comprise a clamp pad (not shown) to engage tissue between the blade 66 and the clamp arm 64. Releasing the trigger 32 in direction 33B moves the clamp arm assembly 64 in direction 62B from a closed relationship, to an open position, wherein the clamp arm assembly 64 and the blade 66 are disposed in a spaced relation relative to one another.

The proximal portion of the handle assembly 12 comprises a proximal opening 68 to receive the distal end of the ultrasonic assembly 16. The ultrasonic assembly 16 is inserted in the proximal opening 68 and is mechanically engaged to the elongated endoscopic shaft assembly 14.

In one example embodiment, the elongated trigger hook 36 portion of the trigger 32 provides a longer trigger lever with a shorter span and rotation travel. The longer lever of the elongated trigger hook 36 allows the user to employ multiple fingers within the aperture 38 to operate the elongated trigger hook 36 and cause the trigger 32 to pivot in direction 33B to open the jaws of the end effector assembly 26. For example, the user may insert three fingers (e.g., the middle, ring, and little fingers) in the aperture 38. Multiple fingers allows the surgeon to exert higher input forces on the trigger 32 and the elongated trigger hook 36 to activate the end effector assembly 26. The shorter span and rotation travel creates a more comfortable grip when closing or squeezing the trigger 32 in direction 33A or when opening the trigger 32 in the outward opening motion in direction 33B lessening the need to extend the fingers further outward. This substantially lessens hand fatigue and strain associated with the outward opening motion of the trigger 32 in direction 33B. The outward opening motion of the trigger may be spring-assisted by spring element 98 (FIG. 5) to help alleviate fatigue. The opening spring force is sufficient to assist the ease of opening, but not strong enough to adversely impact the tactile feedback of tissue tension during spreading dissection.

For example, during a surgical procedure either the index finger may be used to control the rotation of the elongated shaft assembly 14 to locate the jaws of the end effector assembly 26 in a suitable orientation. The middle and/or the other lower fingers may be used to squeeze the trigger 32 and grasp tissue within the jaws. Once the jaws are located in the desired position and the jaws are clamped against the tissue, the index finger can be used to activate the toggle switch 30 to adjust the power level of the ultrasonic transducer 16 to treat the tissue. Once the tissue has been treated, the user may release the trigger 32 by pushing outwardly in the distal direction against the elongated trigger hook 36 with the middle and/or lower fingers to open the jaws of the end effector assembly 26. This basic procedure may be performed without the user having to adjust their grip of the handle assembly 12.

Figure 3:
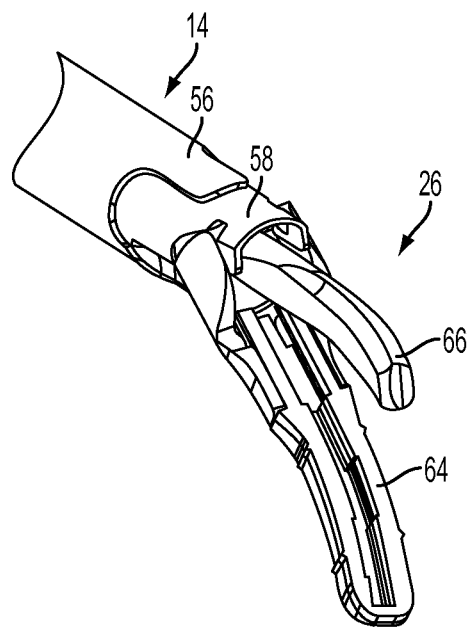
FIG. 3 illustrates one embodiment of an ultrasonic end effector.
Figure 4:
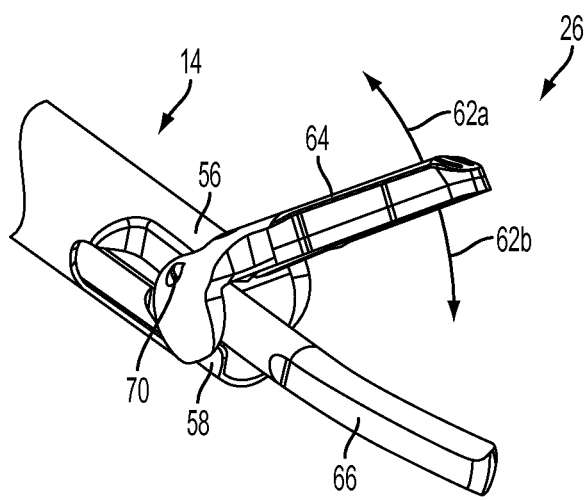
FIG. 4 illustrates another embodiment of an ultrasonic end effector.

FIGS. 3-4 illustrate the connection of the elongated endoscopic shaft assembly 14 relative to the end effector assembly 26. As previously described, in the illustrated embodiment, the end effector assembly 26 comprises a clamp arm assembly 64 and a blade 66 to form the jaws of the clamping mechanism. The blade 66 may be an ultrasonically actuatable blade acoustically coupled to the ultrasonic transducer 16. The trigger 32 is mechanically connected to a drive assembly. Together, the trigger 32 and the drive assembly mechanically cooperate to move the clamp arm assembly 64A to an open position in direction 62B wherein the clamp arm assembly 64 and the blade 66 are disposed in spaced relation relative to one another, to a clamped or closed position in direction 62B wherein the clamp arm assembly 64 and the blade 66 cooperate to grasp tissue therebetween. The clamp arm assembly 64 may comprise a clamp pad (not shown) to engage tissue between the blade 66 and the clamp arm 64. The distal end of the tubular reciprocating tubular actuating member 58 is mechanically engaged to the end effector assembly 26. In the illustrated embodiment, the distal end of the tubular reciprocating tubular actuating member 58 is mechanically engaged to the clamp arm assembly 64, which is pivotable about the pivot point 70, to open and close the clamp arm assembly 64 in response to the actuation and/or release of the trigger 32. For example, in the illustrated embodiment, the clamp arm assembly 64 is movable from an open position to a closed position in direction 62B about a pivot point 70 when the trigger 32 is squeezed in direction 33A. The clamp arm assembly 64 is movable from a closed position to an open position in direction 62A about the pivot point 70 when the trigger 32 is released or outwardly contacted in direction 33B.

As previously discussed, the clamp arm assembly 64 may comprise electrodes electrically coupled to the electrosurgical/RF generator module 23 to receive therapeutic and/or sub-therapeutic energy, where the electrosurgical/RF energy may be applied to the electrodes either simultaneously or non-simultaneously with the ultrasonic energy being applied to the blade 66. Such energy activations may be applied in any suitable combinations to achieve a desired tissue effect in cooperation with an algorithm or other control logic.

Figure 5:
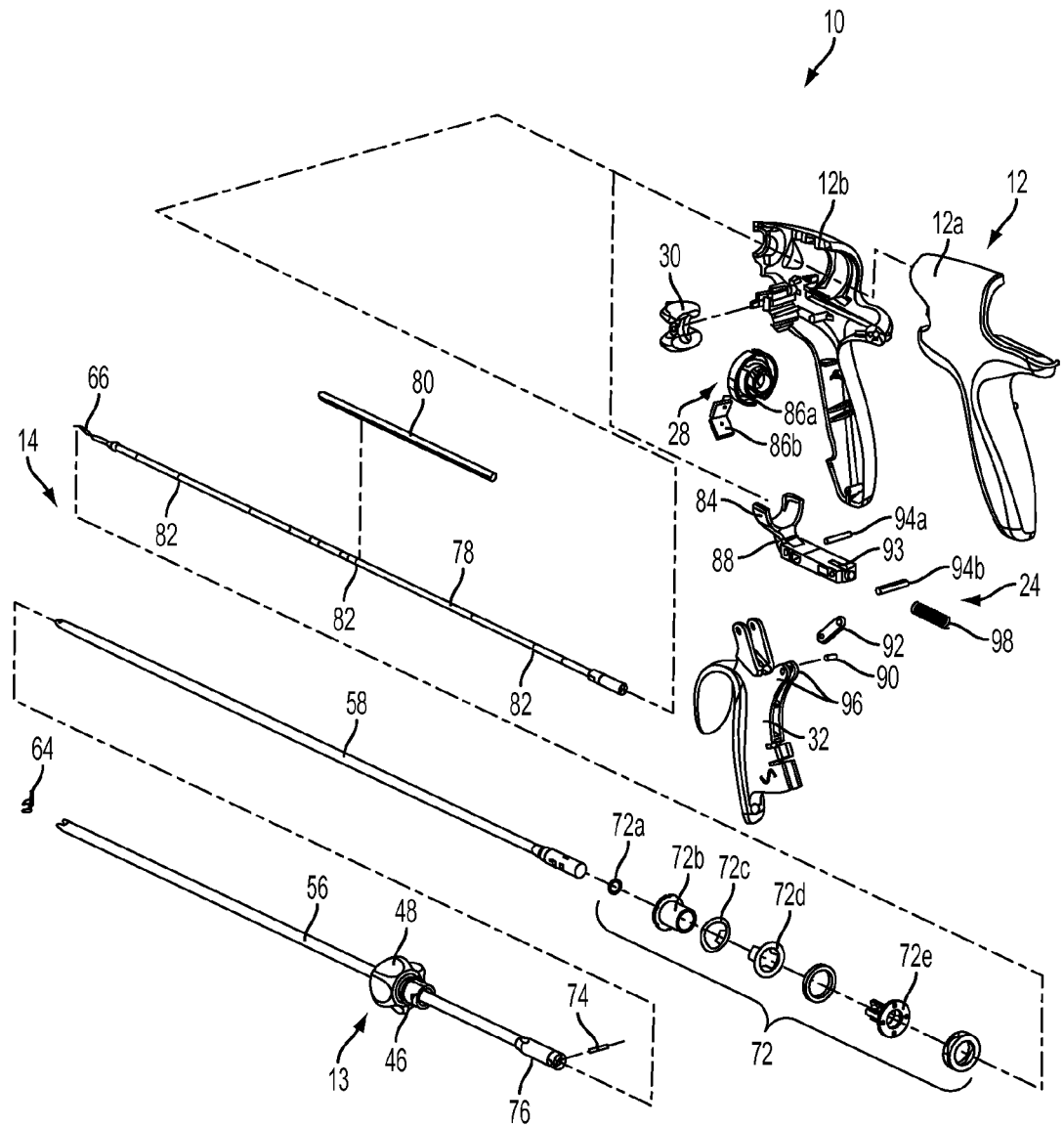
FIG. 5 illustrates an exploded view of one embodiment of the surgical instrument shown in FIG. 1.
Figure 7:
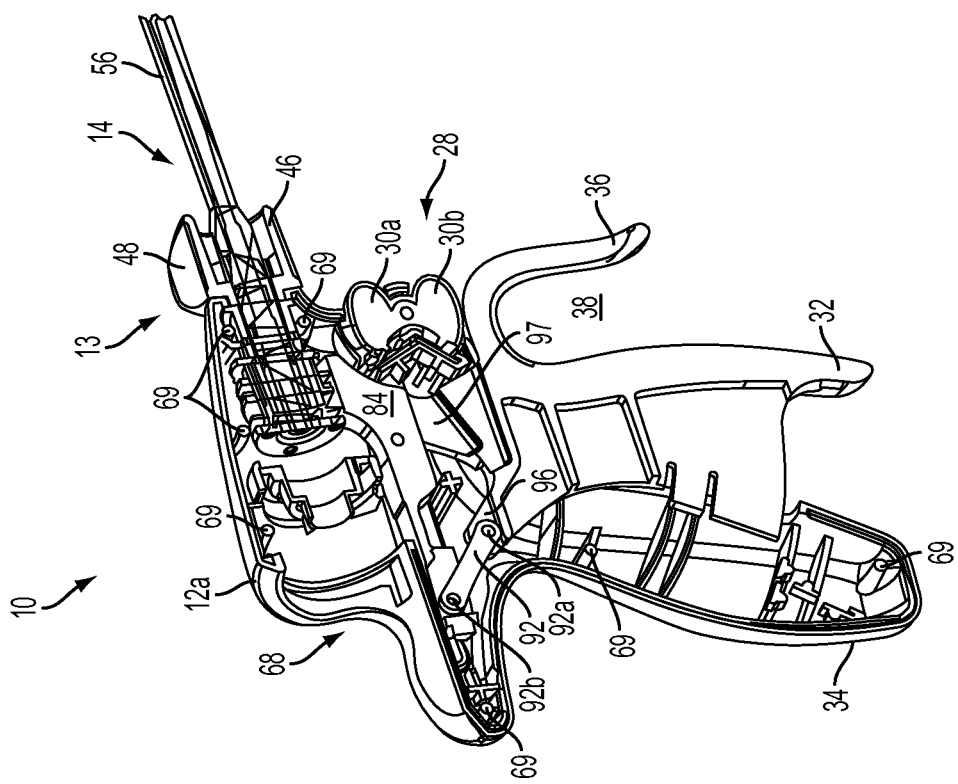
FIG. 7 illustrates various internal components of the surgical instrument shown in FIG. 1
Figure 6:
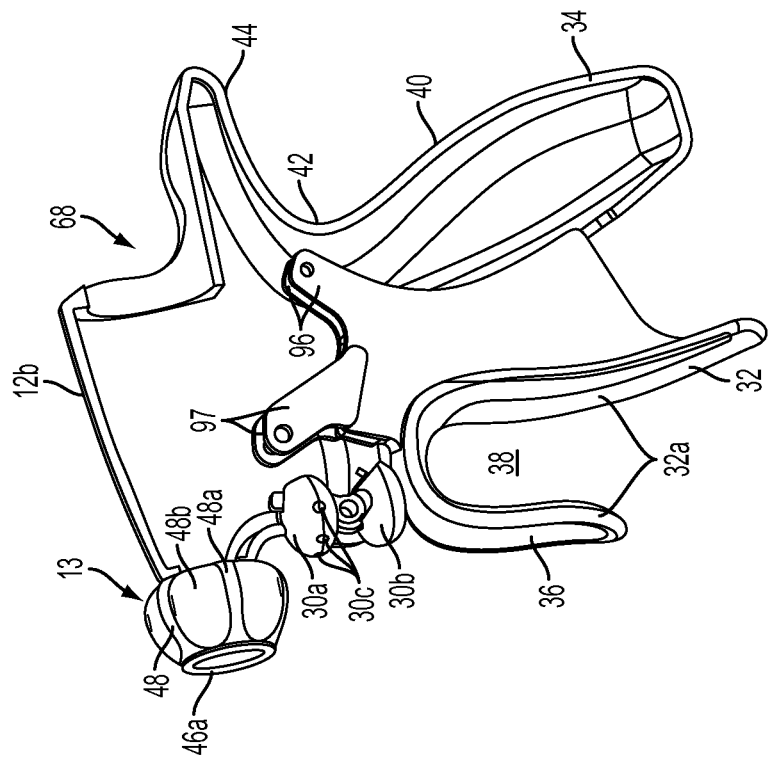
FIG. 6 illustrates a cut-away view of one embodiment of the surgical instrument shown in FIG. 1.

FIG. 5 is an exploded view of the ultrasonic surgical instrument 10 shown in FIG. 2. In the illustrated embodiment, the exploded view shows the internal elements of the handle assembly 12, the handle assembly 12, the distal rotation assembly 13, the switch assembly 28, and the elongated endoscopic shaft assembly 14. In the illustrated embodiment, the first and second portions 12a, 12b mate to form the handle assembly 12. The first and second portions 12a, 12b each comprises a plurality of interfaces 69 dimensioned to mechanically align and engage one another to form the handle assembly 12 and enclose the internal working components of the ultrasonic surgical instrument 10. The rotation knob 48 is mechanically engaged to the outer tubular sheath 56 so that it may be rotated in circular direction 54 up to 360°. The outer tubular sheath 56 is located over the reciprocating tubular actuating member 58, which is mechanically engaged to and retained within the handle assembly 12 via a plurality of coupling elements 72. The coupling elements 72 may comprise an O-ring 72a, a tube collar cap 72b, a distal washer 72c, a proximal washer 72d, and a thread tube collar 72e. The reciprocating tubular actuating member 58 is located within a reciprocating yoke 84, which is retained between the first and second portions 12a, 12b of the handle assembly 12. The yoke 84 is part of a reciprocating yoke assembly 88. A series of linkages translate the pivotal rotation of the elongated trigger hook 32 to the axial movement of the reciprocating yoke 84, which controls the opening and closing of the jaws of the clamping mechanism of the end effector assembly 26 at the distal end of the ultrasonic surgical instrument 10. In one example embodiment, a four-link design provides mechanical advantage in a relatively short rotation span, for example.

In one example embodiment, an ultrasonic transmission waveguide 78 is disposed inside the reciprocating tubular actuating member 58. The distal end 52 of the ultrasonic transmission waveguide 78 is acoustically coupled (e.g., directly or indirectly mechanically coupled) to the blade 66 and the proximal end 50 of the ultrasonic transmission waveguide 78 is received within the handle assembly 12. The proximal end 50 of the ultrasonic transmission waveguide 78 is adapted to acoustically couple to the distal end of the ultrasonic transducer 16 as discussed in more detail below. The ultrasonic transmission waveguide 78 is isolated from the other elements of the elongated shaft assembly 14 by a protective sheath 80 and a plurality of isolation elements 82, such as silicone rings. The outer tubular sheath 56, the reciprocating tubular actuating member 58, and the ultrasonic transmission waveguide 78 are mechanically engaged by a pin 74. The switch assembly 28 comprises the toggle switch 30 and electrical elements 86a,b to electrically energize the ultrasonic transducer 16 in accordance with the activation of the first or second projecting knobs 30a, 30b.

In one example embodiment, the outer tubular sheath 56 isolates the user or the patient from the ultrasonic vibrations of the ultrasonic transmission waveguide 78. The outer tubular sheath 56 generally includes a hub 76. The outer tubular sheath 56 is threaded onto the distal end of the handle assembly 12. The ultrasonic transmission waveguide 78 extends through the opening of the outer tubular sheath 56 and the isolation elements 82 isolate the ultrasonic transmission waveguide 78 from the outer tubular sheath 56. The outer tubular sheath 56 may be attached to the waveguide 78 with the pin 74. The hole to receive the pin 74 in the waveguide 78 may occur nominally at a displacement node. The waveguide 78 may screw or snap into the hand piece handle assembly 12 by a stud. Flat portions on the hub 76 may allow the assembly to be torqued to a required level. In one example embodiment, the hub 76 portion of the outer tubular sheath 56 is preferably constructed from plastic and the tubular elongated portion of the outer tubular sheath 56 is fabricated from stainless steel. Alternatively, the ultrasonic transmission waveguide 78 may comprise polymeric material surrounding it to isolate it from outside contact.

In one example embodiment, the distal end of the ultrasonic transmission waveguide 78 may be coupled to the proximal end of the blade 66 by an internal threaded connection, preferably at or near an antinode. It is contemplated that the blade 66 may be attached to the ultrasonic transmission waveguide 78 by any suitable means, such as a welded joint or the like. Although the blade 66 may be detachable from the ultrasonic transmission waveguide 78, it is also contemplated that the single element end effector (e.g., the blade 66) and the ultrasonic transmission waveguide 78 may be formed as a single unitary piece.

In one example embodiment, the trigger 32 is coupled to a linkage mechanism to translate the rotational motion of the trigger 32 in directions 33A and 33B to the linear motion of the reciprocating tubular actuating member 58 in corresponding directions 60A and 60B. The trigger 32 comprises a first set of flanges 97 with openings formed therein to receive a first yoke pin 94a. The first yoke pin 94a is also located through a set of openings formed at the distal end of the yoke 84. The trigger 32 also comprises a second set of flanges 96 to receive a first end 92a of a link 92. A trigger pin 90 is received in openings formed in the link 92 and the second set of flanges 96. The trigger pin 90 is received in the openings formed in the link 92 and the second set of flanges 96 and is adapted to couple to the first and second portions 12a, 12b of the handle assembly 12 to form a trigger pivot point for the trigger 32. A second end 92b of the link 92 is received in a slot 93 formed in a proximal end of the yoke 84 and is retained therein by a second yoke pin 94b. As the trigger 32 is pivotally rotated about the pivot point 190 formed by the trigger pin 90, the yoke translates horizontally along longitudinal axis "T" in a direction indicated by arrows 60A,B.

FIG. 8 illustrates one example embodiment of an ultrasonic surgical instrument 10. In the illustrated embodiment, a cross-sectional view of the ultrasonic transducer 16 is shown within a partial cutaway view of the handle assembly 12. One example embodiment of the ultrasonic surgical instrument 10 comprises the ultrasonic signal generator 20 coupled to the ultrasonic transducer 16, comprising a hand piece housing 99, and an ultrasonically actuatable single or multiple element end effector assembly 26. As previously discussed, the end effector assembly 26 comprises the ultrasonically actuatable blade 66 and the clamp arm 64. The ultrasonic transducer 16, which is known as a "Langevin stack", generally includes a transduction portion 100, a first resonator portion or end-bell 102, and a second resonator portion or fore-bell 104, and ancillary components. The total construction of these components is a resonator. The ultrasonic transducer 16 is preferably an integral number of one-half system wavelengths ($n\lambda/2$; where "n" is any positive integer; e.g., n=1, 2, 3 . . . ) in length as will be described in more detail later. An acoustic assembly 106 includes the ultrasonic transducer 16, a nose cone 108, a velocity transformer 118, and a surface 110.

In one example embodiment, the distal end of the end-bell 102 is connected to the proximal end of the transduction portion 100, and the proximal end of the fore-bell 104 is connected to the distal end of the transduction portion 100. The fore-bell 104 and the end-bell 102 have a length determined by a number of variables, including the thickness of the transduction portion 100, the density and modulus of elasticity of the material used to manufacture the end-bell 102 and the fore-bell 22, and the resonant frequency of the ultrasonic transducer 16. The fore-bell 104 may be tapered inwardly from its proximal end to its distal end to amplify the ultrasonic vibration amplitude as the velocity transformer 118, or alternately may have no amplification. A suitable vibrational frequency range may be about 20 Hz to 32 kHz and a well-suited vibrational frequency range may be about 30-10 kHz. A suitable operational vibrational frequency may be approximately 55.5 kHz, for example.

In one example embodiment, the piezoelectric elements 112 may be fabricated from any suitable material, such as, for example, lead zirconate-titanate, lead meta-niobate, lead titanate, barium titanate, or other piezoelectric ceramic material. Each of positive electrodes 114, negative electrodes 116, and the piezoelectric elements 112 has a bore extending through the center. The positive and negative electrodes 114 and 116 are electrically coupled to wires 120 and 122, respectively. The wires 120 and 122 are encased within the cable 22 and electrically connectable to the ultrasonic signal generator 20.

The ultrasonic transducer 16 of the acoustic assembly 106 converts the electrical signal from the ultrasonic signal generator 20 into mechanical energy that results in primarily a standing acoustic wave of longitudinal vibratory motion of the ultrasonic transducer 16 and the blade 66 portion of the end effector assembly 26 at ultrasonic frequencies. In another embodiment, the vibratory motion of the ultrasonic transducer may act in a different direction. For example, the vibratory motion may comprise a local longitudinal component of a more complicated motion of the tip of the elongated shaft assembly 14. A suitable generator is available as model number GEN11, from Ethicon Endo-Surgery, Inc., Cincinnati, Ohio. When the acoustic assembly 106 is energized, a vibratory motion standing wave is generated through the acoustic assembly 106. The ultrasonic surgical instrument 10 is designed to operate at a resonance such that an acoustic standing wave pattern of predetermined amplitude is produced. The amplitude of the vibratory motion at any point along the acoustic assembly 106 depends upon the location along the acoustic assembly 106 at which the vibratory motion is measured. A minimum or zero crossing in the vibratory motion standing wave is generally referred to as a node (i.e., where motion is minimal), and a local absolute value maximum or peak in the standing wave is generally referred to as an anti-node (i.e., where local motion is maximal). The distance between an anti-node and its nearest node is one-quarter wavelength ($\lambda/4$).

The wires 120 and 122 transmit an electrical signal from the ultrasonic signal generator 20 to the positive electrodes 114 and the negative electrodes 116. The piezoelectric elements 112 are energized by the electrical signal supplied from the ultrasonic signal generator 20 in response to an actuator 224, such as a foot switch, for example, to produce an acoustic standing wave in the acoustic assembly 106. The electrical signal causes disturbances in the piezoelectric elements 112 in the form of repeated small displacements resulting in large alternating compression and tension forces within the material. The repeated small displacements cause the piezoelectric elements 112 to expand and contract in a continuous manner along the axis of the voltage gradient, producing longitudinal waves of ultrasonic energy. The ultrasonic energy is transmitted through the acoustic assembly 106 to the blade 66 portion of the end effector assembly 26 via a transmission component or an ultrasonic transmission waveguide portion 78 of the elongated shaft assembly 14.

In one example embodiment, in order for the acoustic assembly 106 to deliver energy to the blade 66 portion of the end effector assembly 26, all components of the acoustic assembly 106 must be acoustically coupled to the blade 66. The distal end of the ultrasonic transducer 16 may be acoustically coupled at the surface 110 to the proximal end of the ultrasonic transmission waveguide 78 by a threaded connection such as a stud 124.

In one example embodiment, the components of the acoustic assembly 106 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 106. It is also contemplated that the acoustic assembly 106 may incorporate any suitable arrangement of acoustic elements.

In one example embodiment, the blade 66 may have a length substantially equal to an integral multiple of one-half system wavelengths ($n\lambda/2$). A distal end of the blade 66 may be disposed near an antinode in order to provide the maximum longitudinal excursion of the distal end. When the transducer assembly is energized, the distal end of the blade 66 may be configured to move in the range of, for example, approximately 10 to 500 microns peak-to-peak, and preferably in the range of about 30 to 64 microns at a predetermined vibrational frequency of 55 kHz, for example.

In one example embodiment, the blade 66 may be coupled to the ultrasonic transmission waveguide 78. The blade 66 and the ultrasonic transmission waveguide 78 as illustrated are formed as a single unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the blade 66 may be separable (and of differing composition) from the ultrasonic transmission waveguide 78, and coupled by, for example, a stud, weld, glue, quick connect, or other suitable known methods. The length of the ultrasonic transmission waveguide 78 may be substantially equal to an integral number of one-half wavelengths ($n\lambda/2$), for example. The ultrasonic transmission waveguide 78 may be preferably fabricated from a solid core shaft constructed out of material suitable to propagate ultrasonic energy efficiently, such as the titanium alloy discussed above (i.e., Ti6Al4V) or any suitable aluminum alloy, or other alloys, for example.

In one example embodiment, the ultrasonic transmission waveguide 78 comprises a longitudinally projecting attachment post at a proximal end to couple to the surface 110 of the ultrasonic transmission waveguide 78 by a threaded connection such as the stud 124. The ultrasonic transmission waveguide 78 may include a plurality of stabilizing silicone rings or compliant supports 82 (FIG. 5) positioned at a plurality of nodes. The silicone rings 82 dampen undesirable vibration and isolate the ultrasonic energy from an outer protective sheath 80 (FIG. 5) assuring the flow of ultrasonic energy in a longitudinal direction to the distal end of the blade 66 with maximum efficiency.

Figure 9:
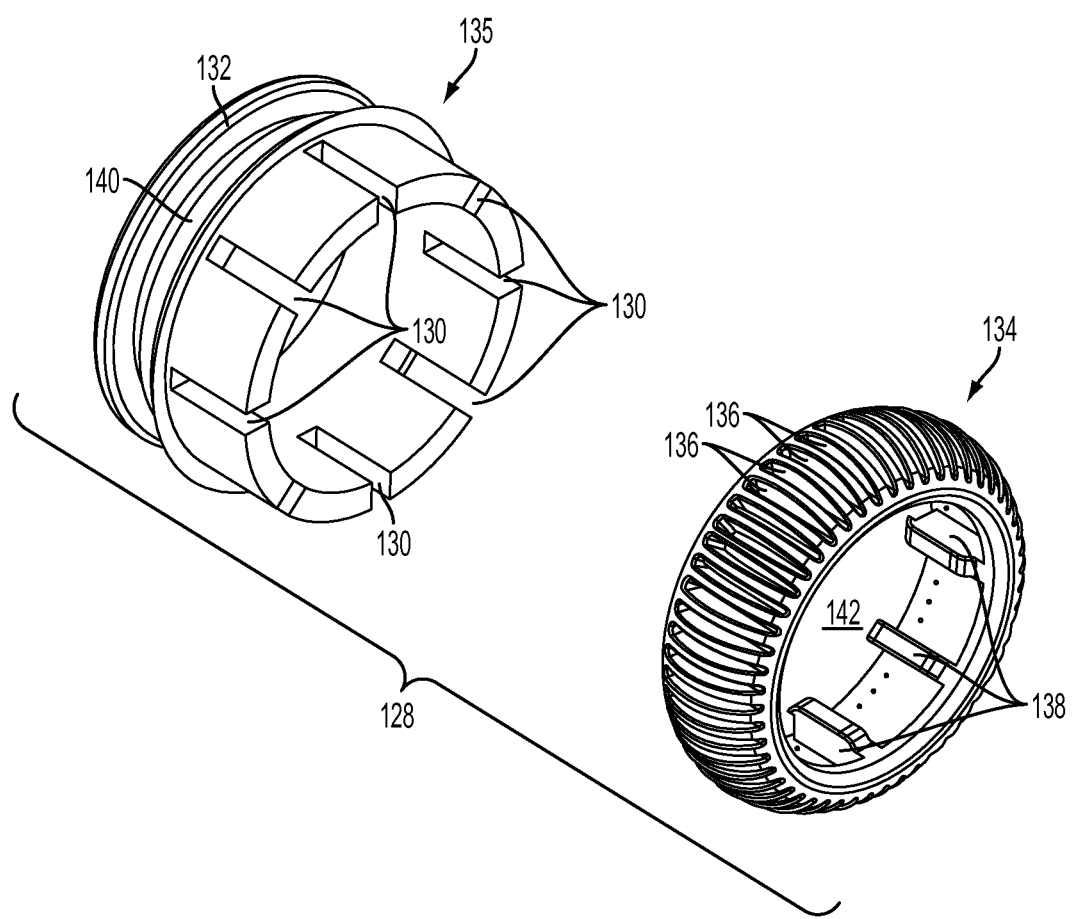
FIG. 9 illustrates one embodiment of a rotation assembly included in one example embodiment of the surgical instrument of FIG. 1.

FIG. 9 illustrates one example embodiment of the proximal rotation assembly 128. In the illustrated embodiment, the proximal rotation assembly 128 comprises the proximal rotation knob 134 inserted over the cylindrical hub 135. The proximal rotation knob 134 comprises a plurality of radial projections 138 that are received in corresponding slots 130 formed on a proximal end of the cylindrical hub 135. The proximal rotation knob 134 defines an opening 142 to receive the distal end of the ultrasonic transducer 16. The radial projections 138 are formed of a soft polymeric material and define a diameter that is undersized relative to the outside diameter of the ultrasonic transducer 16 to create a friction interference fit when the distal end of the ultrasonic transducer 16. The polymeric radial projections 138 protrude radially into the opening 142 to form "gripper" ribs that firmly grip the exterior housing of the ultrasonic transducer 16. Therefore, the proximal rotation knob 134 securely grips the ultrasonic transducer 16.

The distal end of the cylindrical hub 135 comprises a circumferential lip 132 and a circumferential bearing surface 140. The circumferential lip engages a groove formed in the housing 12 and the circumferential bearing surface 140 engages the housing 12. Thus, the cylindrical hub 135 is mechanically retained within the two housing portions (not shown) of the housing 12. The circumferential lip 132 of the cylindrical hub 135 is located or "trapped" between the first and second housing portions 12a, 12b and is free to rotate in place within the groove. The circumferential bearing surface 140 bears against interior portions of the housing to assist proper rotation. Thus, the cylindrical hub 135 is free to rotate in place within the housing. The user engages the flutes 136 formed on the proximal rotation knob 134 with either the finger or the thumb to rotate the cylindrical hub 135 within the housing 12.

In one example embodiment, the cylindrical hub 135 may be formed of a durable plastic such as polycarbonate. In one example embodiment, the cylindrical hub 135 may be formed of a siliconized polycarbonate material. In one example embodiment, the proximal rotation knob 134 may be formed of pliable, resilient, flexible polymeric materials including Versaflex® TPE alloys made by GLS Corporation, for example. The proximal rotation knob 134 may be formed of elastomeric materials, thermoplastic rubber known as Santoprene®, other thermoplastic vulcanizates (TPVs), or elastomers, for example. The embodiments, however, are not limited in this context.

Figure 10:
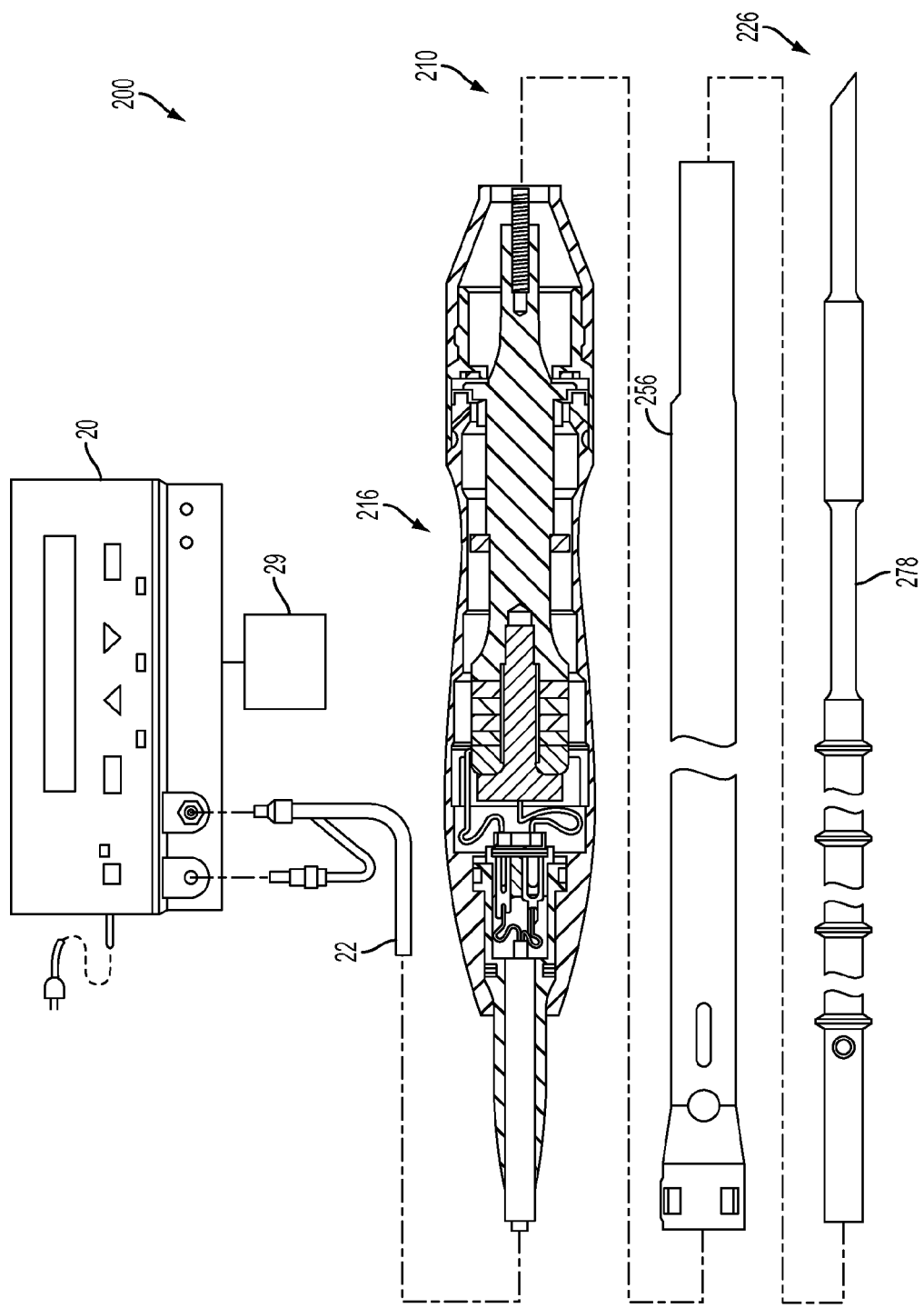
FIG. 10 illustrates one embodiment of a surgical system including a surgical instrument having a single element end effector.

FIG. 10 illustrates one embodiment of a surgical system 200 including a surgical instrument 210 having single element end effector 278. The system 200 may include a transducer assembly 216 coupled to the end effector 278 and a sheath 256 positioned around the proximal portions of the end effector 278 as shown. The transducer assembly 216 and end effector 278 may operate in a manner similar to that of the transducer assembly 16 and end effector 18 described above to produce ultrasonic energy that may be transmitted to tissue via blade 226.

Figure 11:
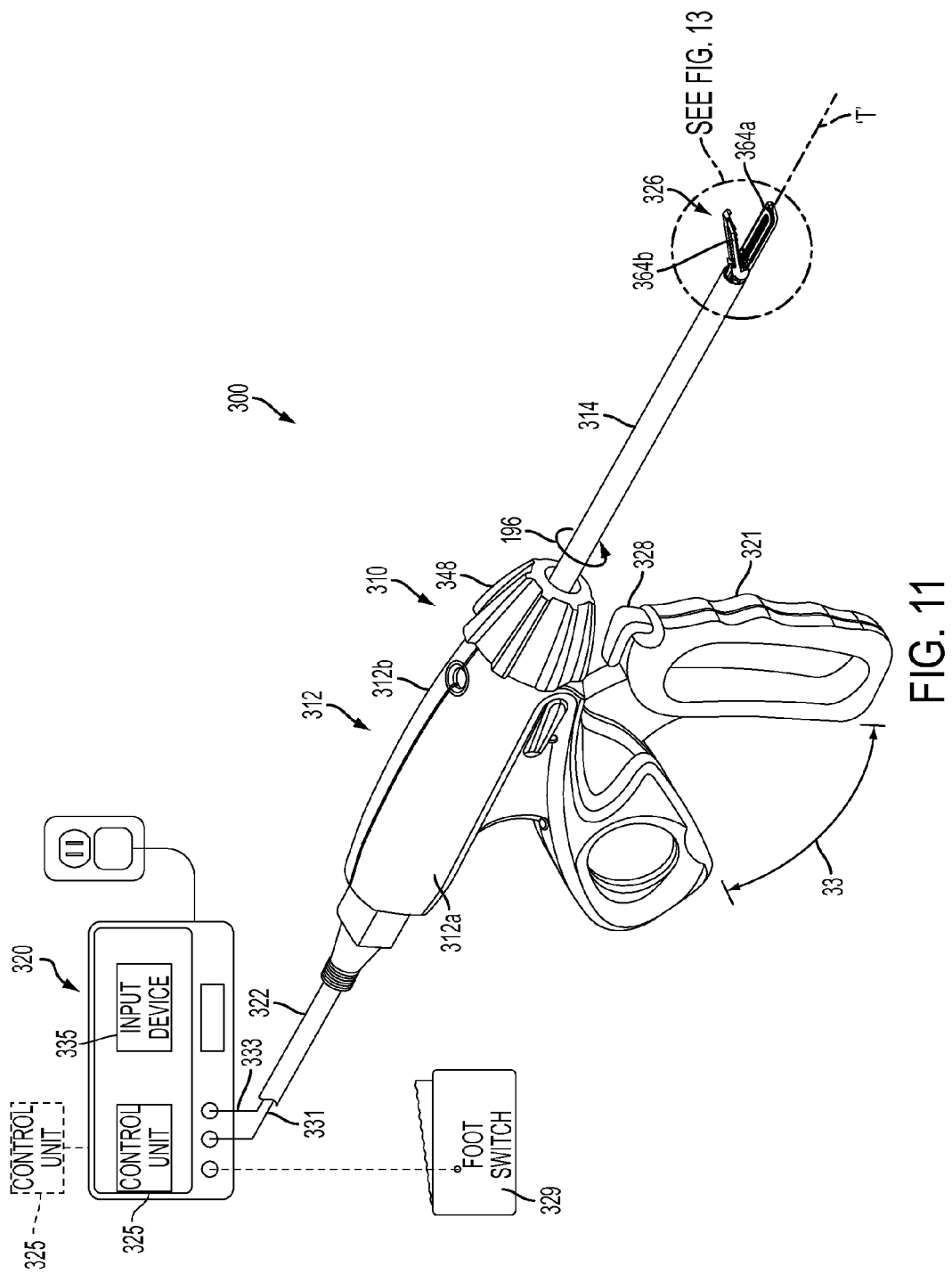
FIG. 11 is a perspective view of one embodiment of an electrical energy surgical instrument.

FIGS. 11-18C illustrate various embodiments of surgical instruments that utilize therapeutic or sub-therapeutic electrical energy to treat and/or destroy tissue or provide feedback to the generators (e.g., electrosurgical instruments). The embodiments of FIGS. 11-18C are adapted for use in a manual or hand-operated manner although electrosurgical instruments may be utilized in robotic applications as well. FIG. 11 is a perspective view of one example embodiment of a surgical instrument system 300 comprising an electrical energy surgical instrument 310. The electrosurgical instrument 310 may comprise a proximal handle 312, a distal working end or end effector 326 and an introducer or elongated shaft 314 disposed in-between.

The electrosurgical system 300 can be configured to supply energy, such as electrical energy, ultrasonic energy, heat energy, or any combination thereof, to the tissue of a patient either independently or simultaneously as described, for example, in connection with FIG. 1, for example. In one example embodiment, the electrosurgical system 300 includes a generator 320 in electrical communication with the electrosurgical instrument 310. The generator 320 is connected to electrosurgical instrument 310 via a suitable transmission medium such as a cable 322. In one example embodiment, the generator 320 is coupled to a controller, such as a control unit 325, for example. In various embodiments, the control unit 325 may be formed integrally with the generator 320 or may be provided as a separate circuit module or device electrically coupled to the generator 320 (shown in phantom to illustrate this option). Although in the presently disclosed embodiment, the generator 320 is shown separate from the electrosurgical instrument 310, in one example embodiment, the generator 320 (and/or the control unit 325) may be formed integrally with the electrosurgical instrument 310 to form a unitary electrosurgical system 300, where a battery located within the electrosurgical instrument 310 is the energy source and a circuit coupled to the battery produces the suitable electrical energy, ultrasonic energy, or heat energy. Once such example is described herein below, in connection with FIGS. 17-18C.

The generator 320 may comprise an input device 335 located on a front panel of the generator 320 console. The input device 335 may comprise any suitable device that generates signals suitable for programming the operation of the generator 320, such as a keyboard, or input port, for example. In one example embodiment, various electrodes in the first jaw 364A and the second jaw 364B may be coupled to the generator 320. The cable 322 may comprise multiple electrical conductors for the application of electrical energy to positive (+) and negative (−) electrodes of the electrosurgical instrument 310. The control unit 325 may be used to activate the generator 320, which may serve as an electrical source. In various embodiments, the generator 320 may comprise an RF source, an ultrasonic source, a direct current source, and/or any other suitable type of electrical energy source, for example, which may be activated independently or simultaneously.

In various embodiments, the electrosurgical system 300 may comprise at least one supply conductor 331 and at least one return conductor 333, wherein current can be supplied to electrosurgical instrument 300 via the supply conductor 331 and wherein the current can flow back to the generator 320 via the return conductor 333. In various embodiments, the supply conductor 331 and the return conductor 333 may comprise insulated wires and/or any other suitable type of conductor. In certain embodiments, as described below, the supply conductor 331 and the return conductor 333 may be contained within and/or may comprise the cable 322 extending between, or at least partially between, the generator 320 and the end effector 326 of the electrosurgical instrument 310. In any event, the generator 320 can be configured to apply a sufficient voltage differential between the supply conductor 331 and the return conductor 333 such that sufficient current can be supplied to the end effector 110.

Figure 12:
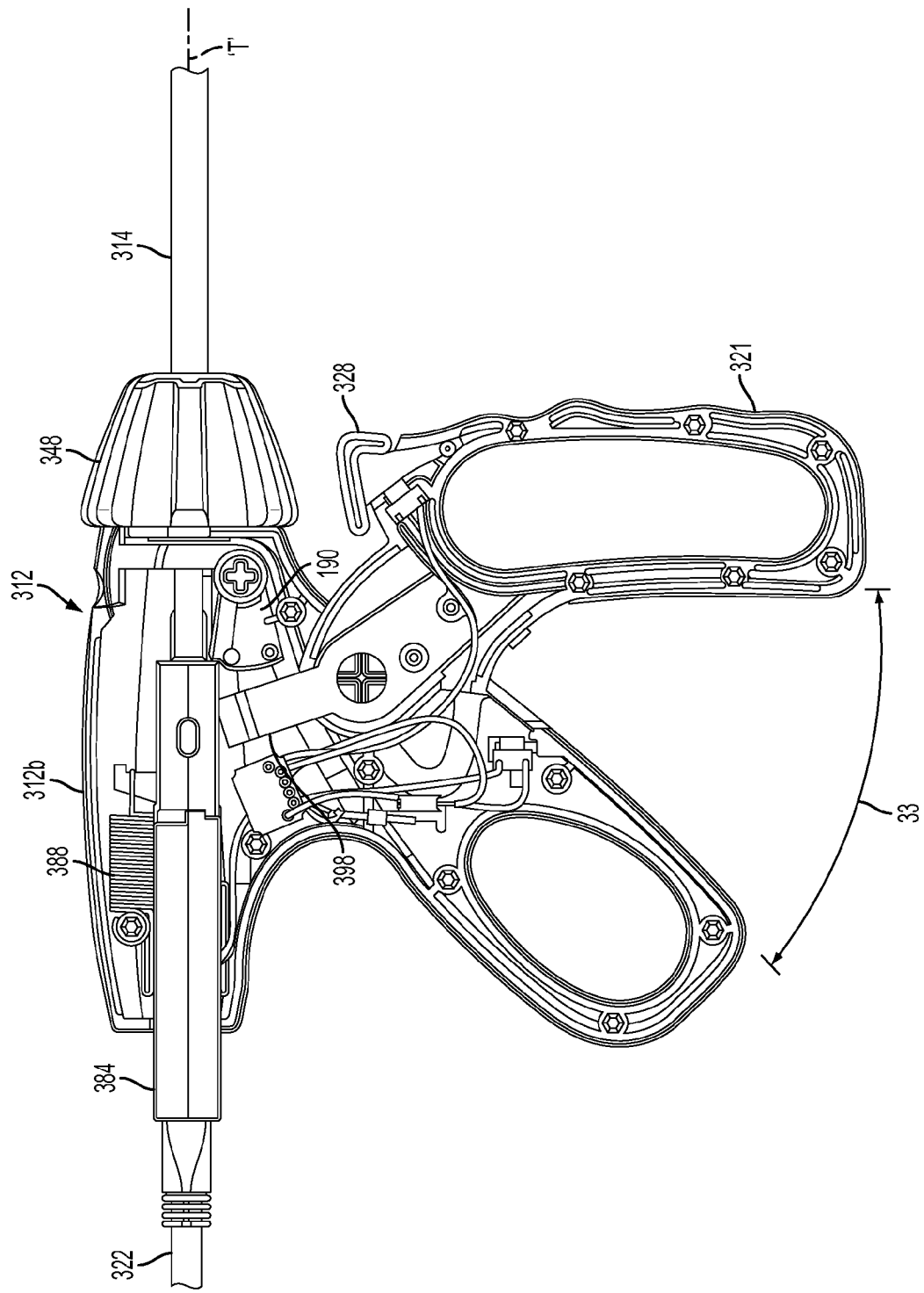
FIG. 12 is a side view of a handle of one embodiment of the surgical instrument of FIG. 1 with a half of a handle body removed to illustrate some of the components therein.

FIG. 12 is a side view of one example embodiment of the handle 312 of the surgical instrument 310. In FIG. 12, the handle 312 is shown with half of a first handle body 312A (see FIG. 11) removed to illustrate various components within second handle body 312B. The handle 312 may comprise a lever arm 321 (e.g., a trigger) which may be pulled along a path 33. The lever arm 321 may be coupled to an axially moveable member 378 (FIGS. 13-16) disposed within elongated shaft 314 by a shuttle 384 operably engaged to an extension 398 of lever arm 321. The shuttle 384 may further be connected to a biasing device, such as a spring 388, which may also be connected to the second handle body 312B, to bias the shuttle 384 and thus the axially moveable member 378 in a proximal direction, thereby urging the jaws 364A and 364B to an open position as seen in FIG. 11. Also, referring to FIGS. 11-12, a locking member 190 (see FIG. 12) may be moved by a locking switch 328 (see FIG. 11) between a locked position, where the shuttle 384 is substantially prevented from moving distally as illustrated, and an unlocked position, where the shuttle 384 may be allowed to freely move in the distal direction, toward the elongated shaft 314. In some embodiments, the locking switch 328 may be implemented as a button. The handle 312 can be any type of pistol-grip or other type of handle known in the art that is configured to carry actuator levers, triggers or sliders for actuating the first jaw 364A and the second jaw 364B. The elongated shaft 314 may have a cylindrical or rectangular cross-section, for example, and can comprise a thin-wall tubular sleeve that extends from handle 312. The elongated shaft 314 may include a bore extending therethrough for carrying actuator mechanisms, for example, the axially moveable member 378, for actuating the jaws and for carrying electrical leads for delivery of electrical energy to electrosurgical components of the end effector 326.

The end effector 326 may be adapted for capturing and transecting tissue and for the contemporaneously welding the captured tissue with controlled application of energy (e.g., RF energy). The first jaw 364A and the second jaw 364B may close to thereby capture or engage tissue about a longitudinal axis "T" defined by the axially moveable member 378. The first jaw 364A and second jaw 364B may also apply compression to the tissue. In some embodiments, the elongated shaft 314, along with first jaw 364A and second jaw 364B, can be rotated a full 360° degrees, as shown by arrow 196 (see FIG. 11), relative to handle 312. For example, a rotation knob 348 may be rotatable about the longitudinal axis of the elongated shaft 314 and may be coupled to the elongated shaft 314 such that rotation of the knob 348 causes corresponding rotation of the elongated shaft 314. The first jaw 364A and the second jaw 364B can remain openable and/or closeable while rotated.

Figure 13:
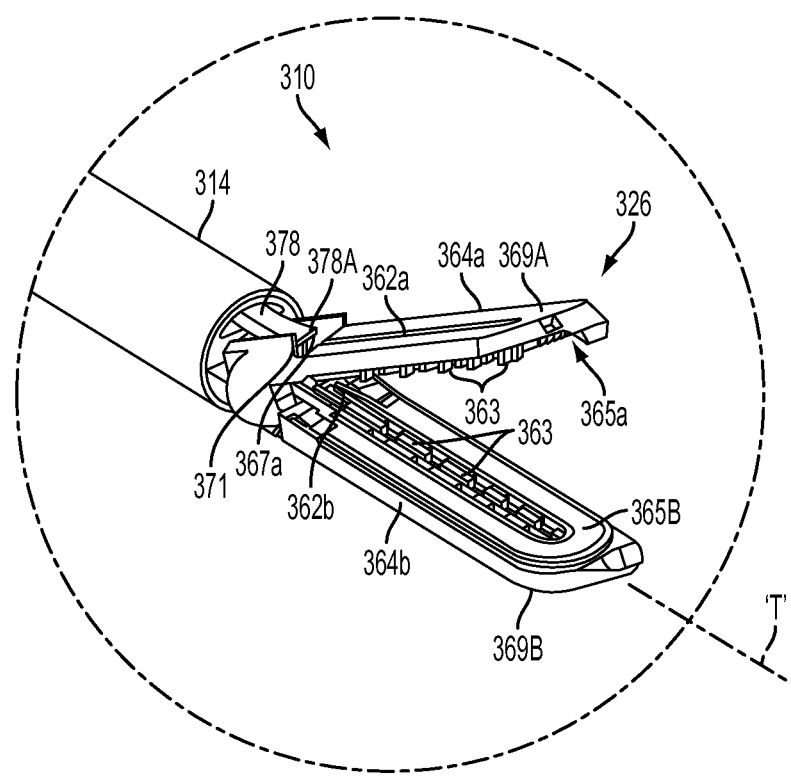
FIG. 13 illustrates a perspective view of one embodiment of the end effector of the surgical instrument of FIG. 11 with the jaws open and the distal end of an axially movable member in a retracted position.
Figure 14:
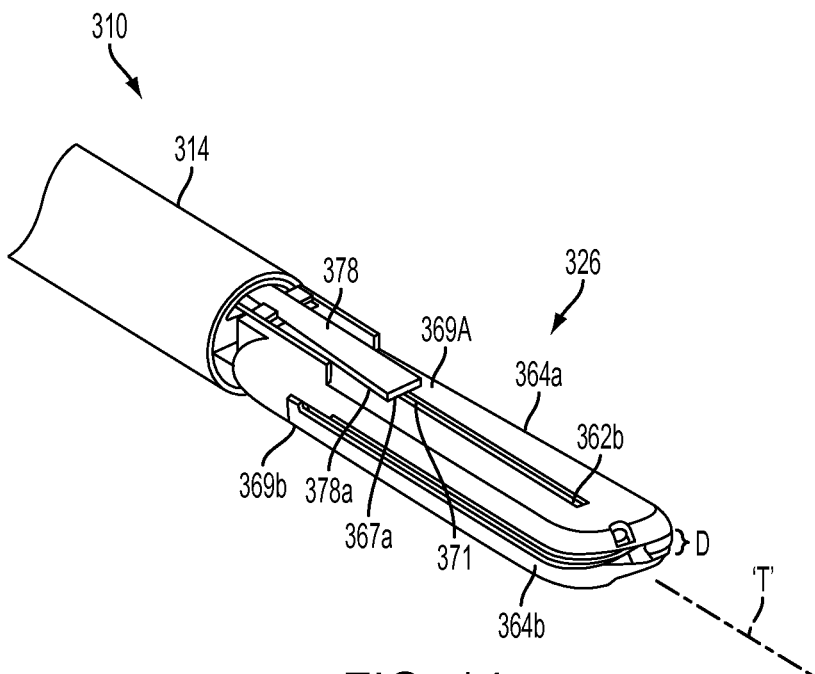
FIG. 14 illustrates a perspective view of one embodiment of the end effector of the surgical instrument of FIG. 11 with the jaws closed and the distal end of an axially movable member in a partially advanced position.

FIG. 13 shows a perspective view of one example embodiment of the end effector 326 with the jaws 364A, 364B open, while FIG. 14 shows a perspective view of one example embodiment of the end effector 326 with the jaws 364A, 364B closed. As noted above, the end effector 326 may comprise the upper first jaw 364A and the lower second jaw 364B, which may be straight or curved. The first jaw 364A and the second jaw 364B may each comprise an elongated slot or channel 362A and 362B, respectively, disposed outwardly along their respective middle portions. Further, the first jaw 364A and second jaw 364B may each have tissue-gripping elements, such as teeth 363, disposed on the inner portions of first jaw 364A and second jaw 364B. The first jaw 364A may comprise an upper first outward-facing surface 369A and an upper first energy delivery surface 365A. The second jaw 364B may comprise a lower second outward-facing surface 369B and a lower second energy delivery surface 365B. The first energy delivery surface 365A and the second energy delivery surface 365B may both extend in a "U" shape about the distal end of the end effector 326.

Figure 15:
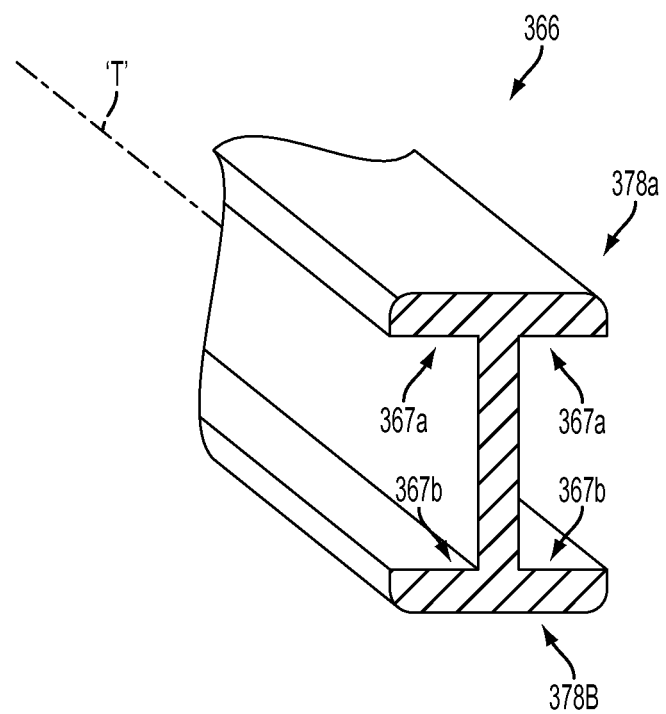
FIG. 15 illustrates a perspective view of one embodiment of the axially moveable member of the surgical instrument of FIG. 11.

The lever arm 321 of the handle 312 (FIG. 12) may be adapted to actuate the axially moveable member 378, which may also function as a jaw-closing mechanism. For example, the axially moveable member 378 may be urged distally as the lever arm 321 is pulled proximally along the path 33 via the shuttle 384, as shown in FIG. 12 and discussed above. FIG. 15 is a perspective view of one example embodiment of the axially moveable member 378 of the surgical instrument 310. The axially moveable member 378 may comprise one or several pieces, but in any event, may be movable or translatable with respect to the elongated shaft 314 and/or the jaws 364A, 364B. Also, in at least one example embodiment, the axially moveable member 378 may be made of 17-4 precipitation hardened stainless steel. The distal end of axially moveable member 378 may comprise a flanged "I"-beam configured to slide within the channels 362A and 362B in jaws 364A and 364B. The axially moveable member 378 may slide within the channels 362A, 362B to open and close the first jaw 364A and the second jaw 364B. The distal end of the axially moveable member 378 may also comprise an upper flange or "c"-shaped portion 378A and a lower flange or "c"-shaped portion 378B. The flanges 378A and 378B respectively define inner cam surfaces 367A and 367B for engaging outward facing surfaces of the first jaw 364A and the second jaw 364B. The opening-closing of jaws 364A and 364B can apply very high compressive forces on tissue using cam mechanisms which may include movable "I-beam" axially moveable member 378 and the outward facing surfaces 369A, 369B of jaws 364A, 364B.

More specifically, referring now to FIGS. 13-15, collectively, the inner cam surfaces 367A and 367B of the distal end of axially moveable member 378 may be adapted to slidably engage the first outward-facing surface 369A and the second outward-facing surface 369B of the first jaw 364A and the second jaw 364B, respectively. The channel 362A within first jaw 364A and the channel 362B within the second jaw 364B may be sized and configured to accommodate the movement of the axially moveable member 378, which may comprise a tissue-cutting element 371, for example, comprising a sharp distal edge. FIG. 14, for example, shows the distal end of the axially moveable member 378 advanced at least partially through channels 362A and 362B (FIG. 13). The advancement of the axially moveable member 378 may close the end effector 326 from the open configuration shown in FIG. 13. In the closed position shown by FIG. 14, the upper first jaw 364A and lower second jaw 364B define a gap or dimension D between the first energy delivery surface 365A and second energy delivery surface 365B of first jaw 364A and second jaw 364B, respectively. In various embodiments, dimension D can equal from about 0.0005" to about 0.040", for example, and in some embodiments, between about 0.001" to about 0.010", for example. Also, the edges of the first energy delivery surface 365A and the second energy delivery surface 365B may be rounded to prevent the dissection of tissue.

Figure 16:
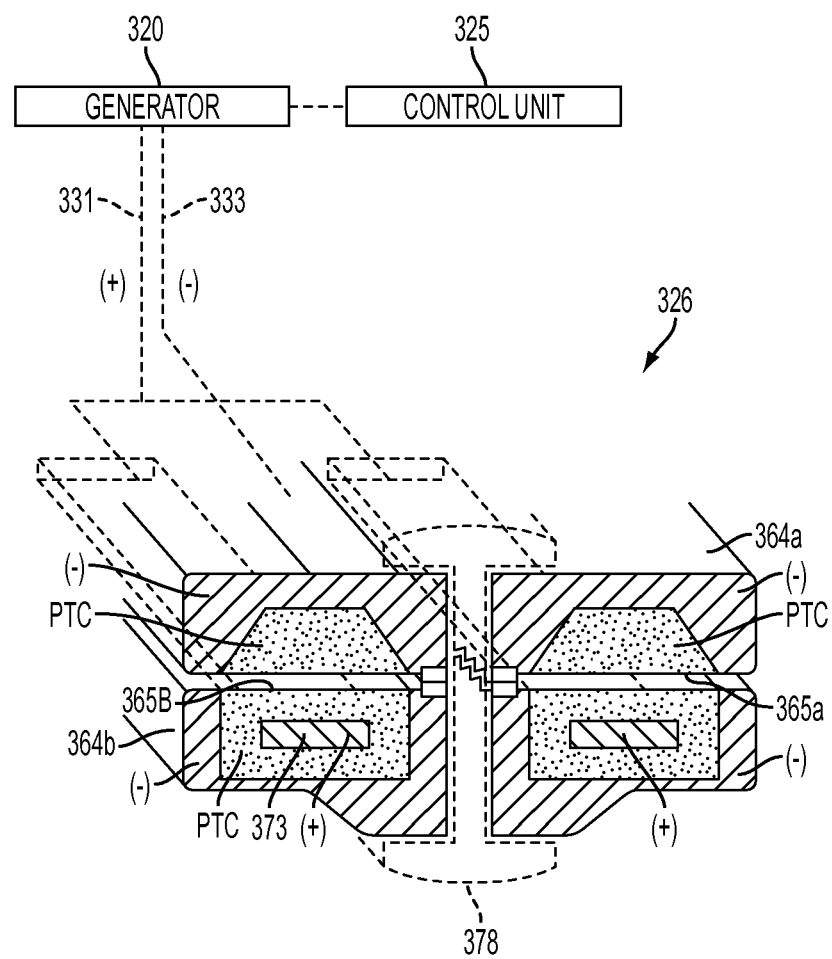
FIG. 16 illustrates a section view of one embodiment of the end effector of the surgical instrument of FIG. 11.

FIG. 16 is a section view of one example embodiment of the end effector 326 of the surgical instrument 310. The engagement, or tissue-contacting, surface 365B of the lower jaw 364B is adapted to deliver energy to tissue, at least in part, through a conductive-resistive matrix, such as a variable resistive positive temperature coefficient (PTC) body, as discussed in more detail below. At least one of the upper and lower jaws 364A, 364B may carry at least one electrode 373 configured to deliver the energy from the generator 320 to the captured tissue. The engagement, or tissue-contacting, surface 365A of upper jaw 364A may carry a similar conductive-resistive matrix (i.e., a PTC material), or in some embodiments the surface may be a conductive electrode or an insulative layer, for example. Alternatively, the engagement surfaces of the jaws can carry any of the energy delivery components disclosed in U.S. Pat. No. 6,773,409, filed Oct. 22, 2001, entitled ELECTROSURGICAL JAW STRUC- TURE FOR CONTROLLED ENERGY DELIVERY, the entire disclosure of which is incorporated herein by reference.

The first energy delivery surface 365A and the second energy delivery surface 365B may each be in electrical communication with the generator 320. The first energy delivery surface 365A and the second energy delivery surface 365B may be configured to contact tissue and deliver electrosurgical energy to captured tissue which are adapted to seal or weld the tissue. The control unit 325 regulates the electrical energy delivered by electrical generator 320 which in turn delivers electrosurgical energy to the first energy delivery surface 365A and the second energy delivery surface 365B. The energy delivery may be initiated by an activation button 328 (FIG. 12) operably engaged with the lever arm 321 and in electrical communication with the generator 320 via cable 322. In one example embodiment, the electrosurgical instrument 310 may be energized by the generator 320 by way of a foot switch 329 (FIG. 11). When actuated, the foot switch 216 triggers the generator 320 to deliver electrical energy to the end effector 326, for example. The control unit 325 may regulate the power generated by the generator 320 during activation. Although the foot switch 329 may be suitable in many circumstances, other suitable types of switches can be used.

As mentioned above, the electrosurgical energy delivered by electrical generator 320 and regulated, or otherwise controlled, by the control unit 325 may comprise radio frequency (RF) energy, or other suitable forms of electrical energy. Further, the opposing first and second energy delivery surfaces 365A and 365B may carry variable resistive positive temperature coefficient (PTC) bodies that are in electrical communication with the generator 320 and the control unit 325. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,312; and U.S. Pat. App. Pub. Nos. 2010/0036370 and 2009/0076506, all of which are incorporated herein in their entirety by reference and made a part of this specification.

In one example embodiment, the generator 320 may be implemented as an electrosurgery unit (ESU) capable of supplying power sufficient to perform bipolar electrosurgery using radio frequency (RF) energy. In one example embodiment, the ESU can be a bipolar ERBE ICC 350 sold by ERBE USA, Inc. of Marietta, Ga. In some embodiments, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the positive temperature coefficient (PTC) bodies and to the return electrode through the tissue. Thus, in various embodiments, the electrosurgical system 300 may comprise a supply path and a return path, wherein the captured tissue being treated completes, or closes, the circuit. In one example embodiment, the generator 320 may be a monopolar RF ESU and the electrosurgical instrument 310 may comprise a monopolar end effector 326 in which one or more active electrodes are integrated. For such a system, the generator 320 may require a return pad in intimate contact with the patient at a location remote from the operative site and/or other suitable return path. The return pad may be connected via a cable to the generator 320. In other embodiments, the operator 20 may provide sub-therapeutic RF energy levels for purposes of evaluating tissue conditions and providing feedback in the electrosurgical system 300. Such feedback may be employed to control the therapeutic RF energy output of the electrosurgical instrument 310.

During operation of electrosurgical instrument 300, the user generally grasps tissue, supplies energy to the captured tissue to form a weld or a seal (e.g., by actuating button 328 and/or pedal 216), and then drives a tissue-cutting element 371 at the distal end of the axially moveable member 378 through the captured tissue. According to various embodiments, the translation of the axial movement of the axially moveable member 378 may be paced, or otherwise controlled, to aid in driving the axially moveable member 378 at a suitable rate of travel. By controlling the rate of the travel, the likelihood that the captured tissue has been properly and functionally sealed prior to transection with the cutting element 371 is increased.

FIG. 17 is a perspective view of one example embodiment of a surgical instrument system comprising a cordless electrical energy surgical instrument 410. The electrosurgical system is similar to the electrosurgical system 300. The electrosurgical system can be configured to supply energy, such as electrical energy, ultrasonic energy, heat energy, or any combination thereof, to the tissue of a patient either independently or simultaneously as described in connection with FIGS. 1 and 11, for example. The electrosurgical instrument may utilize the end effector 326 and elongated shaft 314 described herein in conjunction with a cordless proximal handle 412. In one example embodiment, the handle 412 includes a generator circuit 420 (see FIG. 18A). The generator circuit 420 performs a function substantially similar to that of generator 320. In one example embodiment, the generator circuit 420 is coupled to a controller, such as a control circuit. In the illustrated embodiment, the control circuit is integrated into the generator circuit 420. In other embodiments, the control circuit may be separate from the generator circuit 420.

In one example embodiment, various electrodes in the end effector 326 (including jaws 364A, 364B thereof) may be coupled to the generator circuit 420. The control circuit may be used to activate the generator 420, which may serve as an electrical source. In various embodiments, the generator 420 may comprise an RF source, an ultrasonic source, a direct current source, and/or any other suitable type of electrical energy source, for example. In one example embodiment, a button 328 may be provided to activate the generator circuit 420 to provide energy to the end effectors 326, 326.

FIG. 18A is a side view of one example embodiment of the handle 412 of the cordless surgical instrument 410. In FIG. 18, the handle 412 is shown with half of a first handle body removed to illustrate various components within second handle body 434. The handle 412 may comprise a lever arm 424 (e.g., a trigger) which may be pulled along a path 33 around a pivot point. The lever arm 424 may be coupled to an axially moveable member 478 disposed within elongated shaft 314 by a shuttle operably engaged to an extension of lever arm 424. In one example embodiment, the lever arm 424 defines a shepherd's hook shape comprising a distal member 424a and a proximal member 424b.

In one example embodiment, the cordless electrosurgical instrument comprises a battery 437. The battery 437 provides electrical energy to the generator circuit 420. The battery 437 may be any battery suitable for driving the generator circuit 420 at the desired energy levels. In one example embodiment, the battery 437 is a 100 mAh, triple-cell Lithium Ion Polymer battery. The battery may be fully charged prior to use in a surgical procedure, and may hold a voltage of about 12.6V.

The battery 437 may have two fuses fitted to the cordless electrosurgical instrument 410, arranged in line with each battery terminal. In one example embodiment, a charging port 439 is provided to connect the battery 437 to a DC current source (not shown).

Figure 18B:
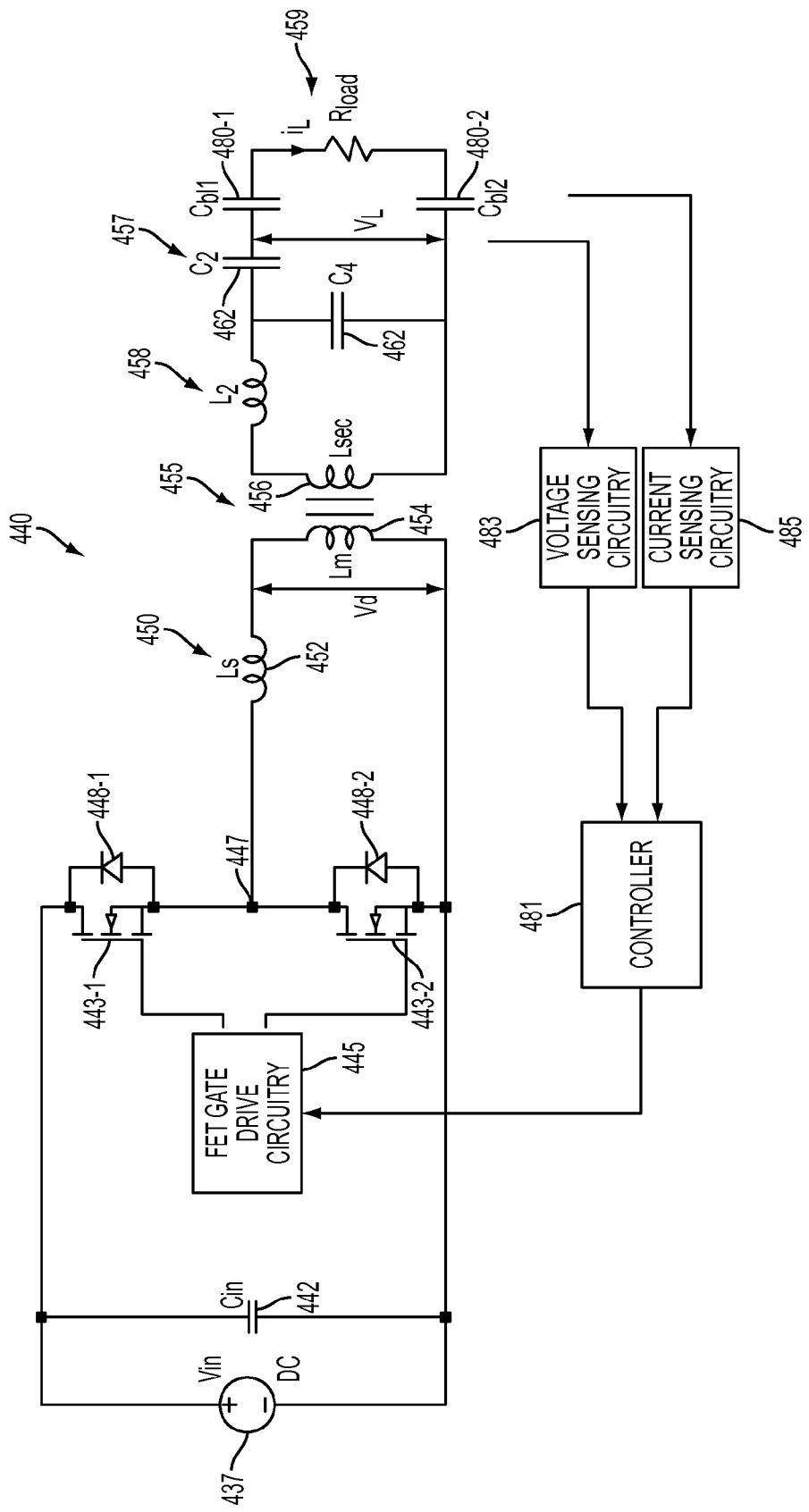
FIG. 18B illustrates an RF drive and control circuit, according to one embodiment.

The generator circuit 420 may be configured in any suitable manner. In some embodiments, the generator circuit comprises an RF drive and control circuit 440 FIG. 18B illustrates an RF drive and control circuit 440 according to one embodiment. FIG. 18B is a part schematic part block diagram illustrating the RF drive and control circuitry 440 used in this embodiment to generate and control the RF electrical energy supplied to the end effector 326. As will be explained in more detail below, in this embodiment, the drive circuitry 440 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the end effector 326. The way that this is achieved will become apparent from the following description.

As shown in FIG. 18B, the RF drive and control circuit 440 comprises the above described battery 437 are arranged to supply, in this example, about 0V and about 12V rails. An input capacitor ($C_{in}$) 442 is connected between the 0V and the 12V for providing a low source impedance. A pair of FET switches 443-1 and 443-2 (both of which are N-channel in this embodiment to reduce power losses) is connected in series between the 0V rail and the 12V rail. FET gate drive circuitry 805 is provided that generates two drive signals—one for driving each of the two FETs 443. The FET gate drive circuitry 445 generates drive signals that causes the upper FET (443-1) to be on when the lower FET (443-2) is off and vice versa. This causes the node 447 to be alternately connected to the 12V rail (when the FET 443-1 is switched on) and the 0V rail (when the FET 443-2 is switched on). FIG. 18B also shows the internal parasitic diodes 448-1 and 448-2 of the corresponding FETs 443, which conduct during any periods that the FETs 443 are open.

As shown in FIG. 18B, the node 447 is connected to an inductor-inductor resonant circuit 450 formed by inductor $L_s$ 452 and inductor $L_m$ 454. The FET gate driving circuitry 445 is arranged to generate drive signals at a drive frequency ($f_d$) that opens and crosses the FET switches 443 at the resonant frequency of the parallel resonant circuit 450. As a result of the resonant characteristic of the resonant circuit 450, the square wave voltage at node 447 will cause a substantially sinusoidal current at the drive frequency ($f_d$) to flow within the resonant circuit 450. As illustrated in FIG. 18B, the inductor $L_m$ 454 is the primary of a transformer 455, the secondary of which is formed by inductor $L_{sec}$ 456. The inductor $L_{sec}$ 456 of the transformer 455 secondary is connected to an inductor-capacitor-capacitor parallel resonant circuit 457 formed by inductor $L_2$ 458, capacitor $C_4$ 460, and capacitor $C_2$ 462. The transformer 455 up-converts the drive voltage ($V_d$) across the inductor $L_m$ 454 to the voltage that is applied to the output parallel resonant circuit 457. The load voltage ($V_L$) is output by the parallel resonant circuit 457 and is applied to the load (represented by the load resistance $R_{load}$ 459 in FIG. 18B) corresponding to the impedance of the forceps' jaws and any tissue or vessel gripped by the end effector 326. As shown in FIG. 18B, a pair of DC blocking capacitors $C_{bl}$ 480-1 and 480-2 is provided to prevent any DC signal being applied to the load 459.

In one embodiment, the transformer 455 may be implemented with a Core Diameter (mm), Wire Diameter (mm), and Gap between secondary windings in accordance with the following specifications:

Core Diameter, D (mm)
$D = 19.9 \times 10^{-3}$
Wire diameter, W (mm) for 22 AWG wire
$W = 7.366 \times 10^{-4}$
Gap between secondary windings, in gap=0.125
$G = gap/25.4$ In this embodiment, the amount of electrical power supplied to the end effector 326 is controlled by varying the frequency of the switching signals used to switch the FETs 443. This works because the resonant circuit 450 acts as a frequency dependent (loss less) attenuator. The closer the drive signal is to the resonant frequency of the resonant circuit 450, the less the drive signal is attenuated. Similarly, as the frequency of the drive signal is moved away from the resonant frequency of the circuit 450, the more the drive signal is attenuated and so the power supplied to the load reduces. In this embodiment, the frequency of the switching signals generated by the FET gate drive circuitry 445 is controlled by a controller 481 based on a desired power to be delivered to the load 459 and measurements of the load voltage ($V_L$) and of the load current ($I_L$) obtained by conventional voltage sensing circuitry 483 and current sensing circuitry 485. The way that the controller 481 operates will be described in more detail below.

In one embodiment, the voltage sensing circuitry 483 and the current sensing circuitry 485 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 483 and the current sensing circuitry 485. In one-embodiment, a step-down regulator (e.g., LT3502 by Linear Technologies) may be employed by the power save circuit to reduce the supply voltage of the rail-to-rail amplifiers and thus extend the life of the battery 437.

Figure 18C:
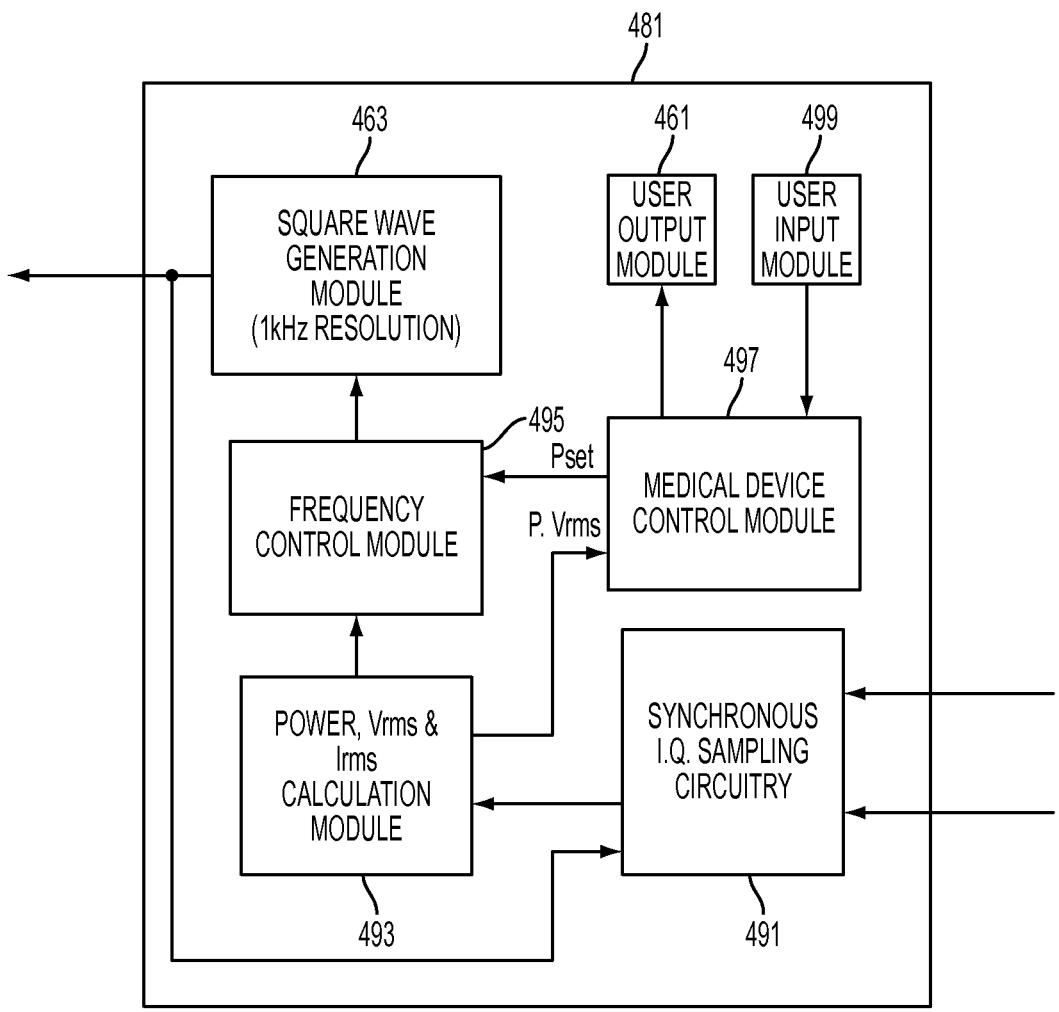
FIG. 18C illustrates the main components of the controller, according to one embodiment.

FIG. 18C illustrates the main components of the controller 481, according to one embodiment. In the embodiment illustrated in FIG. 18C, the controller 481 is a microprocessor based controller and so most of the components illustrated in FIG. 16 are software based components. Nevertheless, a hardware based controller 481 may be used instead. As shown, the controller 481 includes synchronous I,Q sampling circuitry 491 that receives the sensed voltage and current signals from the sensing circuitry 483 and 485 and obtains corresponding samples which are passed to a power, $V_{rms}$ and $I_{rms}$ calculation module 493. The calculation module 493 uses the received samples to calculate the RMS voltage and RMS current applied to the load 459 (FIG. 18B; end effector 326 and tissue/vessel gripped thereby) and from them the power that is presently being supplied to the load 459. The determined values are then passed to a frequency control module 495 and a medical device control module 497. The medical device control module 497 uses the values to determine the present impedance of the load 459 and based on this determined impedance and a pre-defined algorithm, determines what set point power ($P_{set}$) should be applied to the frequency control module 495. The medical device control module 497 is in turn controlled by signals received from a user input module 499 that receives inputs from the user (for example pressing buttons or activating the control levers 114, 110 on the handle 104) and also controls output devices (lights, a display, speaker or the like) on the handle 104 via a user output module 461.

The frequency control module 495 uses the values obtained from the calculation module 493 and the power set point ($P_{set}$) obtained from the medical device control module 497 and predefined system limits (to be explained below), to determine whether or not to increase or decrease the applied frequency. The result of this decision is then passed to a square wave generation module 463 which, in this embodiment, increments or decrements the frequency of a square wave signal that it generates by 1 kHz, depending on the received decision. As those skilled in the art will appreciate, in an alternative embodiment, the frequency control module 495 may determine not only whether to increase or decrease the frequency, but also the amount of frequency change required. In this case, the square wave generation module 463 would generate the corresponding square wave signal with the desired frequency shift. In this embodiment, the square wave signal generated by the square wave generation module 463 is output to the FET gate drive circuitry 445, which amplifies the signal and then applies it to the FET 443-1. The FET gate drive circuitry 445 also inverts the signal applied to the FET 443-1 and applies the inverted signal to the FET 443-2.

The electrosurgical instrument 410 may comprise additional features as discussed with respect to electrosurgical system 300. Those skilled in the art will recognize that electrosurgical instrument 410 may include a rotation knob 348, an elongated shaft 314, and an end effector 326. These elements function in a substantially similar manner to that discussed above with respect to the electrosurgical system 300. In one example embodiment, the cordless electrosurgical instrument 410 may include visual indicators 435. The visual indicators 435 may provide a visual indication signal to an operator. In one example embodiment, the visual indication signal may alert an operator that the device is on, or that the device is applying energy to the end effector. Those skilled in the art will recognize that the visual indicators 435 may be configured to provide information on multiple states of the device.

Over the years a variety of minimally invasive robotic (or "telesurgical") systems have been developed to increase surgical dexterity as well as to permit a surgeon to operate on a patient in an intuitive manner. Robotic surgical systems can be used with many different types of surgical instruments including, for example, ultrasonic or electrosurgical instruments, as described herein. Example robotic systems include those manufactured by Intuitive Surgical, Inc., of Sunnyvale, Calif., U.S.A. Such systems, as well as robotic systems from other manufacturers, are disclosed in the following U.S. Patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,231,565, entitled "Robotic Arm DLUS For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524,320, entitled "Mechanical Actuator Interface System For Robotic Surgical Tools", U.S. Pat. No. 7,691,098, entitled Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Writed Monopolar Electrosurgical End Effectors".

Many of such systems, however, have in the past been unable to generate the magnitude of forces required to effectively cut and fasten tissue.

FIGS. 19-46C illustrate example embodiments of robotic surgical systems. In some embodiments, the disclosed robotic surgical systems may utilize the ultrasonic or electrosurgical instruments described herein. Those skilled in the art will appreciate that the illustrated robotic surgical systems are not limited to only those instruments described herein, and may utilize any compatible surgical instruments. Those skilled in the art will further appreciate that while various embodiments described herein may be used with the described robotic surgical systems, the disclosure is not so limited, and may be used with any compatible robotic surgical system.

Figure 19:
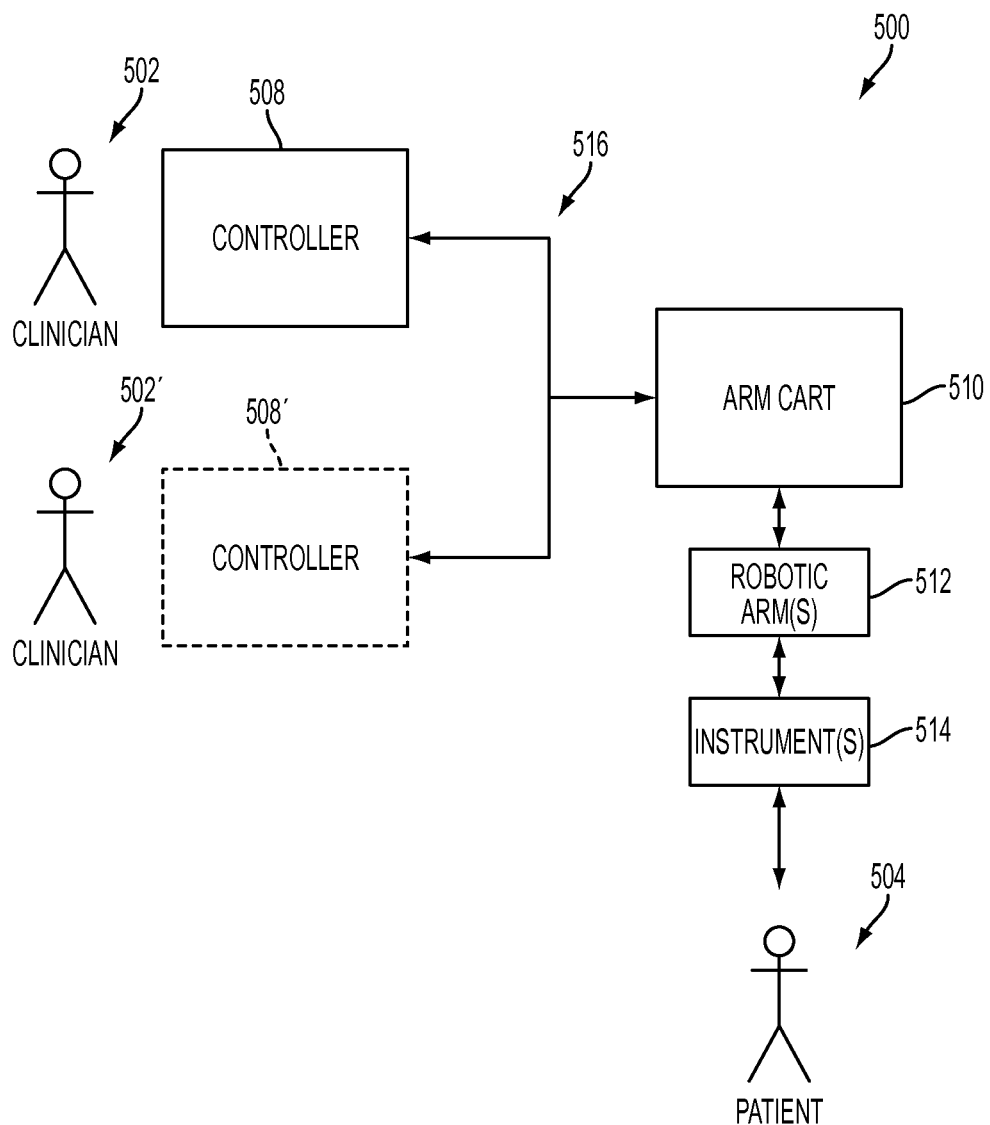
FIG. 19 illustrates a block diagram of one embodiment of a robotic surgical system.

FIGS. 19-25 illustrate the structure and operation of several example robotic surgical systems and components thereof. FIG. 19 shows a block diagram of an example robotic surgical system 500. The system 500 comprises at least one controller 508 and at least one arm cart 510. The arm cart 510 may be mechanically coupled to one or more robotic manipulators or arms, indicated by box 512. Each of the robotic arms 512 may comprise one or more surgical instruments 514 for performing various surgical tasks on a patient 504. Operation of the arm cart 510, including the arms 512 and instruments 514 may be directed by a clinician 502 from a controller 508. In some embodiments, a second controller 508', operated by a second clinician 502' may also direct operation of the arm cart 510 in conjunction with the first clinician 502'. For example, each of the clinicians 502, 502' may control different arms 512 of the cart or, in some cases, complete control of the arm cart 510 may be passed between the clinicians 502, 502'. In some embodiments, additional arm carts (not shown) may be utilized on the patient 504. These additional arm carts may be controlled by one or more of the controllers 508, 508'. The arm cart(s) 510 and controllers 508, 508' may be in communication with one another via a communications link 516, which may be any suitable type of wired or wireless communications link carrying any suitable type of signal (e.g., electrical, optical, infrared, etc.) according to any suitable communications protocol. Example implementations of robotic surgical systems, such as the system 500, are disclosed in U.S. Pat. No. 7,524,320 which has been herein incorporated by reference. Thus, various details of such devices will not be described in detail herein beyond that which may be necessary to understand various embodiments of the claimed device.

Figure 20:
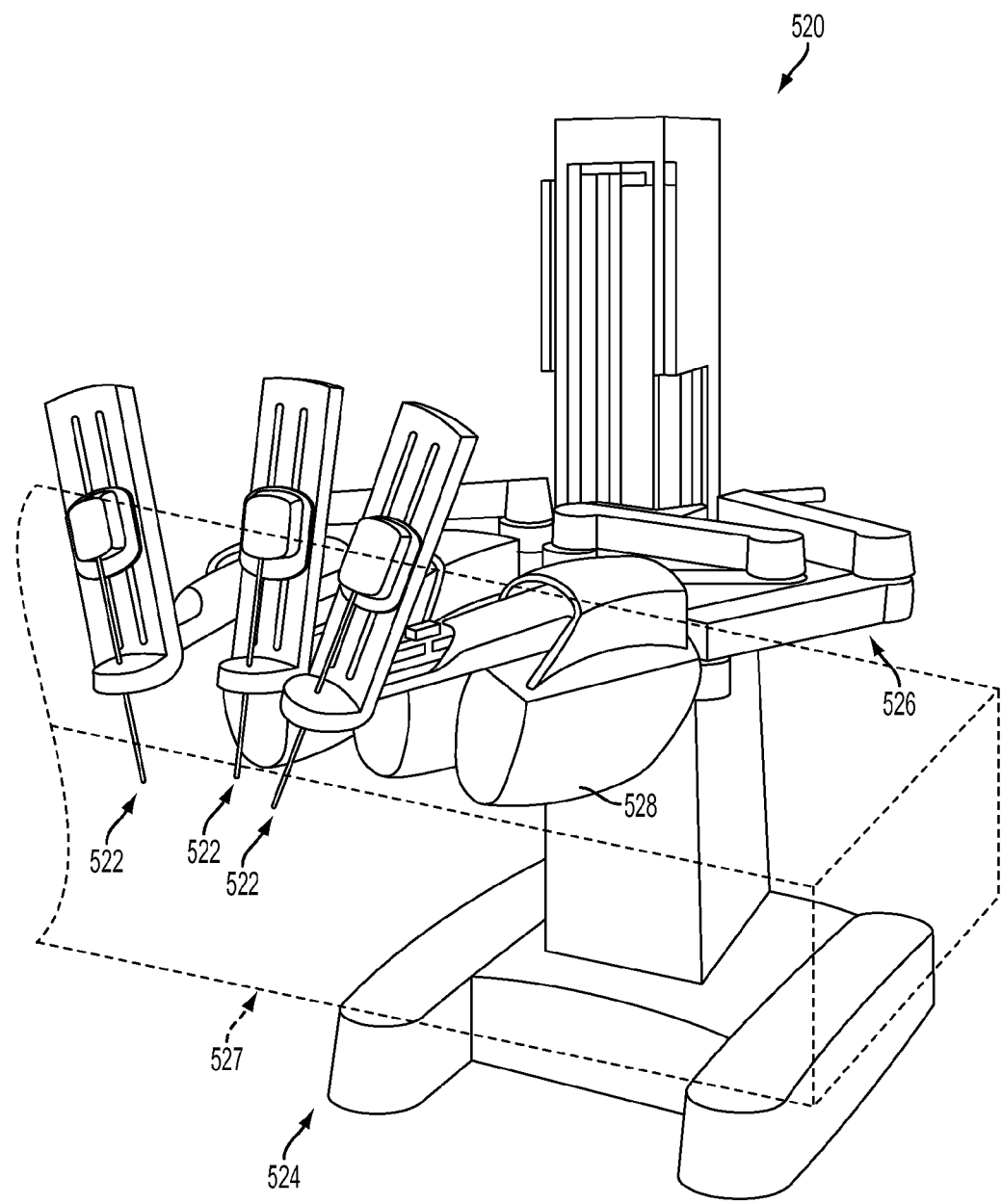
FIG. 20 illustrates one embodiment of a robotic arm cart.

FIG. 20 shows one example embodiment of a robotic arm cart 520. The robotic arm cart 520 is configured to actuate a plurality of surgical instruments or instruments, generally designated as 522 within a work envelope 527. Various robotic surgery systems and methods employing master controller and robotic arm cart arrangements are disclosed in U.S. Pat. No. 6,132,368, entitled "Multi-Component Telepresence System and Method", the full disclosure of which is incorporated herein by reference. In various forms, the robotic arm cart 520 includes a base 524 from which, in the illustrated embodiment, three surgical instruments 522 are supported. In various forms, the surgical instruments 522 are each supported by a series of manually articulatable linkages, generally referred to as set-up joints 526, and a robotic manipulator 528. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 520. Cart 520 will generally have dimensions suitable for transporting the cart 520 between operating rooms. The cart 520 may be configured to typically fit through standard operating room doors and onto standard hospital elevators. In various forms, the cart 520 would preferably have a weight and include a wheel (or other transportation) system that allows the cart 520 to be positioned adjacent an operating table by a single attendant.

Figure 21:
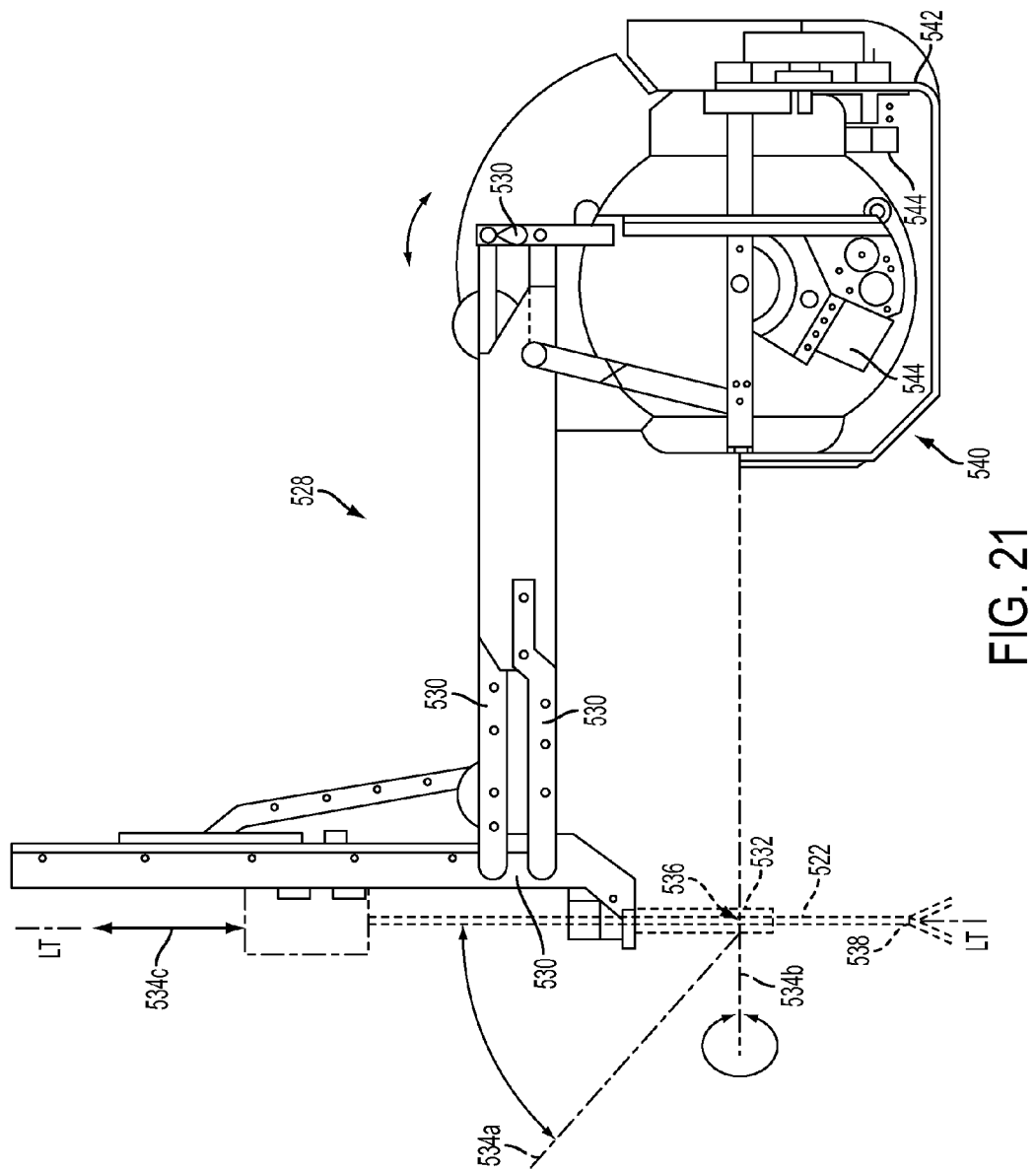
FIG. 21 illustrates one embodiment of the robotic manipulator of the robotic arm cart of FIG. 20.

FIG. 21 shows one example embodiment of the robotic manipulator 528 of the robotic arm cart 520. In the example shown in FIG. 21, the robotic manipulators 528 may include a linkage 530 that constrains movement of the surgical instrument 522. In various embodiments, linkage 530 includes rigid links coupled together by rotational joints in a parallelogram arrangement so that the surgical instrument 522 rotates around a point in space 532, as more fully described in issued U.S. Pat. No. 5,817,084, the full disclosure of which is herein incorporated by reference. The parallelogram arrangement constrains rotation to pivoting about an axis 534*a*, sometimes called the pitch axis. The links supporting the parallelogram linkage are pivotally mounted to set-up joints 526 (FIG. 20) so that the surgical instrument 522 further rotates about an axis 534*b*, sometimes called the yaw axis. The pitch and yaw axes 534*a*, 534*b* intersect at the remote center 536, which is aligned along a shaft 538 of the surgical instrument 522. The surgical instrument 522 may have further degrees of driven freedom as supported by manipulator 540, including sliding motion of the surgical instrument 522 along the longitudinal instrument axis "LT-LT". As the surgical instrument 522 slides along the instrument axis LT-LT relative to manipulator 540 (arrow 534*c*), remote center 536 remains fixed relative to base 542 of manipulator 540. Hence, the entire manipulator 540 is generally moved to re-position remote center 536. Linkage 530 of manipulator 540 is driven by a series of motors 544. These motors 544 actively move linkage 530 in response to commands from a processor of a control system. As will be discussed in further detail below, motors 544 are also employed to manipulate the surgical instrument 522.

Figure 22:
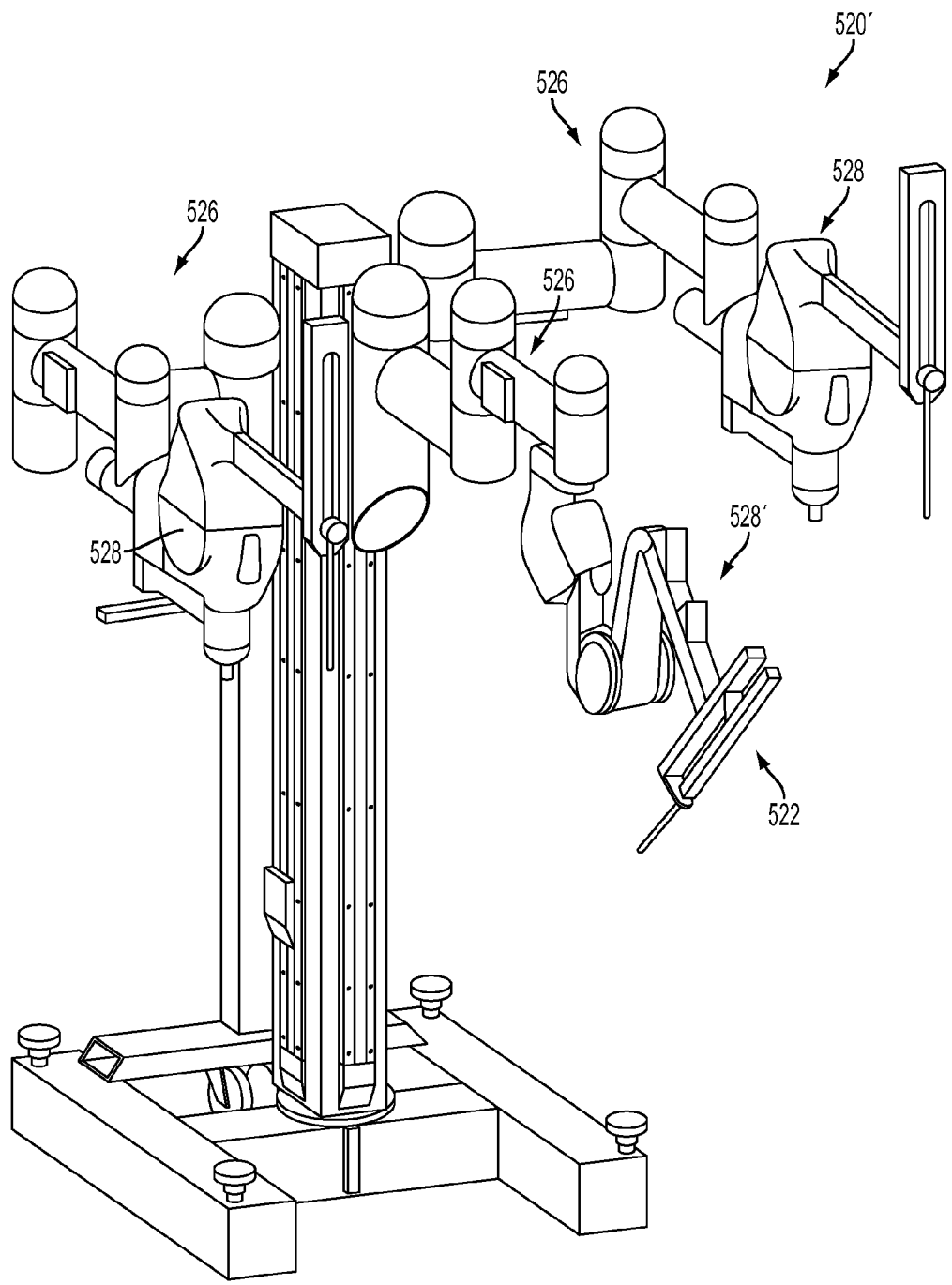
FIG. 22 illustrates one embodiment of a robotic arm cart having an alternative set-up joint structure.

FIG. 22 shows one example embodiment of a robotic arm cart 520' having an alternative set-up joint structure. In this example embodiment, a surgical instrument 522 is supported by an alternative manipulator structure 528' between two tissue manipulation instruments. Those of ordinary skill in the art will appreciate that various embodiments of the claimed device may incorporate a wide variety of alternative robotic structures, including those described in U.S. Pat. No. 5,878,193, the full disclosure of which is incorporated herein by reference. Additionally, while the data communication between a robotic component and the processor of the robotic surgical system is primarily described herein with reference to communication between the surgical instrument 522 and the controller, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 23:
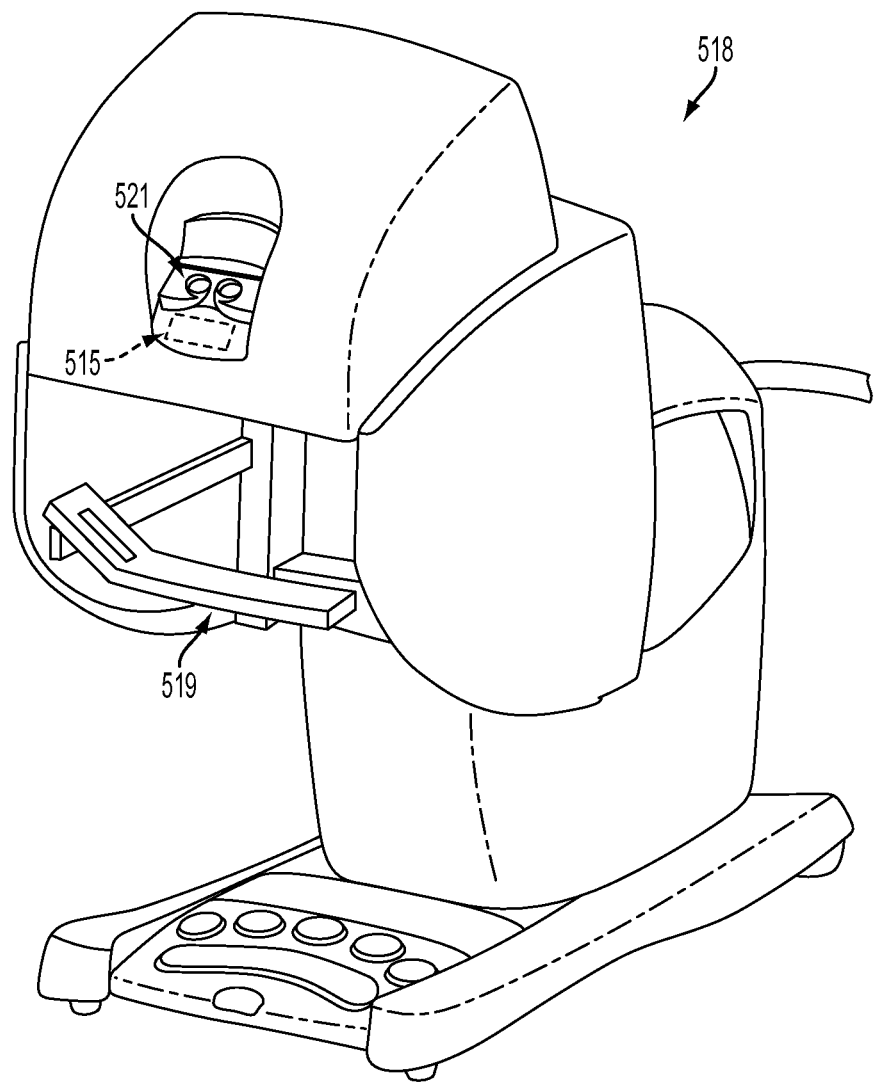
FIG. 23 illustrates one embodiment of a controller that may be used in conjunction with a robotic arm cart, such as the robotic arm carts of FIGS. 19-22.

FIG. 23 shows one example embodiment of a controller 518 that may be used in conjunction with a robotic arm cart, such as the robotic arm carts 520, 520' depicted in FIGS. 20-22. The controller 518 generally includes master controllers (generally represented as 519 in FIG. 23) which are grasped by the clinician and manipulated in space while the clinician views the procedure via a stereo display 521. A surgeon feed back meter 515 may be viewed via the display 521 and provide the surgeon with a visual indication of the amount of force being applied to the cutting instrument or dynamic clamping member. The master controllers 519 generally comprise manual input devices which preferably move with multiple degrees of freedom, and which often further have a handle or trigger for actuating instruments (for example, for closing grasping saws, applying an electrical potential to an electrode, or the like).

Figure 24:
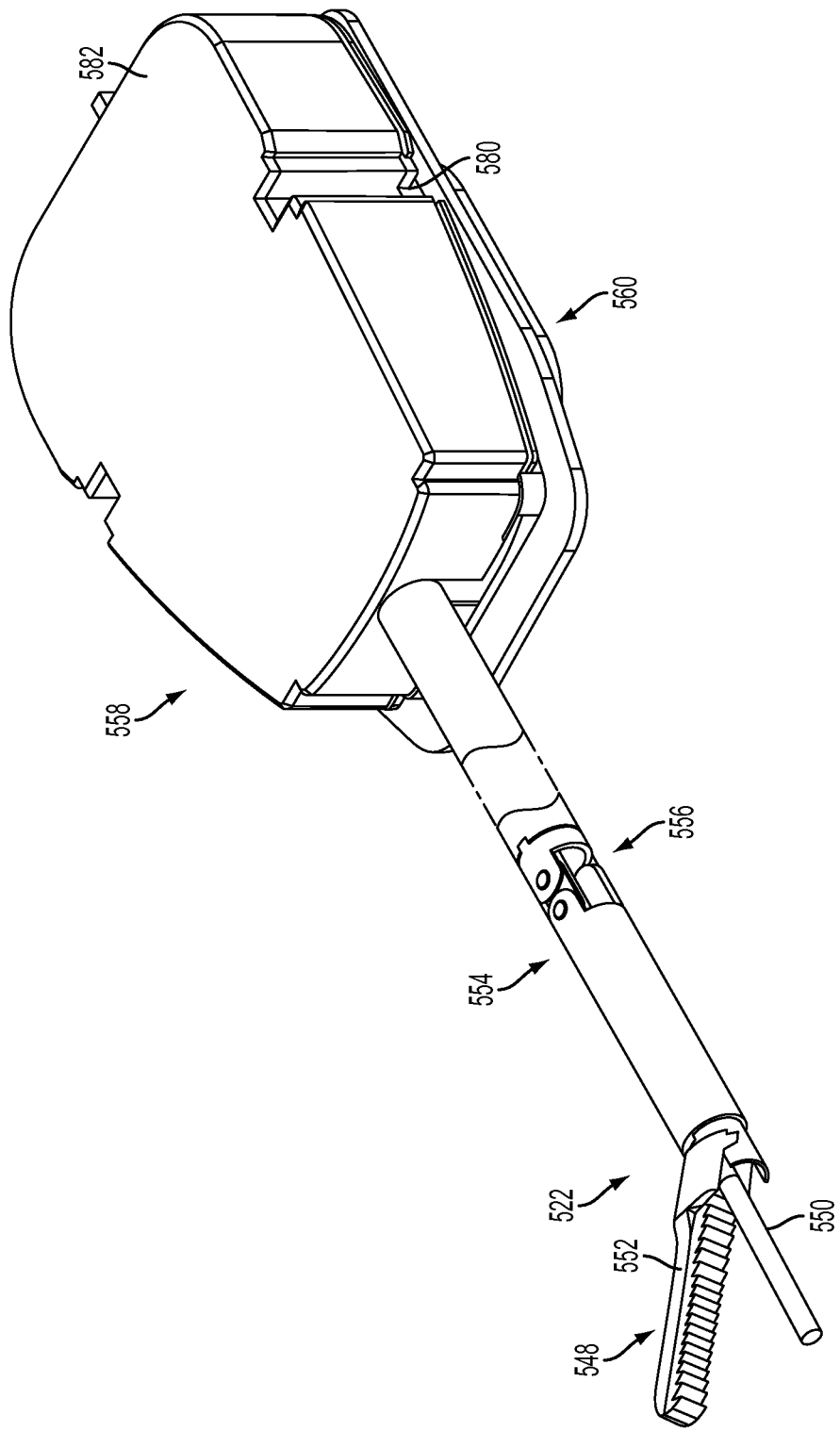
FIG. 24 illustrates one embodiment of an ultrasonic surgical instrument adapted for use with a robotic system.
Figure 25:
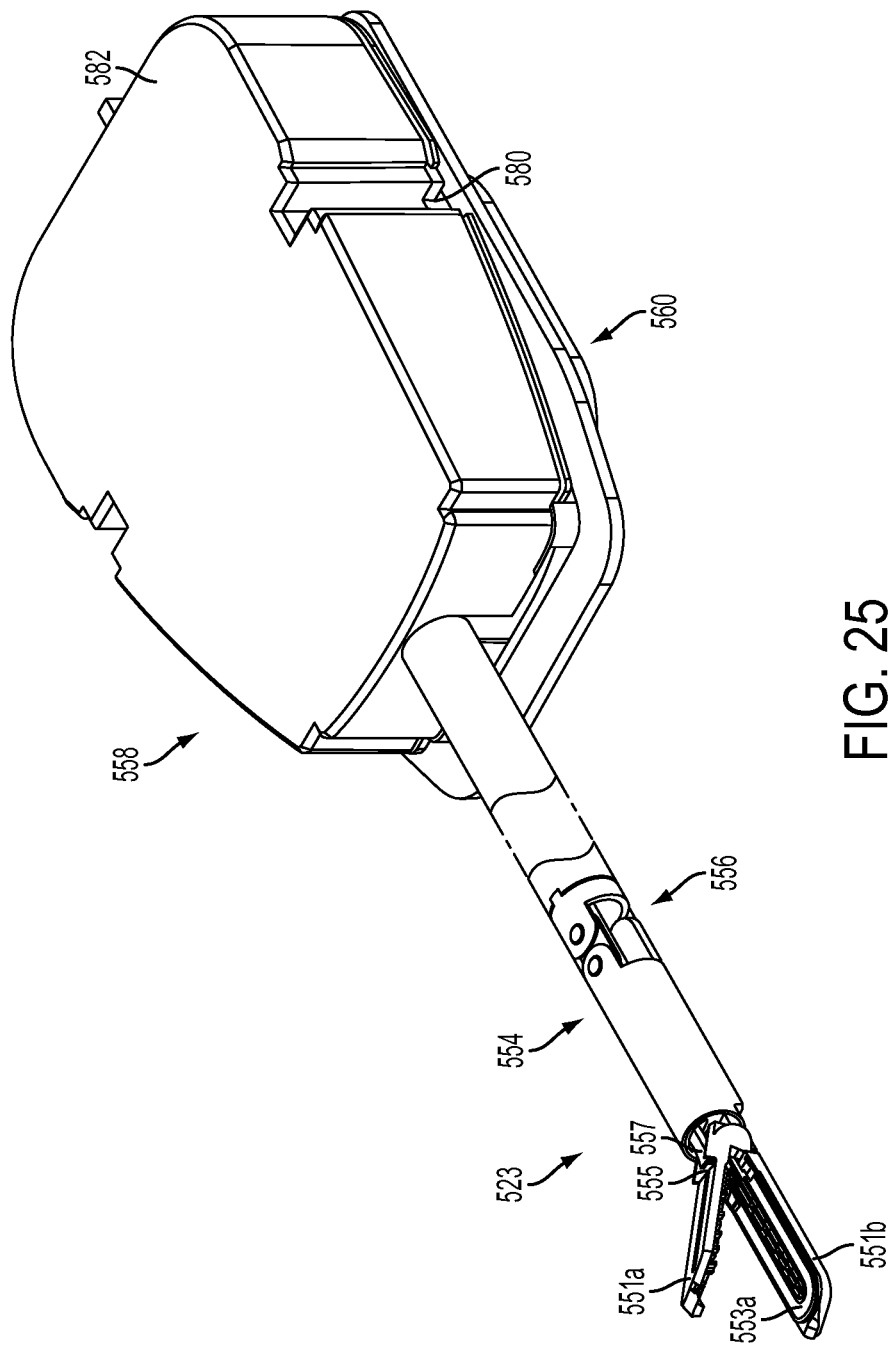
FIG. 25 illustrates one embodiment of an electrosurgical instrument adapted for use with a robotic system.
Figure 26:
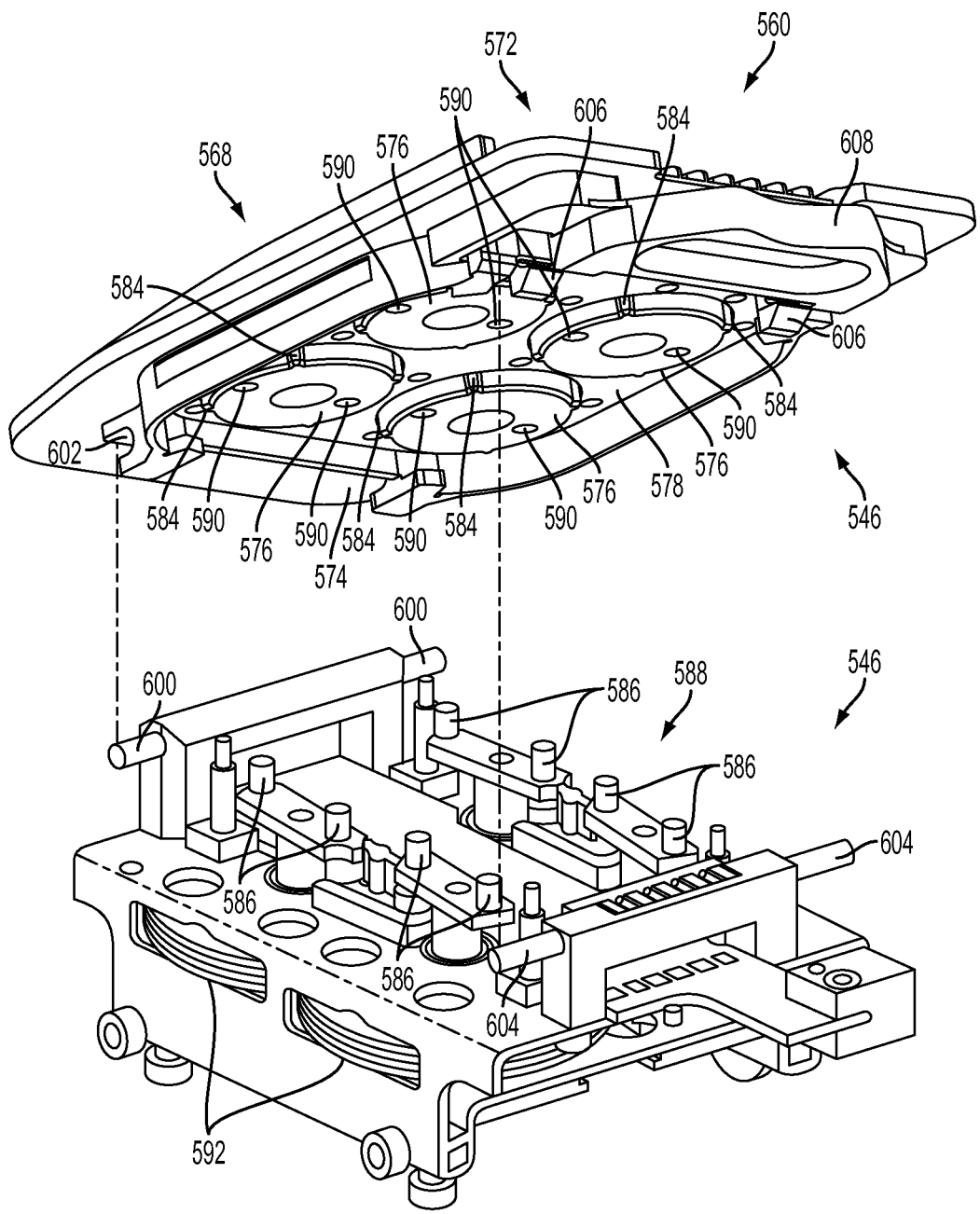
FIG. 26 illustrates one embodiment of an instrument drive assembly that may be coupled to surgical manipulators to receive and control the surgical instrument shown in FIG. 24.

FIG. 24 shows one example embodiment of an ultrasonic surgical instrument 522 adapted for use with a robotic surgical system. For example, the surgical instrument 522 may be coupled to one of the surgical manipulators 528, 528' described hereinabove. As can be seen in FIG. 24, the surgical instrument 522 comprises a surgical end effector 548 that comprises an ultrasonic blade 550 and clamp arm 552, which may be coupled to an elongated shaft assembly 554 that, in some embodiments, may comprise an articulation joint 556. FIG. 25 shows another example embodiment having an electrosurgical instrument 523 in place of the ultrasonic surgical instrument 522. The surgical instrument 523 comprises a surgical end effector 548 that comprises closable jaws 551A, 551B having energy deliver surfaces 553A, 553B for engaging and providing electrical energy to tissue between the jaws 551A, 551B. A tissue cutting element or knife 555 may be positioned at the distal end of an axially movable member 557 that may extend through the elongated shaft assembly 554 to the instrument mounting portion 558. FIG. 26 shows one example embodiment of an instrument drive assembly 546 that may be coupled to one of the surgical manipulators 528, 528' to receive and control the surgical instruments 522, 523. The instrument drive assembly 546 may also be operatively coupled to the controller 518 to receive inputs from the clinician for controlling the instrument 522, 523. For example, actuation (i.e., opening and closing) of the clamp arm 552, actuation (i.e., opening and closing) of the jaws 551A, 551B, actuation of the ultrasonic blade 550, extension of the knife 555 and actuation of the energy delivery surfaces 553A, 553B, etc. may be controlled through the instrument drive assembly 546 based on inputs from the clinician provided through the controller 518. The surgical instrument 522 is operably coupled to the manipulator by an instrument mounting portion, generally designated as 558. The surgical instruments 522 further include an interface 560 which mechanically and electrically couples the instrument mounting portion 558 to the manipulator.

Figure 27:
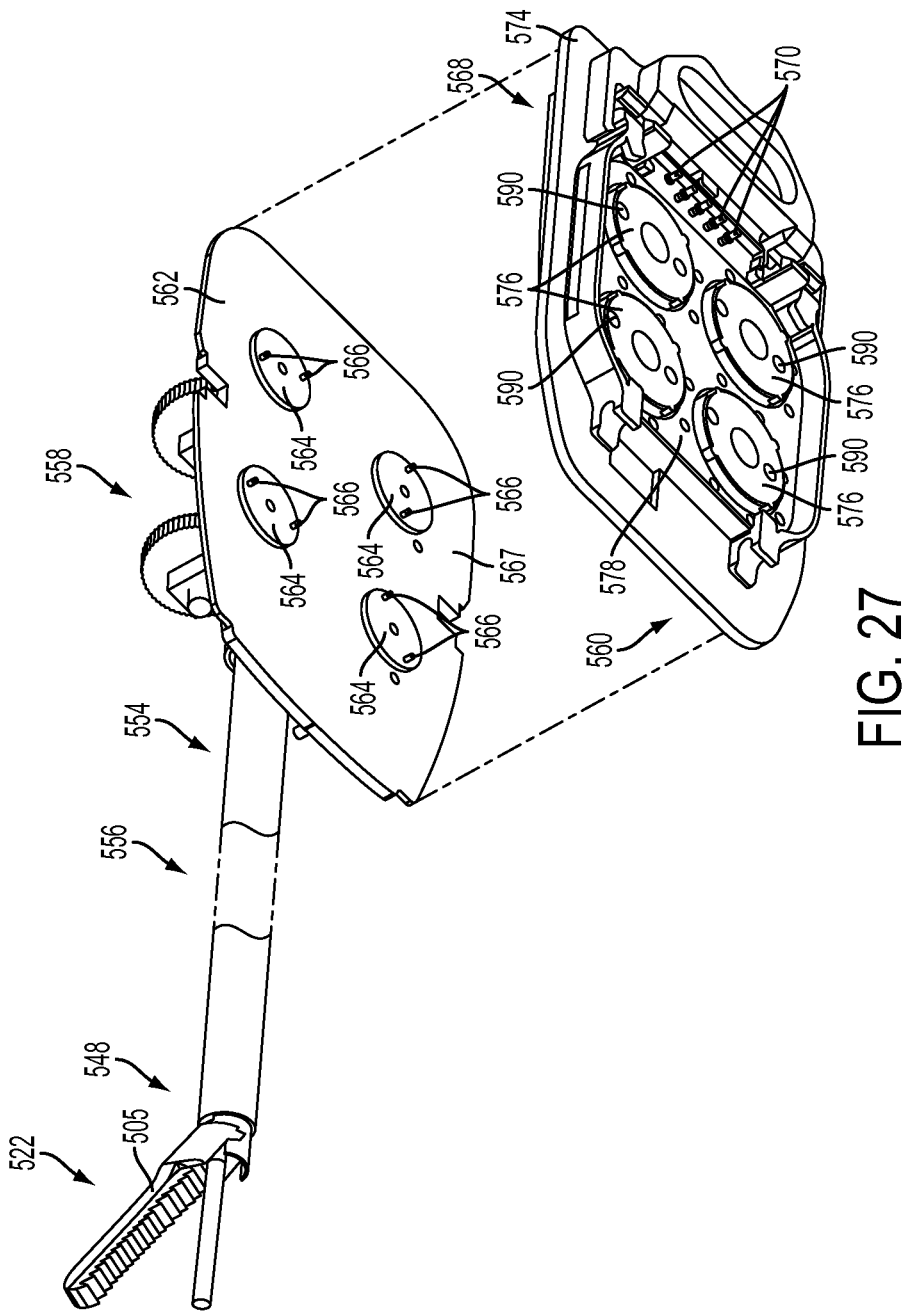
FIG. 27 illustrates another view of the instrument drive assembly embodiment of FIG. 26 including the surgical instrument of FIG. 24.
Figure 28:
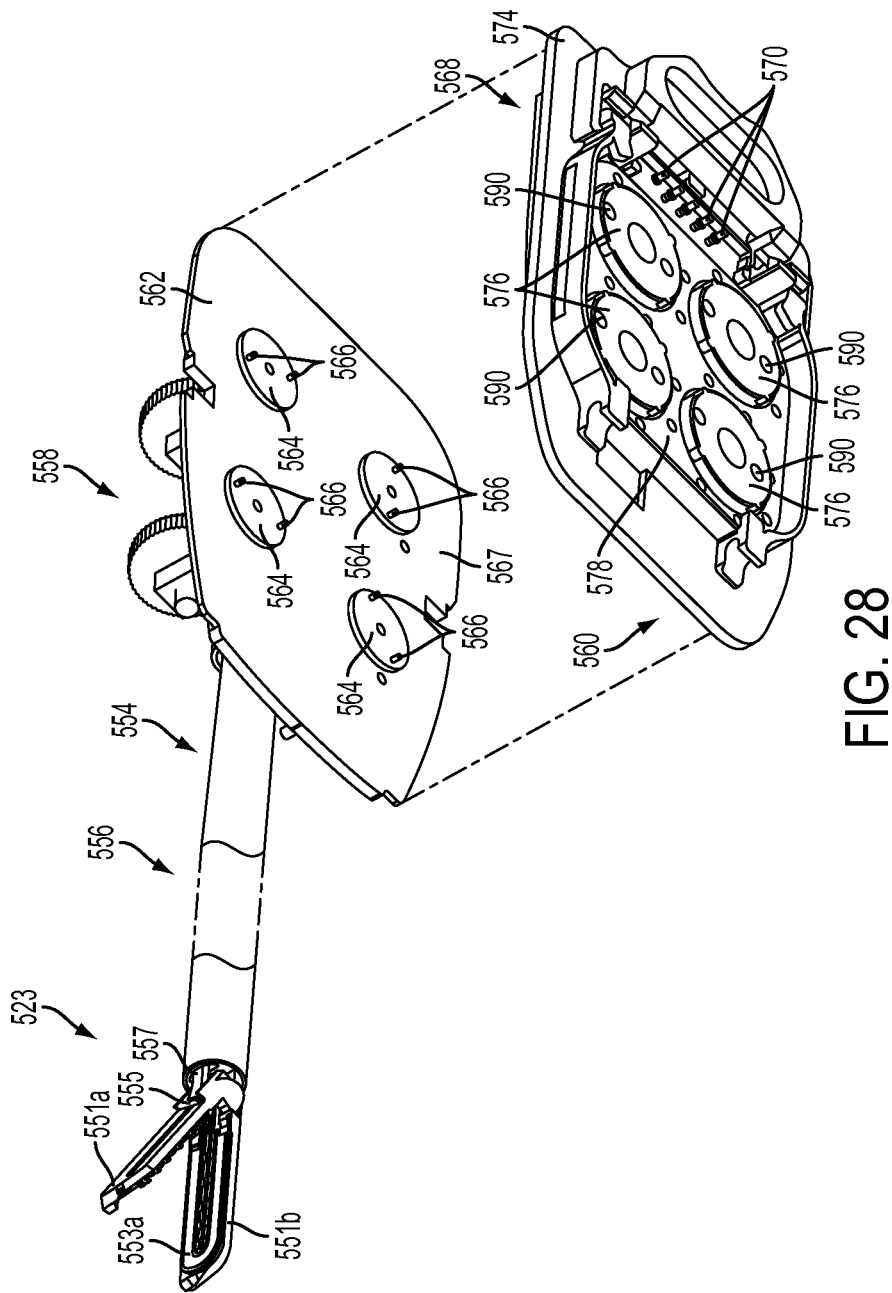
FIG. 28 illustrates another view of the instrument drive assembly embodiment of FIG. 26 including the electrosurgical instrument of FIG. 25.

FIG. 27 shows another view of the instrument drive assembly of FIG. 26 including the ultrasonic surgical instrument 522. FIG. 28 shows another view of the instrument drive assembly of FIG. 26 including the electrosurgical instrument 523. The instrument mounting portion 558 includes an instrument mounting plate 562 that operably supports a plurality of (four are shown in FIG. 26) rotatable body portions, driven discs or elements 564, that each include a pair of pins 566 that extend from a surface of the driven element 564. One pin 566 is closer to an axis of rotation of each driven elements 564 than the other pin 566 on the same driven element 564, which helps to ensure positive angular alignment of the driven element 564. The driven elements 564 and pints 566 may be positioned on an adapter side 567 of the instrument mounting plate 562.

Interface 560 also includes an adaptor portion 568 that is configured to mountingly engage the mounting plate 562 as will be further discussed below. The adaptor portion 568 may include an array of electrical connecting pins 570, which may be coupled to a memory structure by a circuit board within the instrument mounting portion 558. While interface 560 is described herein with reference to mechanical, electrical, and magnetic coupling elements, it should be understood that a wide variety of telemetry modalities might be used, including infrared, inductive coupling, or the like.

Figure 29:
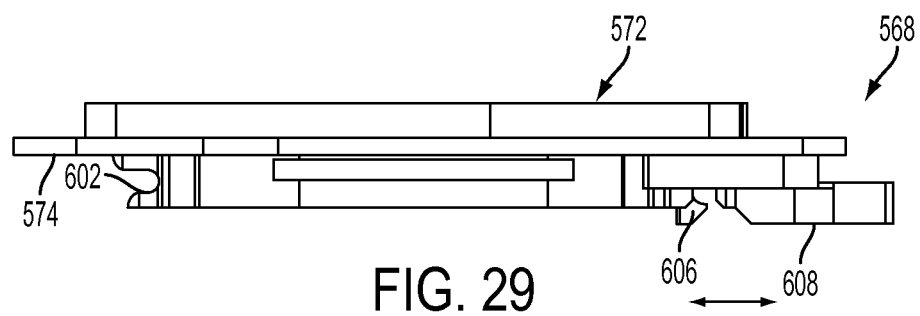
FIGS. 29-31 illustrate additional views of the adapter portion of the instrument drive assembly of FIG. 26.
Figure 30:
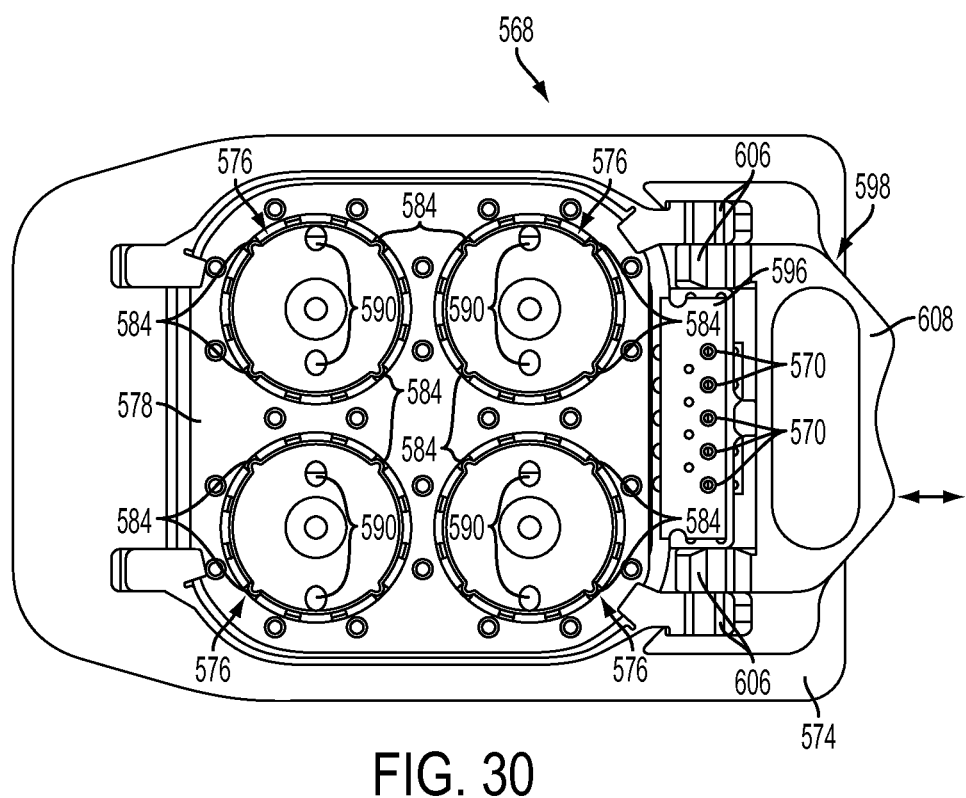
Figure 31:
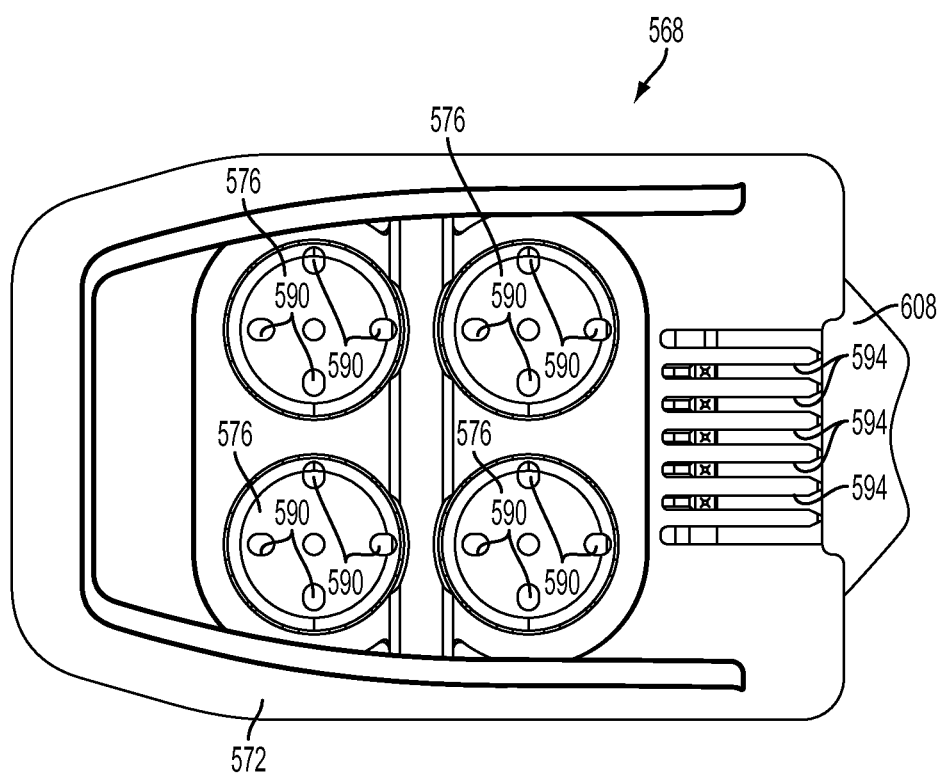

FIGS. 29-31 show additional views of the adapter portion 568 of the instrument drive assembly 546 of FIG. 26. The adapter portion 568 generally includes an instrument side 572 and a holder side 574 (FIG. 29). In various embodiments, a plurality of rotatable bodies 576 are mounted to a floating plate 578 which has a limited range of movement relative to the surrounding adaptor structure normal to the major surfaces of the adaptor 568. Axial movement of the floating plate 578 helps decouple the rotatable bodies 576 from the instrument mounting portion 558 when the levers 580 along the sides of the instrument mounting portion housing 582 are actuated (See FIGS. 24, 25) Other mechanisms/arrangements may be employed for releasably coupling the instrument mounting portion 558 to the adaptor 568. In at least one form, rotatable bodies 576 are resiliently mounted to floating plate 578 by resilient radial members which extend into a circumferential indentation about the rotatable bodies 576. The rotatable bodies 576 can move axially relative to plate 578 by deflection of these resilient structures. When disposed in a first axial position (toward instrument side 572) the rotatable bodies 576 are free to rotate without angular limitation. However, as the rotatable bodies 576 move axially toward instrument side 572, tabs 584 (extending radially from the rotatable bodies 576) laterally engage detents on the floating plates so as to limit angular rotation of the rotatable bodies 576 about their axes. This limited rotation can be used to help drivingly engage the rotatable bodies 576 with drive pins 586 of a corresponding instrument holder portion 588 of the robotic system, as the drive pins 586 will push the rotatable bodies 576 into the limited rotation position until the pins 586 are aligned with (and slide into) openings 590.

Openings 590 on the instrument side 572 and openings 590 on the holder side 574 of rotatable bodies 576 are configured to accurately align the driven elements 564 (FIGS. 27, 28) of the instrument mounting portion 558 with the drive elements 592 of the instrument holder 588. As described above regarding inner and outer pins 566 of driven elements 564, the openings 590 are at differing distances from the axis of rotation on their respective rotatable bodies 576 so as to ensure that the alignment is not 33 degrees from its intended position. Additionally, each of the openings 590 may be slightly radially elongated so as to fittingly receive the pins 566 in the circumferential orientation. This allows the pins 566 to slide radially within the openings 590 and accommodate some axial misalignment between the instrument 522, 523 and instrument holder 588, while minimizing any angular misalignment and backlash between the drive and driven elements. Openings 590 on the instrument side 572 may be offset by about 90 degrees from the openings 590 (shown in broken lines) on the holder side 574, as can be seen most clearly in FIG. 31.

Various embodiments may further include an array of electrical connector pins 570 located on holder side 574 of adaptor 568, and the instrument side 572 of the adaptor 568 may include slots 594 (FIG. 31) for receiving a pin array (not shown) from the instrument mounting portion 558. In addition to transmitting electrical signals between the surgical instrument 522, 523 and the instrument holder 588, at least some of these electrical connections may be coupled to an adaptor memory device 596 (FIG. 30) by a circuit board of the adaptor 568.

A detachable latch arrangement 598 may be employed to releasably affix the adaptor 568 to the instrument holder 588. As used herein, the term "instrument drive assembly" when used in the context of the robotic system, at least encompasses various embodiments of the adapter 568 and instrument holder 588 and which has been generally designated as 546 in FIG. 26. For example, as can be seen in FIG. 26, the instrument holder 588 may include a first latch pin arrangement 600 that is sized to be received in corresponding clevis slots 602 provided in the adaptor 568. In addition, the instrument holder 588 may further have second latch pins 604 that are sized to be retained in corresponding latch clevises 606 in the adaptor 568. See FIG. 30. In at least one form, a latch assembly 608 is movably supported on the adapter 568 and is biasable between a first latched position wherein the latch pins 600 are retained within their respective latch clevis 602 and an unlatched position wherein the second latch pins 604 may be into or removed from the latch clevises 606. A spring or springs (not shown) are employed to bias the latch assembly into the latched position. A lip on the instrument side 572 of adaptor 568 may slidably receive laterally extending tabs of instrument mounting housing 582.

As described the driven elements 564 may be aligned with the drive elements 592 of the instrument holder 588 such that rotational motion of the drive elements 592 causes corresponding rotational motion of the driven elements 564. The rotation of the drive elements 592 and driven elements 564 may be electronically controlled, for example, via the robotic arm 512, in response to instructions received from the clinician 502 via a controller 508. The instrument mounting portion 558 may translate rotation of the driven elements 564 into motion of the surgical instrument 522, 523.

Figure 32:
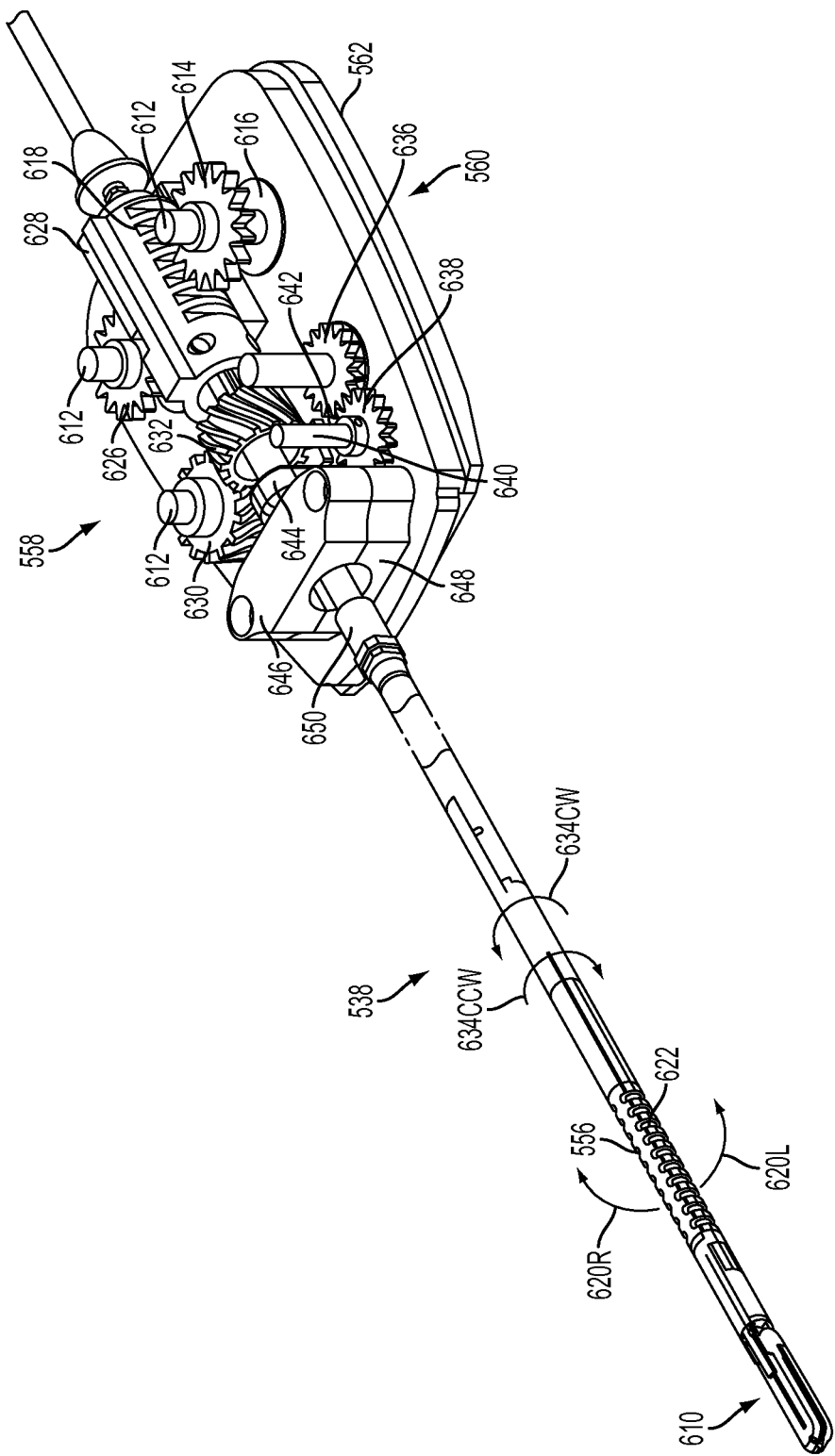
FIGS. 32-34 illustrate one embodiment of the instrument mounting portion of FIGS. 24-25 showing components for translating motion of the driven elements into motion of the surgical instrument.
Figure 33:
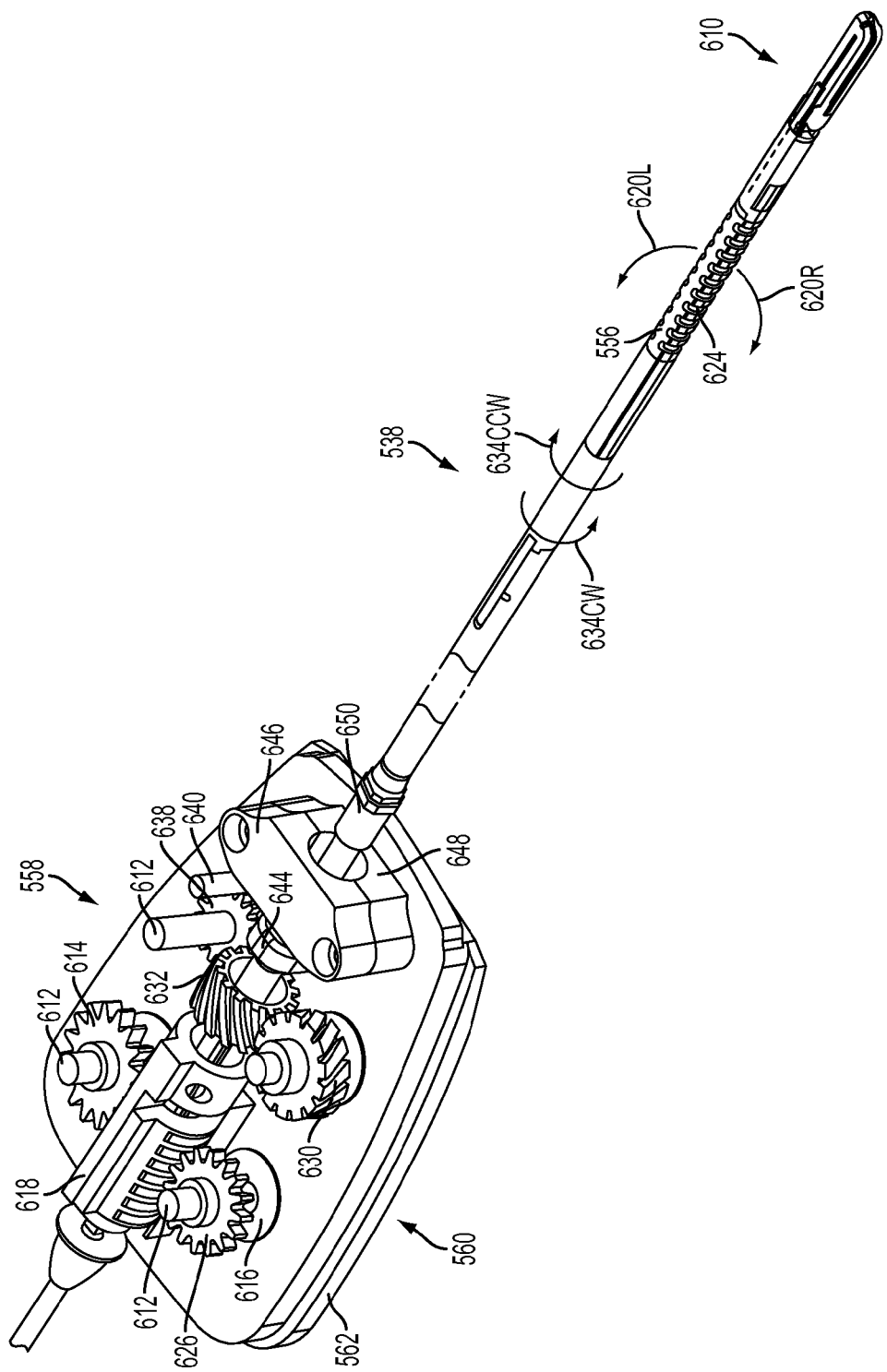
Figure 34:
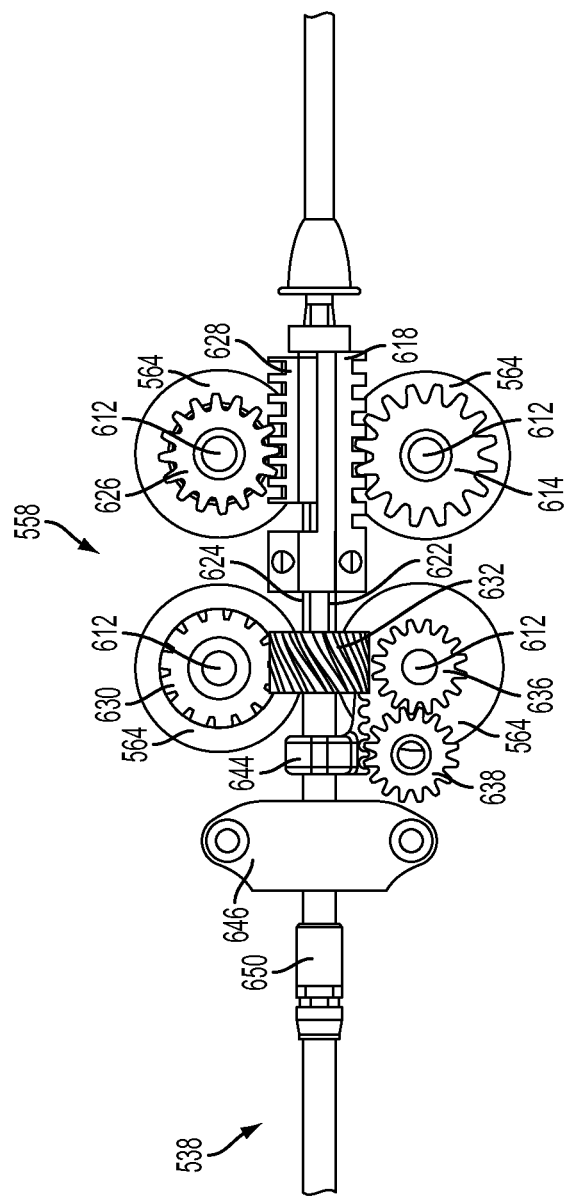

FIGS. 32-34 show one example embodiment of the instrument mounting portion 558 showing components for translating motion of the driven elements 564 into motion of the surgical instrument 522, 523. FIGS. 32-34 show the instrument mounting portion with a shaft 538 having a surgical end effector 610 at a distal end thereof. The end effector 610 may be any suitable type of end effector for performing a surgical task on a patient. For example, the end effector may be configured to provide RF and/or ultrasonic energy to tissue at a surgical site. The shaft 538 may be rotatably coupled to the instrument mounting portion 558 and secured by a top shaft holder 646 and a bottom shaft holder 648 at a coupler 650 of the shaft 538.

In one example embodiment, the instrument mounting portion 558 comprises a mechanism for translating rotation of the various driven elements 564 into rotation of the shaft 538, differential translation of members along the axis of the shaft (e.g., for articulation), and reciprocating translation of one or more members along the axis of the shaft 538 (e.g., for extending and retracting tissue cutting elements such as 555, overtubes and/or other components). In one example embodiment, the rotatable bodies 612 (e.g., rotatable spools) are coupled to the driven elements 564. The rotatable bodies 612 may be formed integrally with the driven elements 564. In some embodiments, the rotatable bodies 612 may be formed separately from the driven elements 564 provided that the rotatable bodies 612 and the driven elements 564 are fixedly coupled such that driving the driven elements 564 causes rotation of the rotatable bodies 612. Each of the rotatable bodies 612 is coupled to a gear train or gear mechanism to provide shaft articulation and rotation and clamp jaw open/close and knife actuation.

In one example embodiment, the instrument mounting portion 558 comprises a mechanism for causing differential translation of two or more members along the axis of the shaft 538. In the example provided in FIGS. 32-34, this motion is used to manipulate articulation joint 556. In the illustrated embodiment, for example, the instrument mounting portion 558 comprises a rack and pinion gearing mechanism to provide the differential translation and thus the shaft articulation functionality. In one example embodiment, the rack and pinion gearing mechanism comprises a first pinion gear 614 coupled to a rotatable body 612 such that rotation of the corresponding driven element 564 causes the first pinion gear 614 to rotate. A bearing 616 is coupled to the rotatable body 612 and is provided between the driven element 564 and the first pinion gear 614. The first pinion gear 614 is meshed to a first rack gear 618 to convert the rotational motion of the first pinion gear 614 into linear motion of the first rack gear 618 to control the articulation of the articulation section 556 of the shaft assembly 538 in a left direction 620L. The first rack gear 618 is attached to a first articulation band 622 (FIG. 32) such that linear motion of the first rack gear 618 in a distal direction causes the articulation section 556 of the shaft assembly 538 to articulate in the left direction 620L. A second pinion gear 626 is coupled to another rotatable body 612 such that rotation of the corresponding driven element 564 causes the second pinion gear 626 to rotate. A bearing 616 is coupled to the rotatable body 612 and is provided between the driven element 564 and the second pinion gear 626. The second pinion gear 626 is meshed to a second rack gear 628 to convert the rotational motion of the second pinion gear 626 into linear motion of the second rack gear 628 to control the articulation of the articulation section 556 in a right direction 620R. The second rack gear 628 is attached to a second articulation band 624 (FIG. 33) such that linear motion of the second rack gear 628 in a distal direction causes the articulation section 556 of the shaft assembly 538 to articulate in the right direction 620R. Additional bearings may be provided between the rotatable bodies and the corresponding gears. Any suitable bearings may be provided to support and stabilize the mounting and reduce rotary friction of shaft and gears, for example.

In one example embodiment, the instrument mounting portion 558 further comprises a mechanism for translating rotation of the driven elements 564 into rotational motion about the axis of the shaft 538. For example, the rotational motion may be rotation of the shaft 538 itself. In the illustrated embodiment, a first spiral worm gear 630 coupled to a rotatable body 612 and a second spiral worm gear 632 coupled to the shaft assembly 538. A bearing 616 (FIG. 17) is coupled to a rotatable body 612 and is provided between a driven element 564 and the first spiral worm gear 630. The first spiral worm gear 630 is meshed to the second spiral worm gear 632, which may be coupled to the shaft assembly 538 and/or to another component of the instrument 522, 523 for which longitudinal rotation is desired. Rotation may be caused in a clockwise (CW) and counter-clockwise (CCW) direction based on the rotational direction of the first and second spiral worm gears 630, 632. Accordingly, rotation of the first spiral worm gear 630 about a first axis is converted to rotation of the second spiral worm gear 632 about a second axis, which is orthogonal to the first axis. As shown in FIGS. 32-33, for example, a CW rotation of the second spiral worm gear 632 results in a CW rotation of the shaft assembly 538 in the direction indicated by 634CW. A CCW rotation of the second spiral worm gear 632 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

In one example embodiment, the instrument mounting portion 558 comprises a mechanism for generating reciprocating translation of one or more members along the axis of the shaft 538. Such translation may be used, for example to drive a tissue cutting element, such as 555, drive an overtube for closure and/or articulation of the end effector 610, etc. In the illustrated embodiment, for example, a rack and pinion gearing mechanism may provide the reciprocating translation. A first gear 636 is coupled to a rotatable body 612 such that rotation of the corresponding driven element 564 causes the first gear 636 to rotate in a first direction. A second gear 638 is free to rotate about a post 640 formed in the instrument mounting plate 562. The first gear 636 is meshed to the second gear 638 such that the second gear 638 rotates in a direction that is opposite of the first gear 636. In one example embodiment, the second gear 638 is a pinion gear meshed to a rack gear 642, which moves in a liner direction. The rack gear 642 is coupled to a translating block 644, which may translate distally and proximally with the rack gear 642. The translation block 644 may be coupled to any suitable component of the shaft assembly 538 and/or the end effector 610 so as to provide reciprocating longitudinal motion. For example, the translation block 644 may be mechanically coupled to the tissue cutting element 555 of the RF surgical device 523. In some embodiments, the translation block 644 may be coupled to an overtube, or other component of the end effector 610 or shaft 538.

Figure 35:
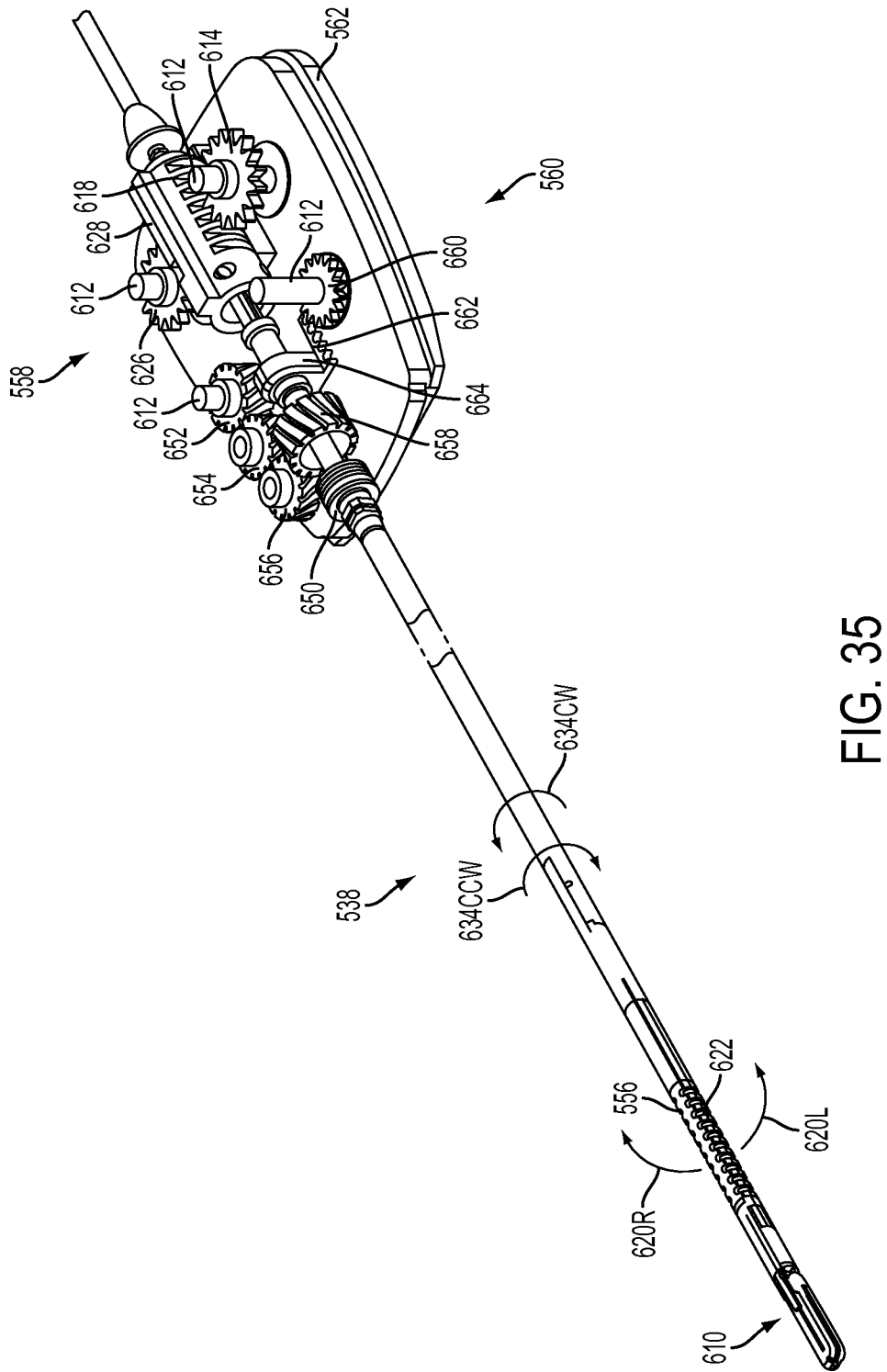
FIGS. 35-37 illustrate an alternate embodiment of the instrument mounting portion of FIGS. 24-25 showing an alternate example mechanism for translating rotation of the driven elements into rotational motion about the axis of the shaft and an alternate example mechanism for generating reciprocating translation of one or more members along the axis of the shaft 538.
Figure 36:
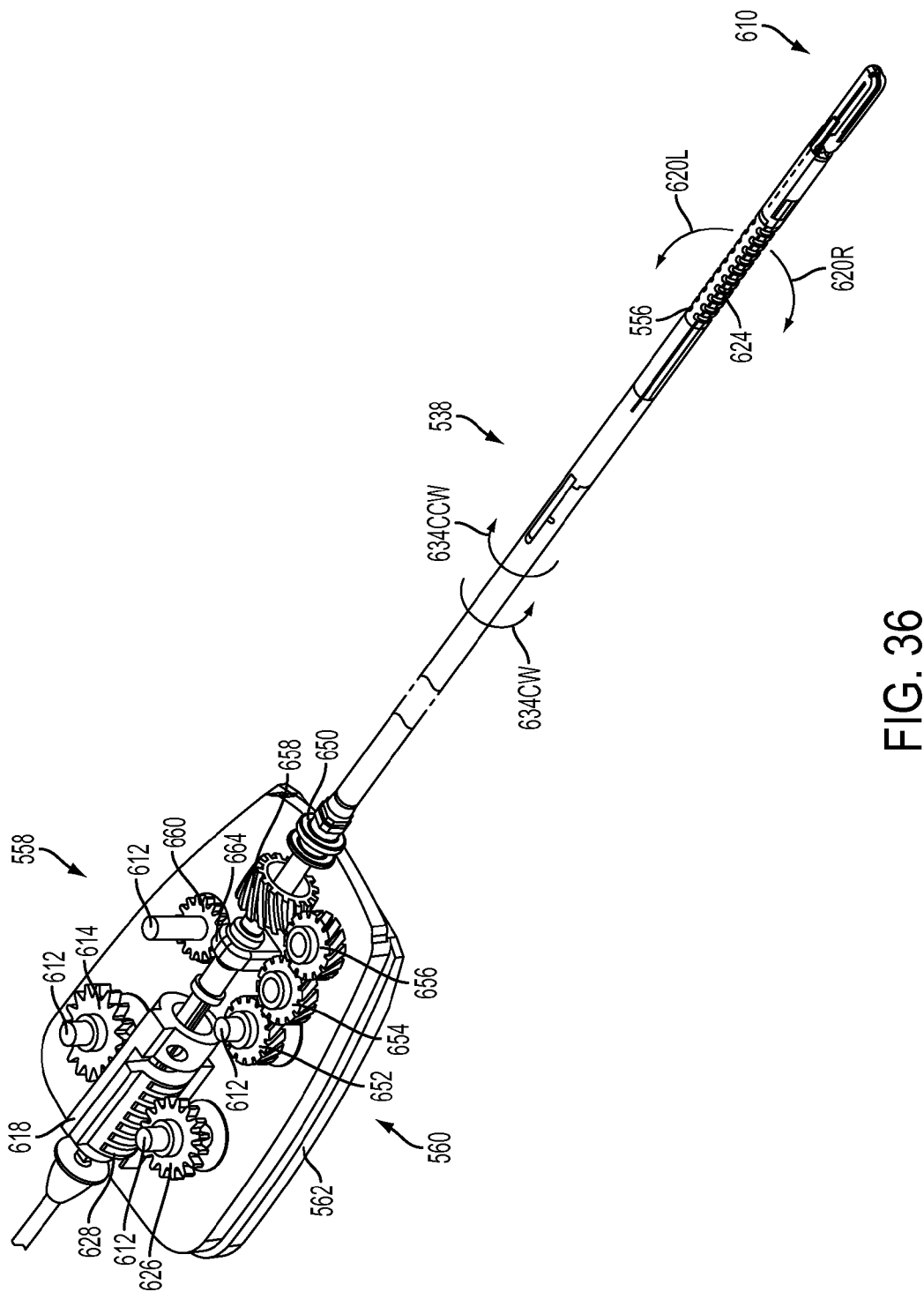
Figure 37:
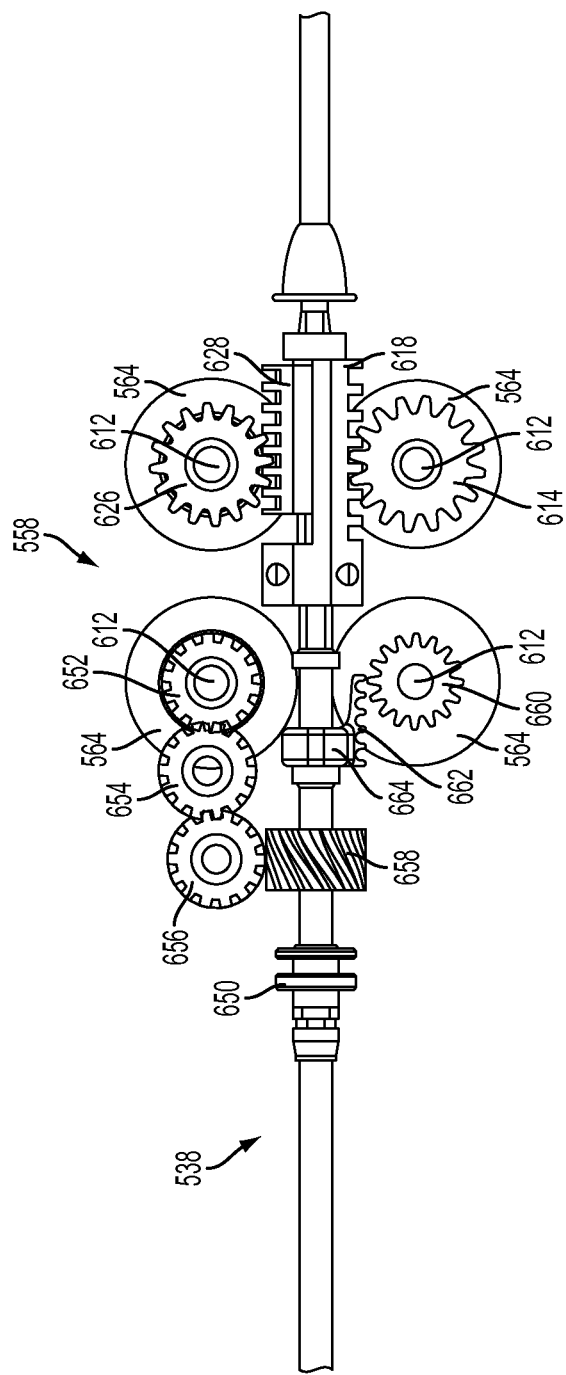

FIGS. 35-37 illustrate an alternate embodiment of the instrument mounting portion 558 showing an alternate example mechanism for translating rotation of the driven elements 564 into rotational motion about the axis of the shaft 538 and an alternate example mechanism for generating reciprocating translation of one or more members along the axis of the shaft 538. Referring now to the alternate rotational mechanism, a first spiral worm gear 652 is coupled to a second spiral worm gear 654, which is coupled to a third spiral worm gear 656. Such an arrangement may be provided for various reasons including maintaining compatibility with existing robotic systems 500 and/or where space may be limited. The first spiral worm gear 652 is coupled to a rotatable body 612. The third spiral worm gear 656 is meshed with a fourth spiral worm gear 658 coupled to the shaft assembly 538. A bearing 760 is coupled to a rotatable body 612 and is provided between a driven element 564 and the first spiral worm gear 738. Another bearing 760 is coupled to a rotatable body 612 and is provided between a driven element 564 and the third spiral worm gear 652. The third spiral worm gear 652 is meshed to the fourth spiral worm gear 658, which may be coupled to the shaft assembly 538 and/or to another component of the instrument 522, 523 for which longitudinal rotation is desired. Rotation may be caused in a CW and a CCW direction based on the rotational direction of the spiral worm gears 656, 658. Accordingly, rotation of the third spiral worm gear 656 about a first axis is converted to rotation of the fourth spiral worm gear 658 about a second axis, which is orthogonal to the first axis. As shown in FIGS. 0 and P, for example, the fourth spiral worm gear 558 is coupled to the shaft 538, and a CW rotation of the fourth spiral worm gear 658 results in a CW rotation of the shaft assembly 538 in the direction indicated by 634CW. A CCW rotation of the fourth spiral worm gear 658 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

Referring now to the alternate example mechanism for generating reciprocating translation of one or more members along the axis of the shaft 538, the instrument mounting portion 558 comprises a rack and pinion gearing mechanism to provide reciprocating translation along the axis of the shaft 538 (e.g., translation of a tissue cutting element 555 of the RF surgical device 523). In one example embodiment, a third pinion gear 660 is coupled to a rotatable body 612 such that rotation of the corresponding driven element 564 causes the third pinion gear 660 to rotate in a first direction. The third pinion gear 660 is meshed to a rack gear 662, which moves in a linear direction. The rack gear 662 is coupled to a translating block 664. The translating block 664 may be coupled to a component of the device 522, 523, such as, for example, the tissue cutting element 555 of the RF surgical device and/or an overtube or other component which is desired to be translated longitudinally.

Figure 38:
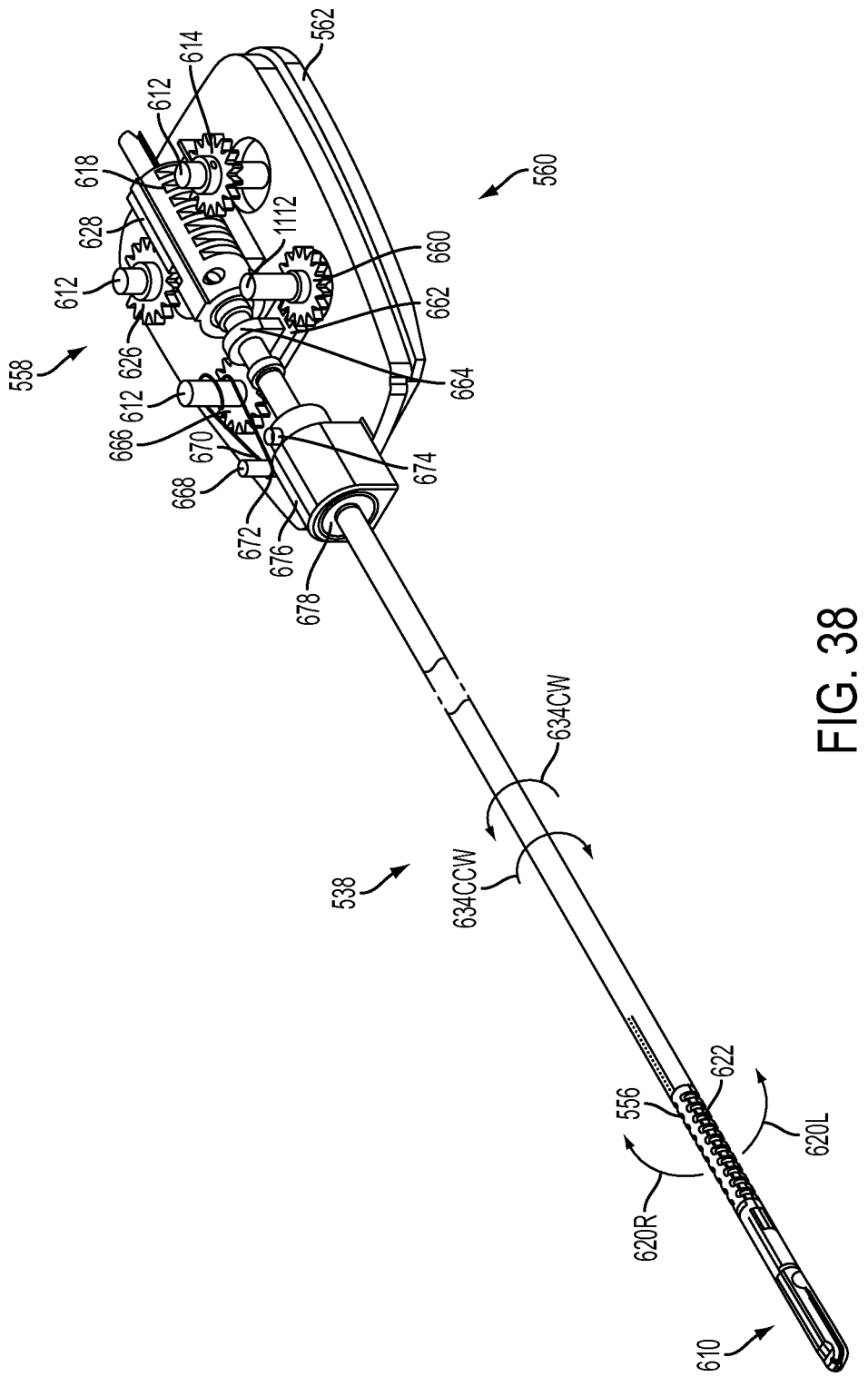
FIGS. 38-42 illustrate an alternate embodiment of the instrument mounting portion FIGS. 24-25 showing another alternate example mechanism for translating rotation of the driven elements into rotational motion about the axis of the shaft.
Figure 39:
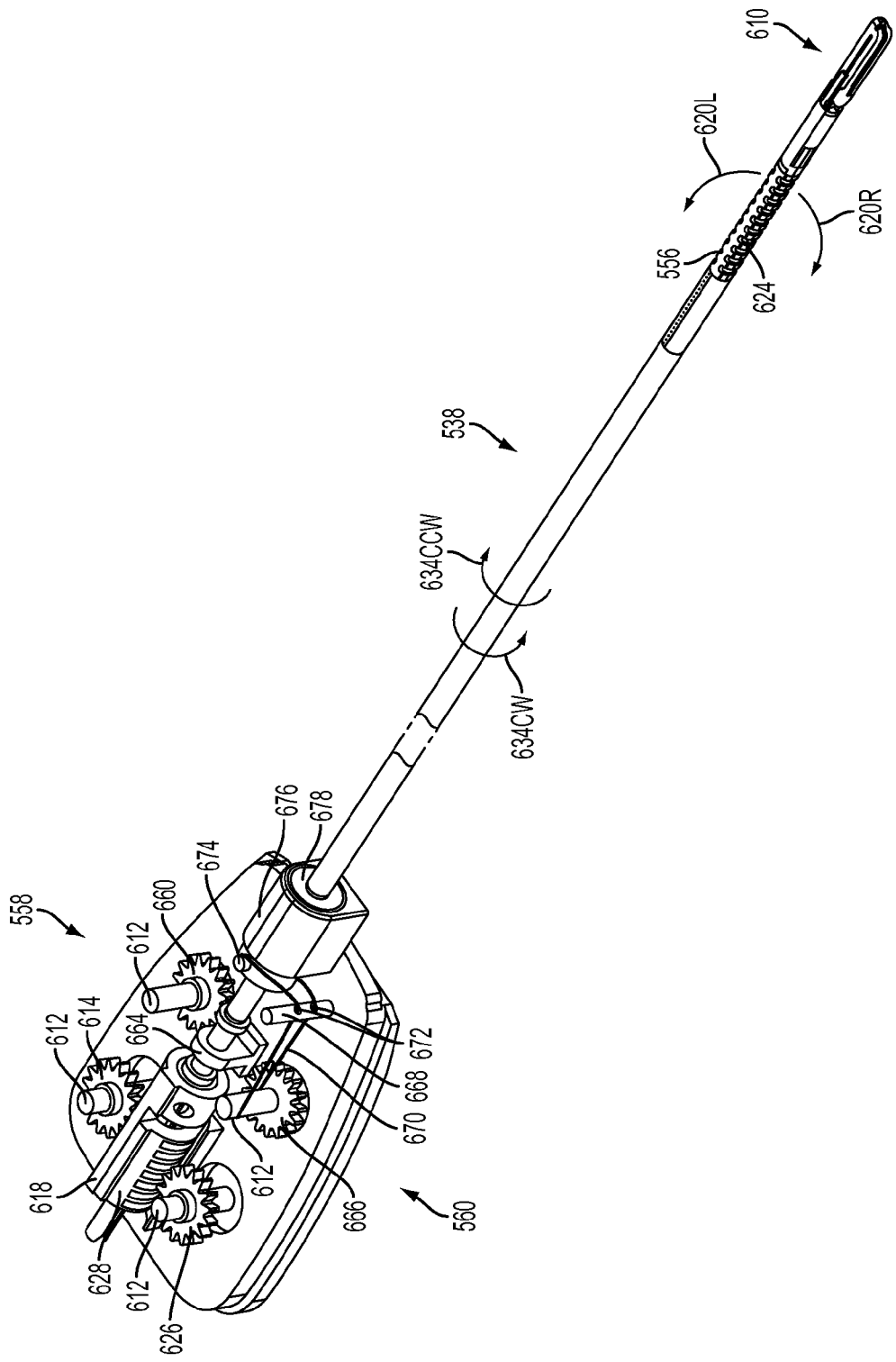
Figure 40:
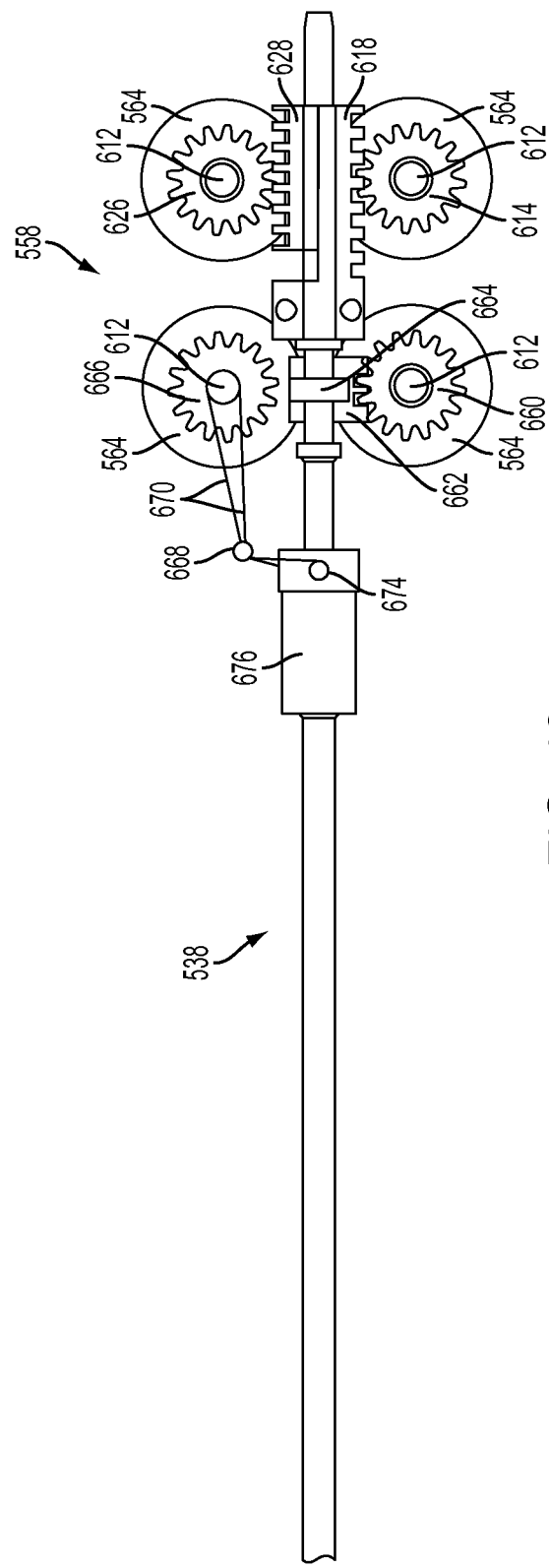
Figure 41:
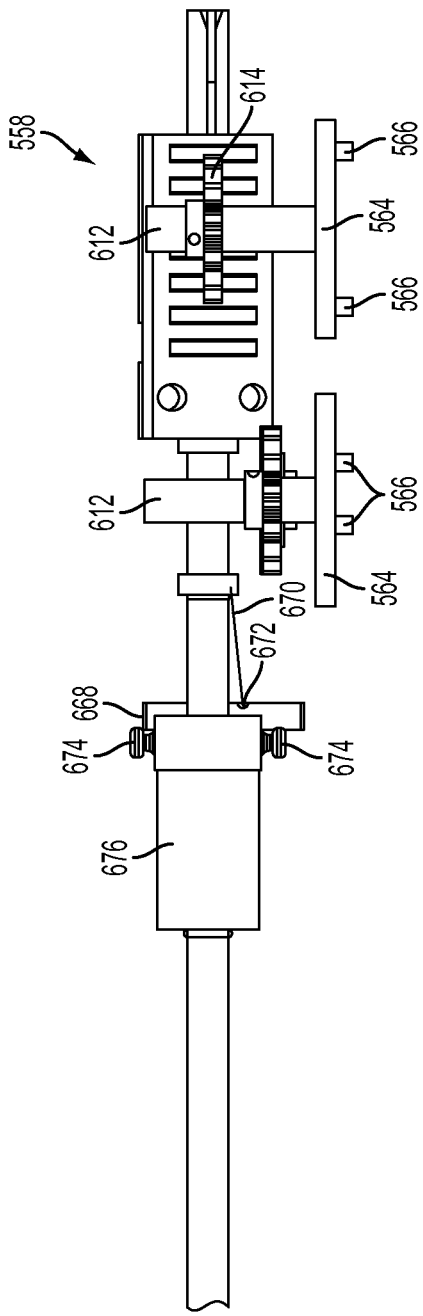
Figure 42:
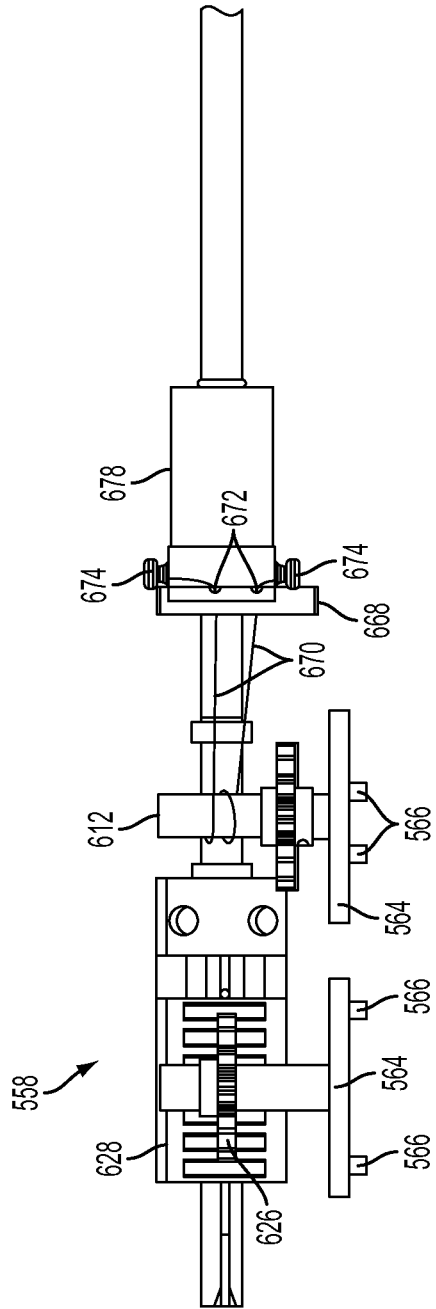
Figure 43:
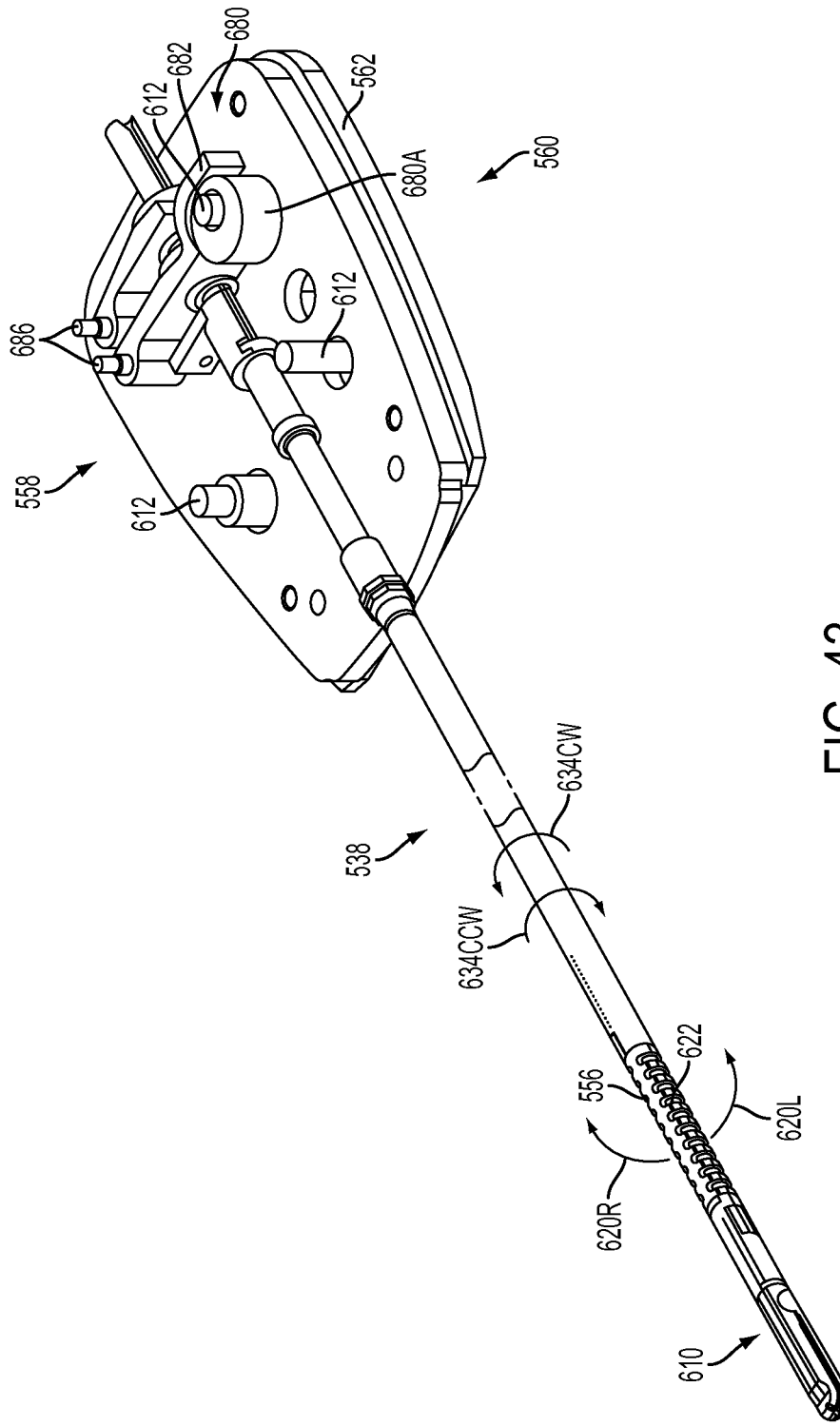
Figure 44:
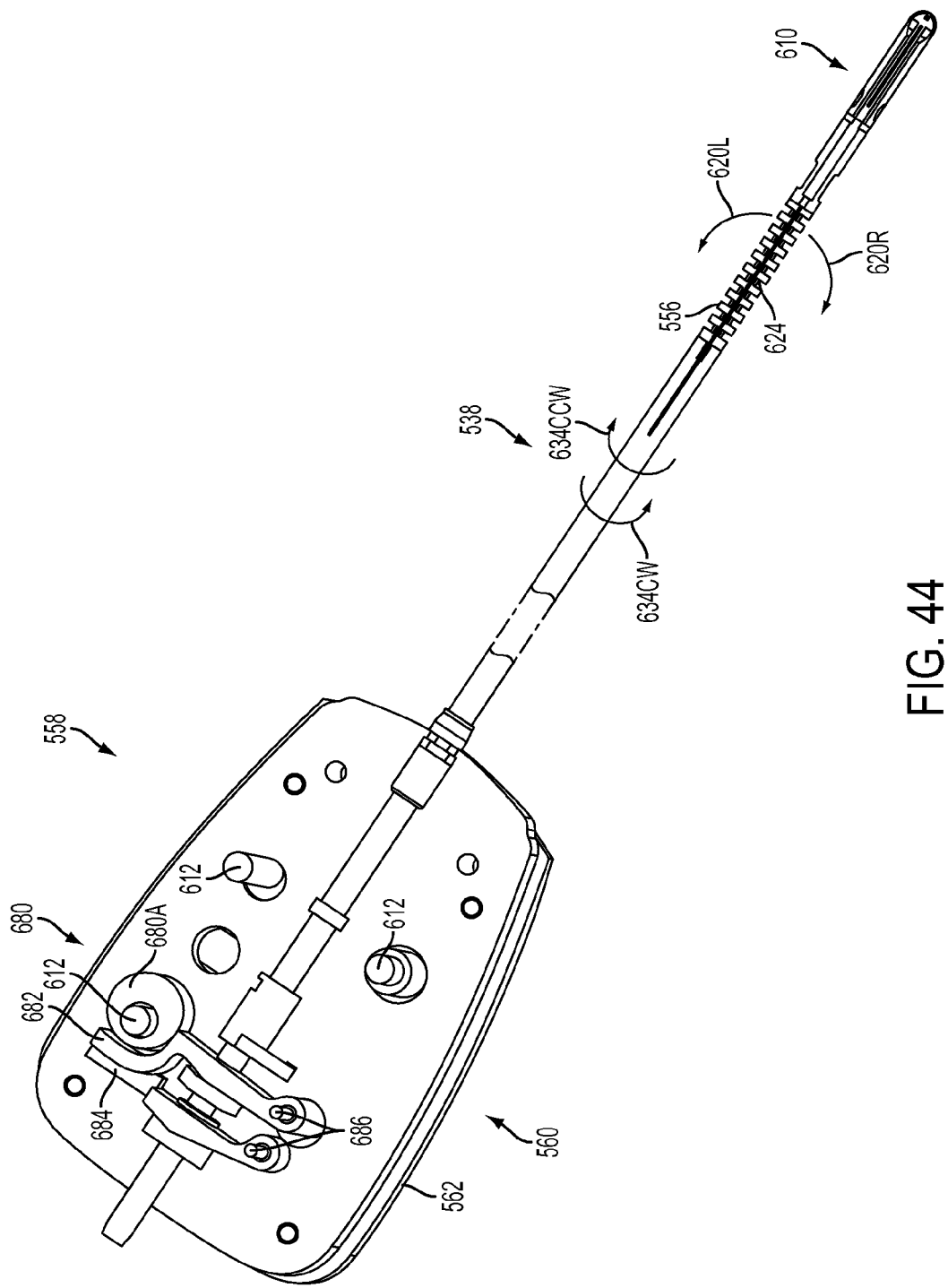

FIGS. 38-42 illustrate an alternate embodiment of the instrument mounting portion 558 showing another alternate example mechanism for translating rotation of the driven elements 564 into rotational motion about the axis of the shaft 538. In FIGS. 38-42, the shaft 538 is coupled to the remainder of the mounting portion 558 via a coupler 676 and a bushing 678. A first gear 666 coupled to a rotatable body 612, a fixed post 668 comprising first and second openings 672, first and second rotatable pins 674 coupled to the shaft assembly, and a cable 670 (or rope). The cable is wrapped around the rotatable body 612. One end of the cable 670 is located through a top opening 672 of the fixed post 668 and fixedly coupled to a top rotatable pin 674. Another end of the cable 670 is located through a bottom opening 672 of the fixed post 668 and fixedly coupled to a bottom rotating pin 674. Such an arrangement is provided for various reasons including maintaining compatibility with existing robotic systems 500 and/or where space may be limited. Accordingly, rotation of the rotatable body 612 causes the rotation about the shaft assembly 538 in a CW and a CCW direction based on the rotational direction of the rotatable body 612 (e.g., rotation of the shaft 538 itself). Accordingly, rotation of the rotatable body 612 about a first axis is converted to rotation of the shaft assembly 538 about a second axis, which is orthogonal to the first axis. As shown in FIGS. 38, 39, for example, a CW rotation of the rotatable body 612 results in a CW rotation of the shaft assembly 538 in the direction indicated by 634CW. A CCW rotation of the rotatable body 612 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

Figure 46A:
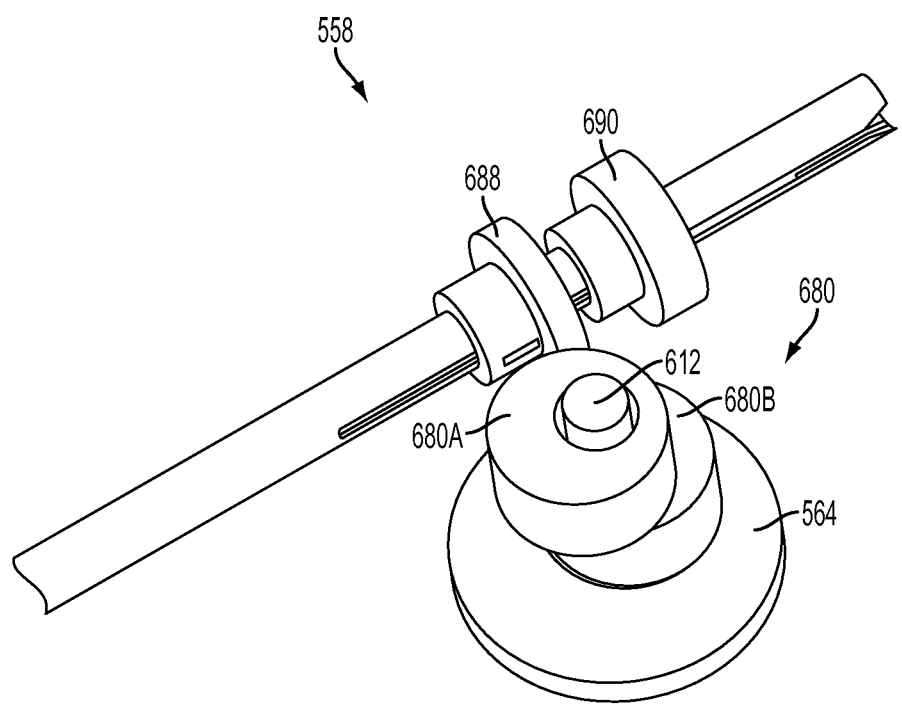

FIGS. 43-46A illustrate an alternate embodiment of the instrument mounting portion 558 showing an alternate example mechanism for differential translation of members along the axis of the shaft 538 (e.g., for articulation). For example, as illustrated in FIGS. 43-46A, the instrument mounting portion 558 comprises a double cam mechanism 680 to provide the shaft articulation functionality. In one example embodiment, the double cam mechanism 680 comprises first and second cam portions 680A, 680B. First and second follower arms 682, 684 are pivotally coupled to corresponding pivot spools 686. As the rotatable body 612 coupled to the double cam mechanism 680 rotates, the first cam portion 680A acts on the first follower arm 682 and the second cam portion 680B acts on the second follower arm 684. As the cam mechanism 680 rotates the follower arms 682, 684 pivot about the pivot spools 686. The first follower arm 682 may be attached to a first member that is to be differentially translated (e.g., the first articulation band 622). The second follower arm 684 is attached to a second member that is to be differentially translated (e.g., the second articulation band 624). As the top cam portion 680A acts of the first follower arm 682, the first and second members are differentially translated. In the example embodiment where the first and second members are the respective articulation bands 622 and 624, the shaft assembly 538 articulates in a left direction 620L. As the bottom cam portion 680B acts of the second follower arm 684, the shaft assembly 538 articulates in a right direction 620R. In some example embodiments, two separate bushings 688, 690 are mounted beneath the respective first and second follower arms 682, 684 to allow the rotation of the shaft without affecting the articulating positions of the first and second follower arms 682, 684. For articulation motion, these bushings reciprocate with the first and second follower arms 682, 684 without affecting the rotary position of the jaw 902. FIG. 46A shows the bushings 688, 690 and the dual cam assembly 680, including the first and second cam portions 680B, 680B, with the first and second follower arms 682, 684 removed to provide a more detailed and clearer view.

Figure 46B:
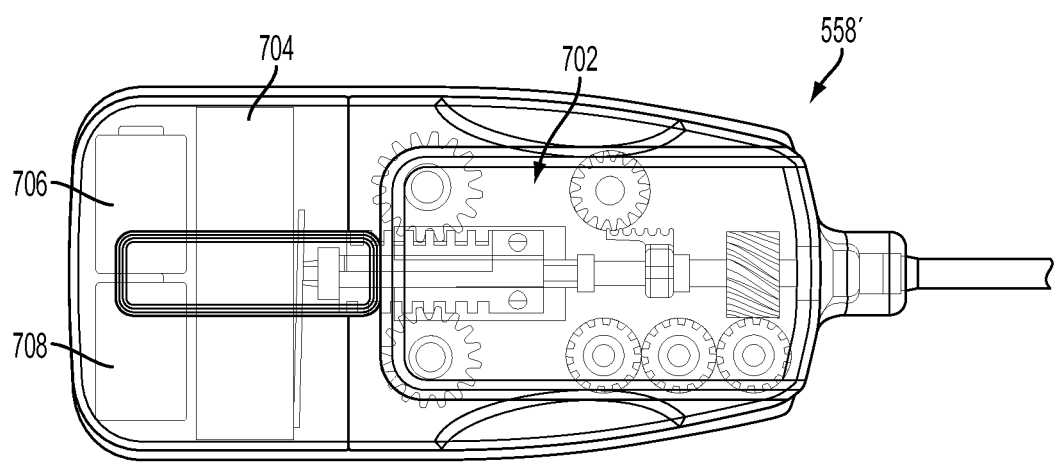
FIGS. 46B-46C illustrate one embodiment of a tool mounting portion comprising internal power and energy sources.
Figure 46C:
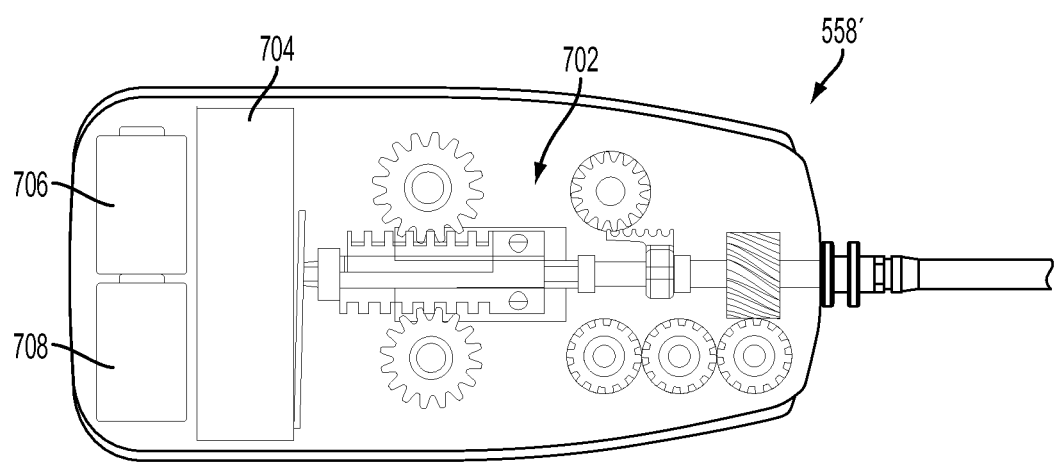

In various embodiments, the instrument mounting portion 558 may additionally comprise internal energy sources for driving electronics and provided desired ultrasonic and/or RF frequency signals to surgical tools. FIGS. 46B-46C illustrate one embodiment of a tool mounting portion 558' comprising internal power and energy sources. For example, surgical instruments (e.g., instruments 522, 523) mounted utilizing the tool mounting portion 558' need not be wired to an external generator or other power source. Instead, the functionality of the various generators 20, 320 described herein may be implemented on board the mounting portion 558.

As illustrated in FIGS. 46B-46C, the instrument mounting portion 558' may comprise a distal portion 702. The distal portion 702 may comprise various mechanisms for coupling rotation of drive elements 592 to end effectors of the various surgical instruments 522, 523, for example, as described herein above. Proximal of the distal portion 702, the instrument mounting portion 558' comprises an internal direct current (DC) energy source and an internal drive and control circuit 704. In the illustrated embodiment, the energy source comprises a first and second battery 706, 708. In other respects, the tool mounting portion 558' is similar to the various embodiments of the tool mounting portion 558 described herein above.

The control circuit 704 may operate in a manner similar to that described above with respect to generators 20, 320. For example, when an ultrasonic instrument 522 is utilized, the control circuit 704 may provide an ultrasonic drive signal in a manner similar to that described above with respect to generator 20. Also, for example, when an RF instrument 523 or ultrasonic instrument 522 capable of providing a therapeutic or non-therapeutic RF signal is used, the control circuit 704 may provide an RF drive signal, for example, as described herein above with respect to the module 23 of generator 20 and/or the generator 300. In some embodiments, the control circuit 704 may be configured in a manner similar to that of the control circuit 440 described herein above with respect to FIGS. 18B-18C.

Figure 47:
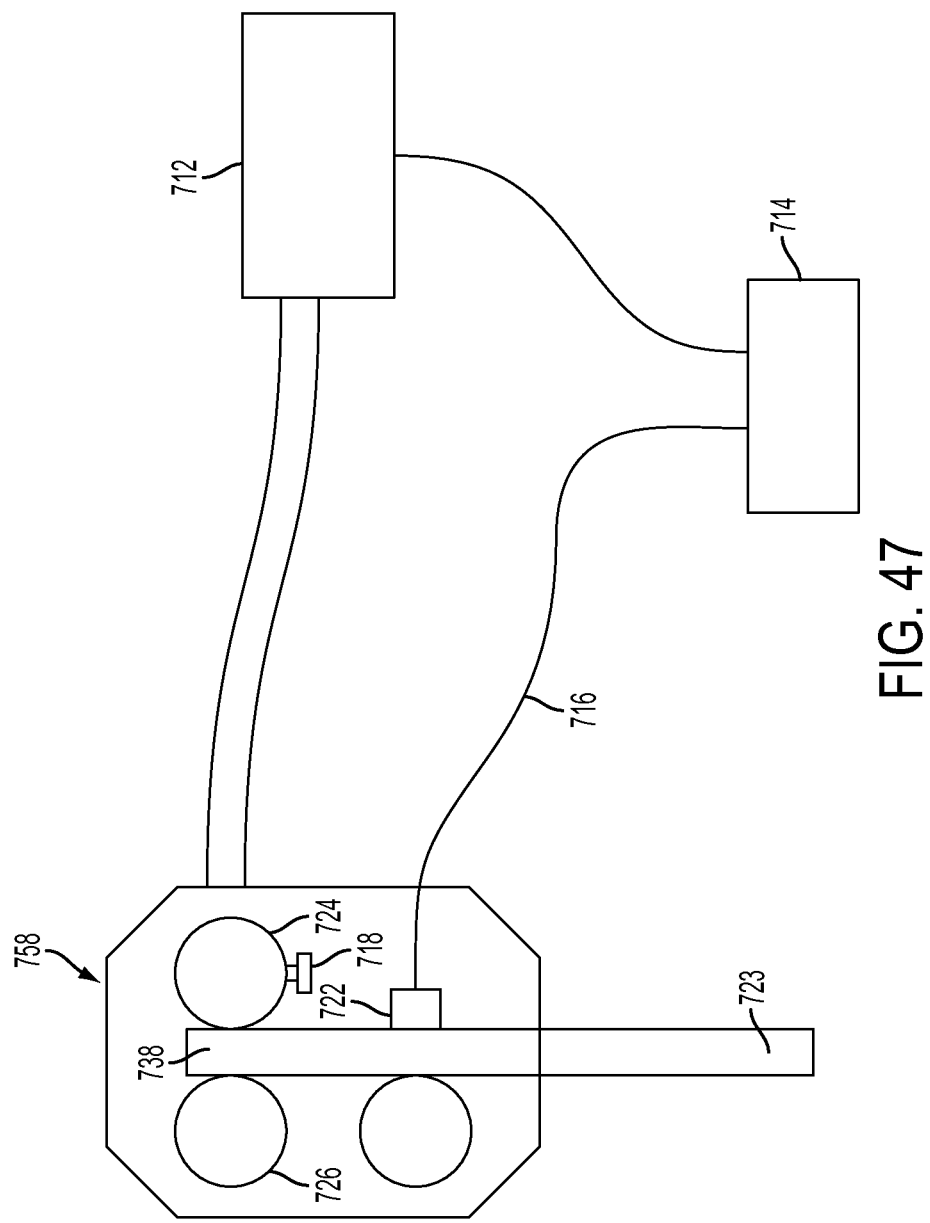
FIG. 47 illustrates one embodiment of an instrument mounting portion comprising a lockout mechanism and an end of stroke switch.

In some embodiments, it may be desirable to prevent actuation of an electrosurgical or ultrasonic end effector, such as, for example, the electrosurgical end effector 523, until energy has been applied to the electrosurgical or ultrasonic end effector. FIG. 47 shows one embodiment of an instrument mounting portion 758 comprising a lockout mechanism 722. In the embodiment shown in FIG. 47, actuation of the one or more members of end effector 723, such as, for example, a blade, may be prohibited through the use of a lockout mechanism 722. The lockout mechanism 722 operably interfaces with one or more of the mechanisms for generating reciprocating translation of one or more members along the axis of the shaft 738. In the embodiment shown in FIG. 47, the lockout mechanism interfaces directly with the shaft 738 to prevent reciprocal movement of the one or more members along the axis of the shaft 738. In other embodiments, the lockout mechanism 722 may interface with the one or more of the gears, such as, for example, the first gear 636 of the instrument mounting portion 758.

As shown in FIG. 47, the lockout mechanism may be directly connected to a switch 714, such as, for example, a foot switch. The switch 714 may be operated by a user to selectively disengage (or selectively engage) the lockout mechanism 722 to prevent reciprocating movement of the end effector 723. In the illustrated embodiment, the switch 714 is directly connected to the lockout mechanism 722 by a wire 716. It will be appreciated by those skilled in the art that the switch 714 and the lockout mechanism 722 may be in signal communication by a suitable method, including, but not limited to, direct communication, communication through one or more controllers, such as, for example, the robotic surgical control systems disclosed in co-filed application END7042USNP/110388. In other embodiments, the lockout mechanism 722 and the switch 714 may be in wireless communication using any suitable wireless communication protocol, such as, for example, Bluetooth communication.

The switch 714 may also be connected to the generator 712. The generator 712 is configured to provide one or more electrosurgical signals to the end effector 723. The electrosurgical signals delivered by the generator 712 may include, but are not limited to, ultrasonic signals, radiofrequency signals, or a combination thereof. A user may cause the generator to deliver the electrosurgical signal to the end effector 723 by activating the switch 714. In the illustrated embodiment, the lockout mechanism 722 and the generator 712 are controlled by the switch 714 such that reciprocating movement of the end effector 723 is allowed only when electrosurgical energy is being delivered to the end effector 723.

In another embodiment, the lockout mechanism 722 may be directly coupled to the generator 712 or the end effector 723. In this embodiment, the lockout mechanism 722 may be controlled by sensing the presence of the electrosurgical signal delivered by the generator 712 to the end effector 723. In this embodiment, the lockout mechanism 722 may prevent actuation of the one or more members of the end effector 723 if the generator 712 is faulty or is has not delivered the proper amount of energy to the end effector 723.

The instrument mounting portion 758 comprises an end-of-stroke switch 718 operatively coupled to the reciprocating movement element 724. The end-of-stroke switch 718 provides a signal indicative of the location of the one or more members within the end effector 723. In one embodiment, the end-of-stroke switch 718 may provide a feedback signal to a user indicating that the one or members have reached the distal most point of the reciprocating travel path. The user may then activate a reverse stroke algorithm to cause the one or more members to return from the distal most position to a proximal most, or starting, position. In another embodiment, the end-of-stroke switch 718 may cause the reverse stroke algorithm to automatically activate. In one embodiment, the end-of-stroke switch 718 may be connected to the lockout mechanism 722 such that the end-of-stroke switch 718 may engage the lockout mechanism 722 to prevent the one or more members of the end effector 723 from extending beyond a maximum distal displacement. In one embodiment, the end-of-stroke switch may prevent a signal from the switch 714 from being transmitted to the lockout mechanism 722 when the end-of-stroke switch 718 is activated, causing the lockout mechanism 722 to assume the default, locked position.

Figure 48:
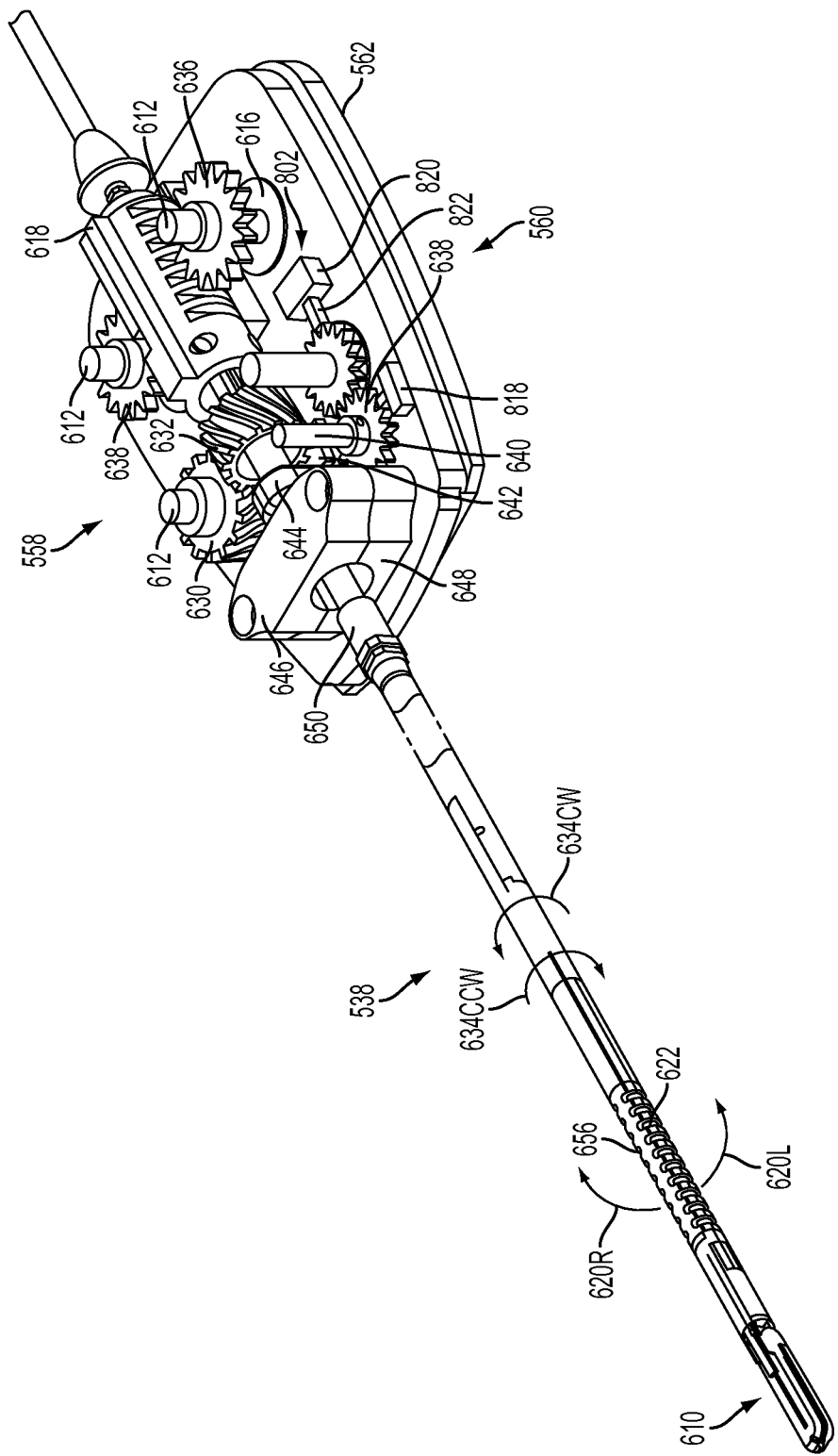
FIG. 48 illustrates one embodiment of the lockout mechanism interfaced with a first gear and the end-of-stroke switch interfaced with a second gear.

FIG. 48 illustrates one embodiment of instrument mounting portion 558 including a lockout mechanism 802. The lockout mechanism 802 mechanically interfaces with the first gear 636, which is coupled to a rotatable body 612. The lockout mechanism 802 prevents rotation of the first gear 636 by providing a mechanical stoppage interfaced with the first gear 636 from rotating. The mechanical stoppage may be, for example, a solenoid, a third gear, or any other suitable lockout device.

In one embodiment, the lockout mechanism is electrically coupled to a control switch located on the controller 518 (not shown). The control switch may be configured to control the delivery of energy to the end effector 610 from a generator, such as, for example, generator 320 (see FIG. 11). By actuating the control switch, a user may cause electrical energy to be delivered to the end effector 610 sufficient for use in electrosurgical applications.

In one embodiment, the control switch, in addition to allowing delivery of electrical energy to the end effector 610, causes the lockout mechanism 802 to disengage from the first gear 636, allowing rotation of the first gear 636 by the rotatable body 612. In this embodiment, the lockout mechanism 802 is directly connected to the delivery of electrical energy to the end effector 610. In other embodiments, the lockout mechanism 802 may be controlled by a second switch which is not used for delivery of electrical energy to the end effector 610.

In one embodiment, the end effector 723 may have a first state and a second state. In one embodiment, the first state may comprise a default, de-energized state wherein no energy is being applied by the generator 712 to the end effector 723. The second state may correspond to an energized state wherein the end effector 723 is energized by one or more forms of energy delivered by the generator 712. In one embodiment, in the energized state, the end effector may be energized with ultrasonic energy, radiofrequency energy, or both forms of energy. The lockout mechanism 722 may be electrically coupled to the end effector 723 such that the lockout mechanism 722 prevents actuation of the one or more members of the end effector 723 when the end effector 723 is in the first state and allows actuation of the one or more members when the end effector 723 is in the second state. In another embodiment, the first and second states may correspond to one or more mechanical states of the end effector 723, such as, for example, an end effector 723 comprising a staple cartridge may have a first state in which the staple cartridge is unloaded and a second state in which the staple cartridge is loaded. Those skilled in the art will appreciate that the first and second states may correspond to any suitable functions of the end effector 723.

As shown in FIG. 48, in one embodiment the lockout mechanism may comprise a solenoid 820. The solenoid 820 may be a linear pull type solenoid. In a pull type solenoid the plunger, such as, for example, armature 822, is biased in an extended position by a spring located within the solenoid. When the solenoid is energized, a coil (in the case of an electromagnetic solenoid) or a cylinder (in the case of a pneumatic solenoid) causes the plunger to retract into the body of the solenoid. The plunger returns to its biased, extended state when the solenoid is no longer energized. The solenoid 820 is a pull type solenoid with a default position of an extended armature 822, causing the default position of the lockout mechanism 802 to engage the first gear 636. Therefore, the default position of the lockout mechanism 802 is in a locked position. The solenoid 820 may also be a push type solenoid, wherein the biased and unbiased positions are reversed, and therefore would have a default position of an unlocked position.

In one embodiment, the instrument mounting portion 558 further comprises an end-of-stroke switch 818. The end-of-stroke switch 818 is operatively coupled to the mechanism for generating reciprocating translation of one or more members along the axis of the shaft 538. In the embodiment shown in FIG. 48, the end-of-stroke switch 818 is operatively coupled to the second gear 638. The end-of-stroke switch 818 provides a signal indicating that the one or more members have reached the distal most point of its reciprocating travel path within channel of the end effector 610.

In one embodiment, the end-of-stroke switch 818 may provide a feedback signal to a user indicating that the one or more members have reached the distal most point of the reciprocating travel path. The user may then activate a reverse stroke algorithm to cause the one or more members to return from the distal most position to a proximal most, or starting, position. In another embodiment, the end-of-stroke switch 818 may cause the reverse stroke algorithm to automatically activate. In this embodiment, the end-of-stroke switch 818 may be connected to a processor or other controller to reverse the direction of rotation of the rotatable body 612. In this embodiment, a user may activate a switch on a controller, such as controller 518, causing energy to be applied to the end effector 610. After energy has been applied, the controller may then actuate the solenoid 820 allowing the first gear 636 to rotate in response to rotation of the rotatable body 612 in a first direction. The rotation of the rotatable body 612 in the first direction causes one or more members, such as tissue cutting element 555, to advance in a distal direction with respect to the instrument mounting portion housing 582. Once the tissue cutting element 555 has reached the distal-most point of travel, the end-of-stroke switch 818 activates, causing the controller to reverse the direction of rotation of the rotatable body and the tissue cutting element 555 to travel in a proximal direction relative to the instrument mounting portion housing 582. Once the tissue cutting element 555 has returned to the proximal most position, the end-of-stroke switch 818 is again activated by the second gear 638, which causes the rotatable body 612 to cease rotating and re-engages the lockout mechanism 802 with the first gear 636.

Figure 49:
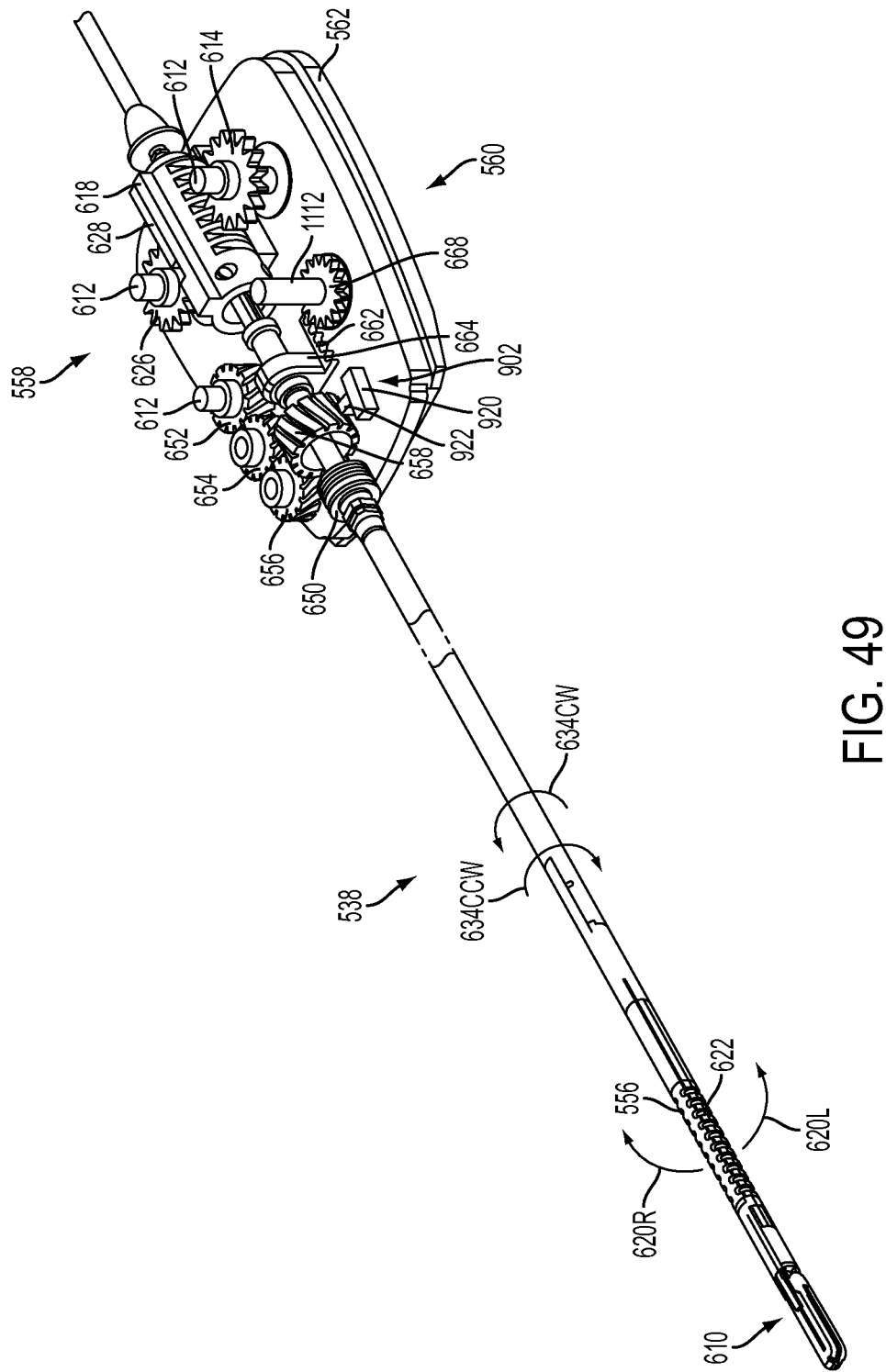
FIG. 49 illustrates one embodiment of the lockout mechanism interfaced with a worm gear mounted to the shaft assembly.

FIG. 49 illustrates one embodiment of the lockout mechanism 902 directly interfaced with the fourth spiral worm gear 658 of the shaft assembly 538. In this embodiment, the lockout mechanism 902 prevents the fourth spiral worm gear 658 from being rotated by the third spiral worm gear 656. In this embodiment, the lockout mechanism 902 prevents reciprocating movement of the one or more members by preventing rotation of the fourth worm gear 656 which is coupled to the shaft assembly 538.

In one embodiment, the lockout mechanism 722, 802, 902 may be controlled by one or more logic controls (not shown). The one or more logic controls may be located, for example, in the instrument mounting portion assembly 558 or on the controller 518. The one or more logic controls may control the lockout mechanism 722 to allow reciprocating movement of the one or more members during specific sequences controlled by the one or more logic controls, such as, for example, a cutting and sealing algorithm controlled by one or more processors included with the controller 518. The one or more logic controls may be any suitable logic for controlling the lockout mechanism 722, such as, for example, a computer processor running one or more software programs thereon or a programmable logic circuit, such as a field programmable gate array.

In one embodiment, the end-of-stroke switch 718 may coupled to the one or more logic controls to provide a control signal for one or more functions controlled by the one or more logic controls. For example, in one embodiment, the end-of-stroke switch 718 may provide a signal to the one or more logic controls which cause the one or more logic controls to reverse the direction of travel of the one or more members of the end effector 723. In this embodiment, the one or more logic controls may automatically retract the one or more members to a proximal, or starting, position after the end-of-stroke switch 718 indicates that the one or more members have reached the distal-most position.

NON-LIMITING EXAMPLES

In one embodiment a surgical system is provided. The surgical system comprises a surgical tool, comprising an instrument mounting portion comprising a housing; a plate; a shaft assembly comprising an end effector, the end effector comprising a first jaw member and a second jaw member, the first and second jaw members defining a channel therebetween, and a blade slideably receivable within the channel to cut tissue located between the first and second jaw members; and a coupler to couple the shaft assembly to the instrument mounting portion; an actuation mechanism to actuate the end effector, wherein the actuation mechanism provides reciprocating movement of the blade within the channel; a lockout mechanism coupled to the actuation mechanism, the lockout mechanism to selectively enable reciprocating movement of the blade; and an interface to mechanically and electrically couple the instrument mounting portion to a manipulator; and a triggering mechanism for selectively activating the lockout mechanism.

In one embodiment a surgical tool is provided. The surgical tool comprises an instrument mounting portion housing; an instrument mounting portion plate; and a coupler to couple a shaft assembly to the instrument mounting portion, the shaft assembly comprising a RF end effector, the RF end effector having a first state wherein the RF end effector is energized with RF energy and a second state wherein the RF end effector is not energized with RF energy; an end effector actuation mechanism configured to actuate the RF end effector; a lockout mechanism coupled to the end effector actuation mechanism, wherein the wherein the lockout mechanism is mechanically coupled to the end effector actuation mechanism to allow actuation of the end effector actuation mechanism when the RF end effector is in the first state and to prevent actuation of the end effector actuation mechanism when the RF end effector is in the second state, wherein the lockout mechanism is a solenoid; and an interface to mechanically and electrically couple the instrument mounting portion to a manipulator.

Applicant also owns the following patent applications that are each incorporated by reference in their respective entireties:

U.S. patent application Ser. No. 13/536,271, filed on Jun. 28, 2012 and entitled "Flexible Drive Member,";

U.S. patent application Ser. No. 13/536,288, filed on Jun. 28, 2012 and entitled "Multi-Functional Powered Surgical Device with External Dissection Features,";

U.S. patent application Ser. No. 13/536,295, filed on Jun. 28, 2012 and entitled "Rotary Actuatable Closure Arrangement for Surgical End Effector,";

U.S. patent application Ser. No. 13/536,326, filed on Jun. 28, 2012 and entitled "Surgical End Effectors Having Angled Tissue-Contacting Surfaces,";

U.S. patent application Ser. No. 13/536,303, filed on Jun. 28, 2012 and entitled "Interchangeable End Effector Coupling Arrangement,";

U.S. patent application Ser. No. 13/536,393, filed on Jun. 28, 2012 and entitled "Surgical End Effector Jaw and Electrode Configurations,";

U.S. patent application Ser. No. 13/536,362, filed on Jun. 28, 2012 and entitled "Multi-Axis Articulating and Rotating Surgical Tools,"; and U.S. patent application Ser. No. 13/536,417, filed on Jun. 28, 2012 and entitled "Electrode Connections for Rotary Driven Surgical Tools,".

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated embodiments. However, surgical instruments may be used in many orientations and positions, and these terms are not intended to be limiting or absolute.

Various embodiments of surgical instruments and robotic surgical systems are described herein. It will be understood by those skilled in the art that the various embodiments described herein may be used with the described surgical instruments and robotic surgical systems. The descriptions are provided for example only, and those skilled in the art will understand that the disclosed embodiments are not limited to only the devices disclosed herein, but may be used with any compatible surgical instrument or robotic surgical system.

Reference throughout the specification to "various embodiments," "some embodiments," "one example embodiment," or "an embodiment" means that a particular feature, structure, or characteristic described in connection with the embodiment is included in at least one example embodiment. Thus, appearances of the phrases "in various embodiments," "in some embodiments," "in one example embodiment," or "in an embodiment" in places throughout the specification are not necessarily all referring to the same embodiment. Furthermore, the particular features, structures, or characteristics illustrated or described in connection with one example embodiment may be combined, in whole or in part, with features, structures, or characteristics of one or more other embodiments without limitation.

While various embodiments herein have been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical tool, comprising:
   an instrument mounting portion comprising:
      a housing;
      a plate;
      a shaft assembly comprising an end effector, the end effector comprising a first jaw member and a second jaw member, the first and second jaw members defining a channel therebetween, and a blade slideably receivable within the channel, the blade configured to cut tissue located between the first and second jaw members; and
      a coupler configured to couple the shaft assembly to the instrument mounting portion;
   an actuation mechanism configured to actuate the end effector, wherein the actuation mechanism provides reciprocating movement of the blade within the channel;
   a lockout mechanism coupled to the instrument mounting portion and in communication with the actuation mechanism, the lockout mechanism configured to selectively enable reciprocating movement of the blade; and
   an interface configured to mechanically and electrically couple the instrument mounting portion to a manipulator.

2. The surgical tool of claim 1, wherein:
   the end effector has a first state and a second state, wherein the lockout mechanism is configured to enable operation of the end effector actuation mechanism when the end effector is in the first state and to disable operation of the end effector actuation mechanism when the end effector is in the second state.

3. The surgical tool of claim 2, wherein the first state comprises an energized state and the second state comprises a de-energized state.

4. The surgical tool of claim 3, wherein the energized state comprises energizing the end effector with electrosurgical energy.

5. The surgical tool of claim 3, wherein the energized state comprises energizing the end effector with ultrasonic energy.

6. The surgical tool of claim 3, wherein the energized state comprises energizing the end effector with electrosurgical energy and ultrasonic energy.

7. The surgical tool of claim 1, wherein the lockout mechanism comprises a mechanical actuator arranged to engage the actuation mechanism when in a deployed state, wherein the mechanical actuator prevents movement of the actuation mechanism while in the deployed state.

8. The surgical tool of claim 7, wherein the mechanical actuator is a solenoid.

9. The surgical tool of claim 1, comprising an end of stroke indicator coupled to the end effector actuation mechanism such that the end of stroke indicator prevents the end effector actuation mechanism from extending beyond a predetermined maximum deployment.

10. A surgical system, comprising:
a surgical tool, comprising:
an instrument mounting portion comprising:
a housing;
a plate;
a shaft assembly comprising an end effector, the end effector comprising a first jaw member and a second jaw member, the first and second jaw members defining a channel therebetween, and a blade slideably receivable within the channel to cut tissue located between the first and second jaw members; and
a coupler configured to couple the shaft assembly to the instrument mounting portion;
an actuation mechanism configured to actuate the end effector, wherein the actuation mechanism provides reciprocating movement of the blade within the channel;
a lockout mechanism coupled to the instrument mounting portion and in communication with the actuation mechanism, the lockout mechanism configured to selectively enable reciprocating movement of the blade; and
an interface configured to mechanically and electrically couple the instrument mounting portion to a manipulator; and
a triggering mechanism for selectively activating the lockout mechanism.

11. The surgical system of claim 10, wherein the controller controls a state of the end effector, wherein the end effector has a first state wherein the end effector is energized by an energy source and a second state wherein the end effector is not energized by an energy source, and wherein the controller may selectively place the end effector in the first and second states.

12. The surgical system of claim 11,
wherein the lockout mechanism is configured to allow actuation of the end effector actuation mechanism when the end effector is in the first state; and
wherein the lockout mechanism is configured to prevent actuation of the end effector actuation mechanism when the end effector is in the second state.

13. The surgical system of claim 11, wherein the controller is a foot pedal.

14. The surgical system of claim 10, comprising an end of stroke indicator.

15. The surgical system of claim 14, wherein the end of stroke indicator activates a return-path action for the blade.

16. The surgical system of claim 10, wherein the end effector actuation mechanism comprises a rack and pinion.

17. The surgical system of claim 10, wherein the end effector actuation mechanism comprises one or more worm gears.

18. The surgical system of claim 10, wherein the lockout mechanism comprises a mechanical actuator arranged to engage the end effector actuation mechanism when in a deployed state.

19. The surgical system of claim 18, wherein the mechanical actuator is a solenoid.

20. A surgical tool, comprising:
an instrument mounting portion housing;
an instrument mounting portion plate;
a coupler to couple a shaft assembly to the instrument mounting portion plate, the shaft assembly comprising a radio frequency (RF) end effector, the RF end effector having a first state wherein the RF end effector is energized with RF energy and a second state wherein the RF end effector is not energized with RF energy;
an end effector actuation mechanism configured to actuate the RF end effector;
a lockout mechanism coupled to the instrument mounting portion housing and the end effector actuation mechanism, wherein the lockout mechanism is mechanically coupled to the end effector actuation mechanism configured to allow actuation of the end effector actuation mechanism when the RF end effector is in the first state and to prevent actuation of the end effector actuation mechanism when the RF end effector is in the second state, and wherein the lockout mechanism is a solenoid; and
an interface configured to mechanically and electrically couple the instrument mounting portion plate to a manipulator.

* * * * *